US011229687B2

(12) United States Patent
Lester et al.

(10) Patent No.: US 11,229,687 B2
(45) Date of Patent: *Jan. 25, 2022

(54) TPP-1 FORMULATIONS AND METHODS FOR TREATING CLN2 DISEASE

(71) Applicant: BioMarin Pharmaceutical Inc., Novato, CA (US)

(72) Inventors: Thomas Lester, Castro Valley, CA (US); Saeed Moshashaee, San Rafael, CA (US); Augustus O. Okhamafe, Concord, CA (US); Charles A. O'Neill, Vineburg, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/941,454

(22) Filed: Jul. 28, 2020

(65) Prior Publication Data

US 2020/0353059 A1 Nov. 12, 2020

Related U.S. Application Data

(63) Continuation of application No. 16/368,091, filed on Mar. 28, 2019, now Pat. No. 10,758,598, which is a (Continued)

(51) Int. Cl.
*A61K 31/198* (2006.01)
*A61P 25/28* (2006.01)
(Continued)

(52) U.S. Cl.
CPC ........ *A61K 38/4813* (2013.01); *A61K 9/0085* (2013.01); *A61K 9/08* (2013.01);
(Continued)

(58) Field of Classification Search
None
See application file for complete search history.

(56) References Cited

U.S. PATENT DOCUMENTS 6,302,685 B1 10/2001 Lobel et al.
6,638,712 B2 10/2003 Lobel et al.
(Continued)

FOREIGN PATENT DOCUMENTS

EP 2333074 A1 6/2011
WO WO-2013/096899 A2 6/2013
(Continued)

OTHER PUBLICATIONS

Bienaimé, J.P. Morgan Healthcare Conference 2015, BioMarin Pharmaceutical Inc. (2015).
(Continued)

*Primary Examiner* — Aurora M Fontainhas
(74) *Attorney, Agent, or Firm* — Marshall, Gerstein & Borun LLP

(57) ABSTRACT

Formulations comprising recombinant human tripeptidyl peptidase-1 (rhTPP1) for intrathecal, intracerebroventricular, or intraocular administration, and kits comprising the same, are disclosed. Methods of using rhTPP1 in the prevention and treatment of symptoms of Neuronal Ceroid Lipofuscinosis (CLN2) disease are also disclosed. The formulations and methods are effective in halting the progression of CLN2 disease and may be used to treat subjects having CLN2 or a family history of CLN2.

18 Claims, 53 Drawing Sheets

Specification includes a Sequence Listing.

SEQ ID NO: 1

```
  1    SYSPEPDQRR TLPPGWVSLG RADPEEELSL TFALRQQNVE RLSELVQAVS

51    DPSSPQYGKY LTLENVADLV RPSPLTLHTV QKWLLAAGAQ KCHSVITQDF

101    LTCWLSIRQA ELLLPGAEFH HYVGGPTETH VVRSPHPYQL PQALAPHVDF

151    VGGLHRFPPT SSLRQRPEPQ VTGTVGLHLG VTPSVIRKRY NLTSQDVGSG

201    TSNNSQACAQ FLEQYFHDSD LAQFMRLFGG NFAHQASVAR VVGQQGRGRA

251    GIEASLDVQY LMSAGANIST WVYSSPGRHE GQEPFLQWLM LLSNESALPH

301    VHTVSYGDDE DSLSSAYIQR VNTELMKAAA RGLTLLFASG DSGAGCWSVS

351    GRHQFRPTFP ASSPYVTTVG GTSFQEPFLI TNEIVDYISG GGFSNVFPRP

401    SYQEEAVTKF LSSSPHLPPS SYFNASGRAY PDVAALSDGY WVVSNRVPIP

451    WVSGTSASTP VFGGILSLIN EHRILSGRPP LGFLNPRLYQ QHGAGLFDVT

501    RGCHESCLDE EVEGQGFCSG PGWDPVTGWG TPNFPALLKT LLNP
```

Related U.S. Application Data continuation of application No. 15/147,485, filed on May 5, 2016, now Pat. No. 10,279,015.

(60) Provisional application No. 62/300,171, filed on Feb. 26, 2016, provisional application No. 62/158,789, filed on May 8, 2015.

(51) Int. Cl.

| | | |
|---|---|---|
| *A61K 38/48* | (2006.01) | |
| *A61K 9/00* | (2006.01) | |
| *A61K 47/02* | (2006.01) | |
| *C12N 9/48* | (2006.01) | |
| *A61M 5/14* | (2006.01) | |
| *A61K 9/08* | (2006.01) | |

(52) U.S. Cl.
CPC ............... *A61K 47/02* (2013.01); *A61M 5/14* (2013.01); *C12N 9/485* (2013.01); *A61K 9/0048* (2013.01); *C12Y 304/14009* (2013.01)

(56) References Cited

U.S. PATENT DOCUMENTS

| | | |
|---|---|---|
| 7,442,372 B2 | 10/2008 | Kakkis |
| 8,277,800 B2 | 10/2012 | Lobel et al. |
| 2005/0130117 A1 | 6/2005 | Davis et al. |
| 2010/0210604 A1 | 8/2010 | Meythaler |
| 2011/0166074 A1 | 7/2011 | Maxfield et al. |
| 2012/0148558 A1 | 6/2012 | Kakkis |
| 2012/0308544 A1 | 12/2012 | Steinfeld |
| 2013/0149318 A1 | 6/2013 | Reynolds et al. |

FOREIGN PATENT DOCUMENTS

| | | |
|---|---|---|
| WO | WO-2014/085621 A1 | 6/2014 |
| WO | WO-2014/089449 A1 | 6/2014 |
| WO | WO-2015/013148 A2 | 1/2015 |

OTHER PUBLICATIONS

BioMarin Provides Preliminary Data from Ongoing Phase 1/2 Pivotal Study of BMN 190 for Treatment of CLN2 Disorder, a Form of Batten Disease, Press Release, BioMarin Pharmaceutical Inc. (Jan. 12, 2015).
Brady et al., Enzyme replacement therapy for gaucher disease: Critical investigations beyond demonstration of clinical efficacy. *Biochem. Med. Metab. Biol.* 52: 1-9 (1994).
Chang et al., Converging paths of viral and non-viral vector engineering. *Molec. Ther.* 16: 1-8 (2008).
Chang et al., The Neuronal Ceroid Lipofuscinosis (Batten Disease), Oxford University Press, Chapter 7: pp. 80-109 (2011).
Dyke et al., Assessment of disease severity in late infantile neuronal ceroid lipofuscinosis using multiparametric MR imaging. *AJNR Am. J. Neuroradiol.* 34(4): 884-9 (2013).
European patent application No. 16793229.2, Extended European Search Report, dated Dec. 19, 2018.
Ezaki et al., A lysosomal proteinase, the late infantile neuronal ceroid lipofuscinosis gene (CLN2) product, is essential for degradation of a hydrophobic protein, the subunit c of ATP synthase. J. Neurochem. 72: 2573-82 (1999).
Gsponer et al., Theoretical approaches to protein aggregation, Protein Pept. Lett., 13(3):287-93 (2006).
Hartikainen et al., Late infantile neuronal ceroid lipofuscinosis is due to splicing mutations in the CLN2 gene. Molec. Genet. Metab. 67: 162-8 (1999).
Jones, Analysis of polypeptides and proteins. *Adv. Drug Delivery Rev.* 10(1): 29-90 (1993).
Katz et al., Enzyme replacement therapy attenuates disease progression in a canine model of late-infantile neuronal ceroid lipofuscinosis (CLN2 disease), J Neurosci Res. Nov. 2014;92(11):1591-8.
Lin et al., Production and characterization of recombinant human CLN2 protein for enzyme replacement therapy in late infantile neuronal ceroid lipofuscinosis. Biochem. J. 357: 49-55 (2001).
Lin et al., The human CLN2 protein/tripeptidyl-peptidase I is a serine protease that autoactivates at acidic pH. *J. Biol. Chem.* 276(3): 2249-55 (2001).
Mole et al., Neuronal ceroid-lipofuscinoses. Gene Rev. (2001).
Oyama et al., Catalytic residues and substrate specificity of recombinant human tripeptidyl peptidase I (CLN2). *J. Biochem.* 138(2): 127-34 (2005).
Paniagua Bravo et al., Quantitative t2 measurements in juvenile and late infantile neuronal ceroid lipofuscinosis. *Clin. Neuroradiol.* 23(3): 189-96 (2013).
Rider et al., Thirty years of Batten disease research: Present status and future goals. Molec. Genet. Metab. 66: 231-3 (1999).
Roberts, Therapeutic protein aggregation: mechanisms, design, and control, Trends Biotechnol., 32(7):372-80 (2014).
Schiffmann et al., Infusioni of alpha-galactosidase A reduces tissue globotriaosylceramide storage in patients with Fabry disease, Proc. Natl. Acad. Sci. USA, 97: 365-70 (2000).
Siesjo, The regulation of cerebrospinal fluid pH, Kidney Int., vol. 1, pp. 360-374 (1972).
Sleat et al., Association of mutations in a lysosomal protein with classical late-infantile neuronal ceroid lipofuscinosis. *Science*, 277(5333): 1802-5 (1997).
Sondhi et al., Feasibility of gene therapy for late neuronal ceroid lipofuscinosis. *Arch. Neurol.* 58: 1793-8 (2001).
Steinfeld et al., Late infantile neuronal ceroid lipofuscinosis: quantitative description of the clinical course in patients with CLN2 mutations. *Am. J. Med. Genet.* 112(4): 347-54 (2002).
Treuheit et al., Inverse relationship of protein concentration and aggregation, Pharm. Res., 19(4):511-6 (2002).
Vuillemenot et al., Intrathecal tripeptidyl-peptidase 1 reduces lysosomal storage in a canine model of late infantile neuronal ceroid lipofuscinosis, Mol. Genet. Metab., 104(3):325-37 (Nov. 2011).
Vuillemenot et al., Recombinant human tripeptidyl peptidase-1 infusion to the monkey CNS: safety, pharmacokinetics, and distribution, Toxicol. Appl. Pharmacol., 277(1):49-57 (May 2014).
Worgall et al., Neurological deterioration in late infantile neuronal ceroid lipofuscinosis. *Neurology*, 69(6): 521-35 (2007).
Xu et al., Large-Volume Intrathecal Enzyme Delivery Increases Survival of a Mouse Model of Late Infantile Neuronal Ceroid Lipofuscinosis, Molecular Therapy, 19(10):1842-1848 (2011).
Zhong et al., Two common mutations in the CLN2 gene underlie late infantile neuronal ceroid lipofuscinosis. *Clinical Genetics*, 54: 234-8 (1998).

SEQ ID NO: 1

| | | | | | |
|---|---|---|---|---|---|
| 1 | SYSPEPDQRR | TLPPGWVSLG | RADPEEELSL | TFALRQQNVE | RLSELVQAVS |
| 51 | DPSSPQYGKY | LTLENVADLV | RPSPLTLHTV | QKWLLAAGAQ | KCHSVITQDF |
| 101 | LTCWLSIRQA | ELLLPGAEFH | HYVGGPTETH | VVRSPHPYQL | PQALAPHVDF |
| 151 | VGGLHRFPPT | SSLRQRPEPQ | VTGTVGLHLG | VTPSVIRKRY | NLTSQDVGSG |
| 201 | TSNNSQACAQ | FLEQYFHDSD | LAQFMRLFGG | NFAHQASVAR | VVGQQGRGRA |
| 251 | GIEASLDVQY | LMSAGANIST | WVYSSPGRHE | GQEPFLQWLM | LLSNESALPH |
| 301 | VHTVSYGDDE | DSLSSAYIQR | VNTELMKAAA | RGLTLLFASG | DSGAGCWSVS |
| 351 | GRHQFRPTFP | ASSPYVTTVG | GTSFQEPFLI | TNEIVDYISG | GGFSNVFPRP |
| 401 | SYQEEAVTKF | LSSSPHLPPS | SYFNASGRAY | PDVAALSDGY | WVVSNRVPIP |
| 451 | WVSGTSASTP | VFGGILSLIN | EHRILSGRPP | LGFLNPRLYQ | QHGAGLFDVT |
| 501 | RGCHESCLDE | EVEGQGFCSG | PGWDPVTGWG | TPNFPALLKT | LLNP |

FIGURE 1

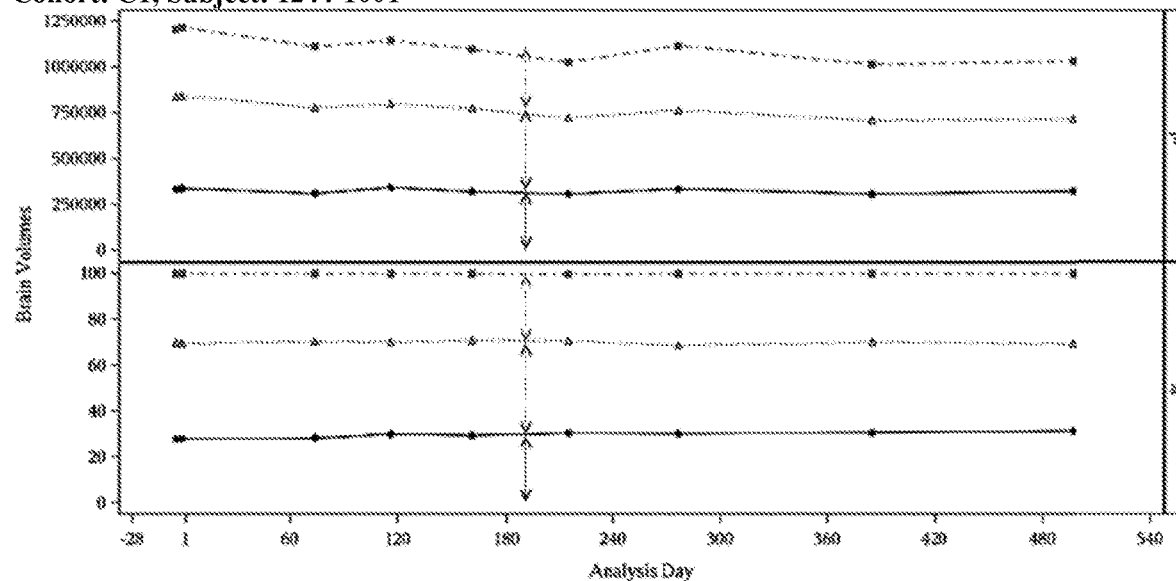
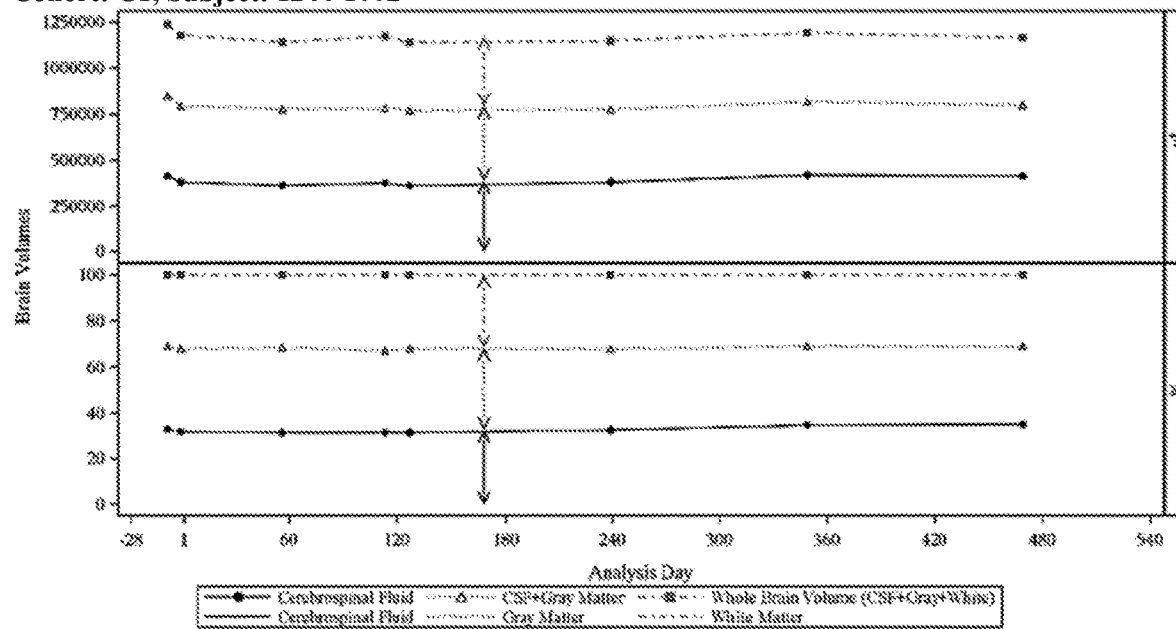
FIGURE 8A

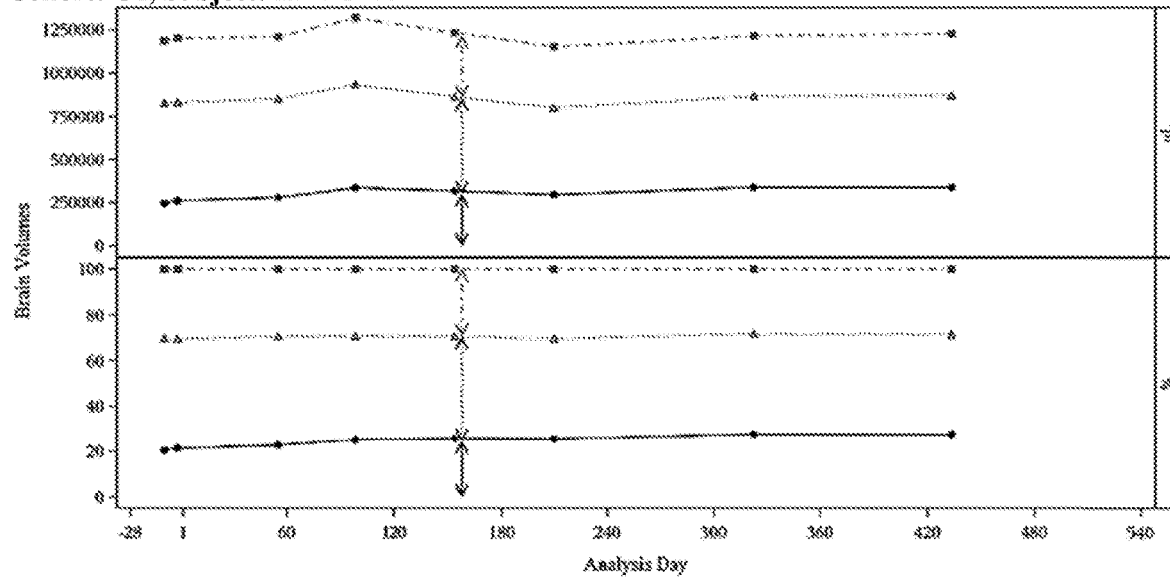
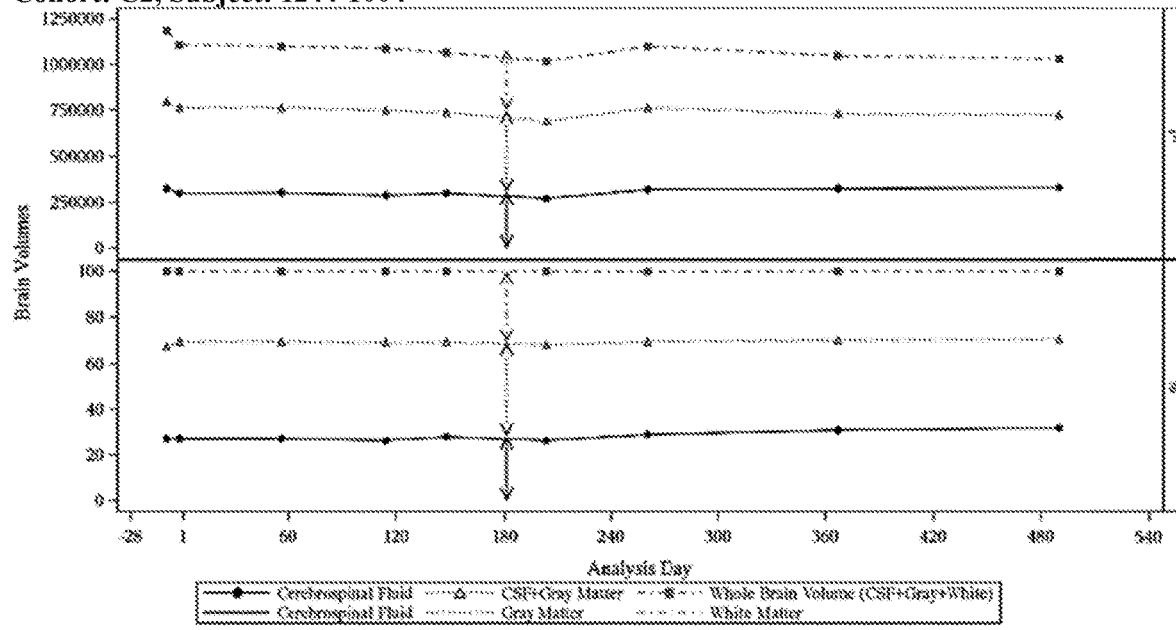
FIGURE 8B

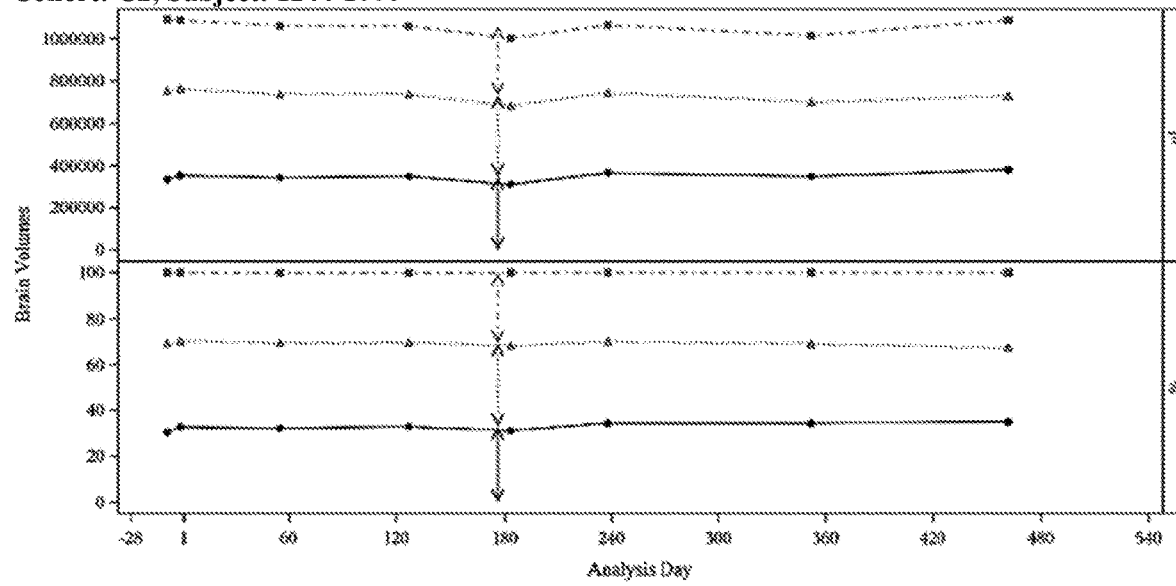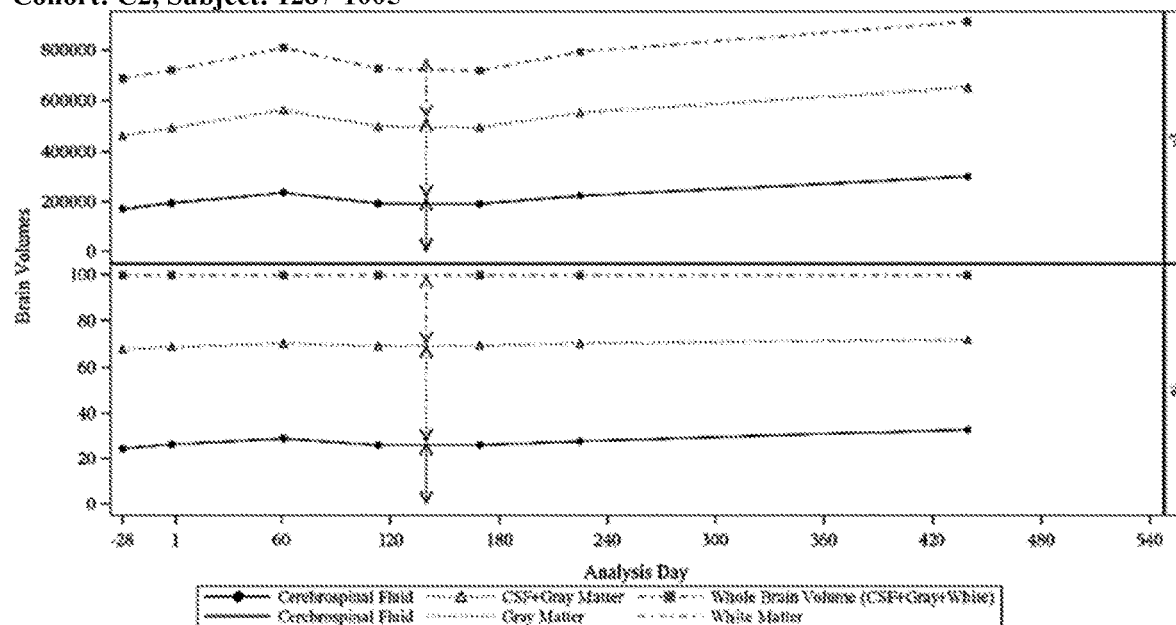
FIGURE 8C

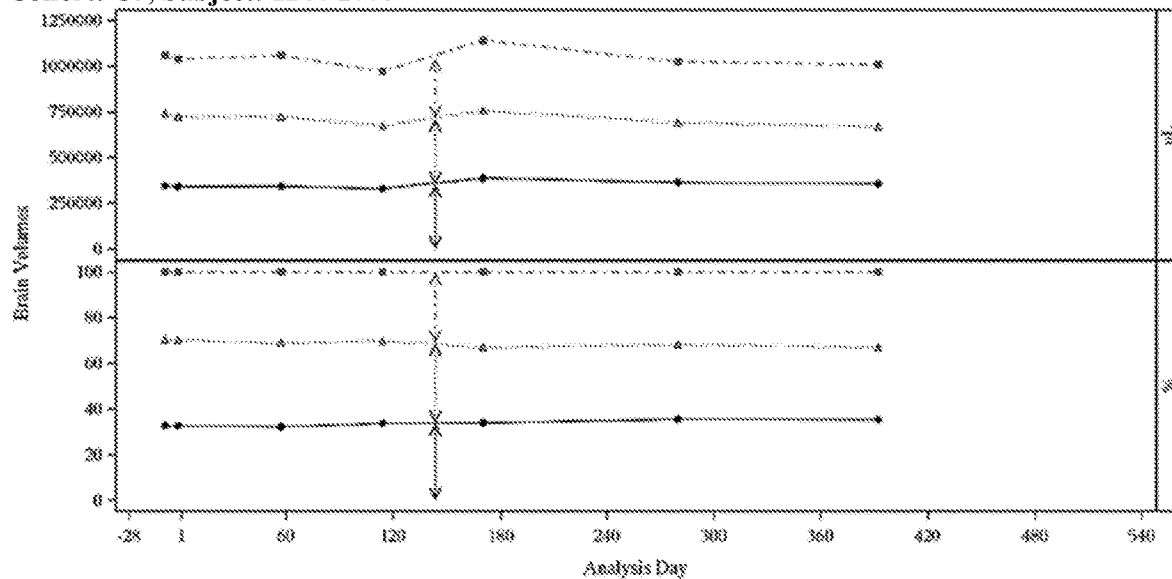
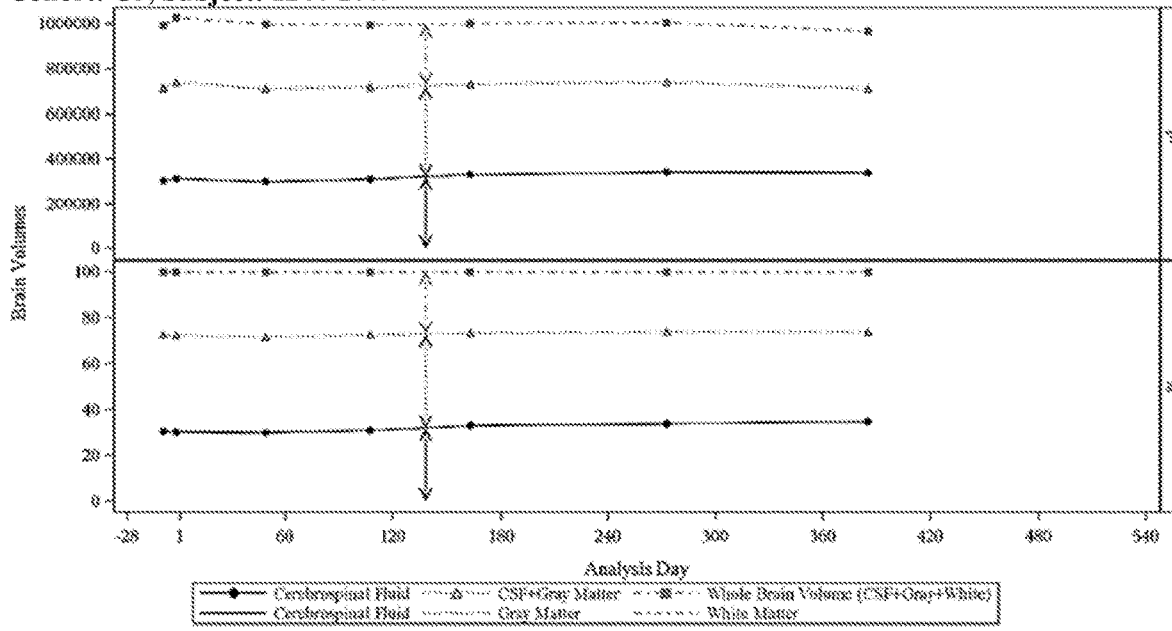
FIGURE 8D

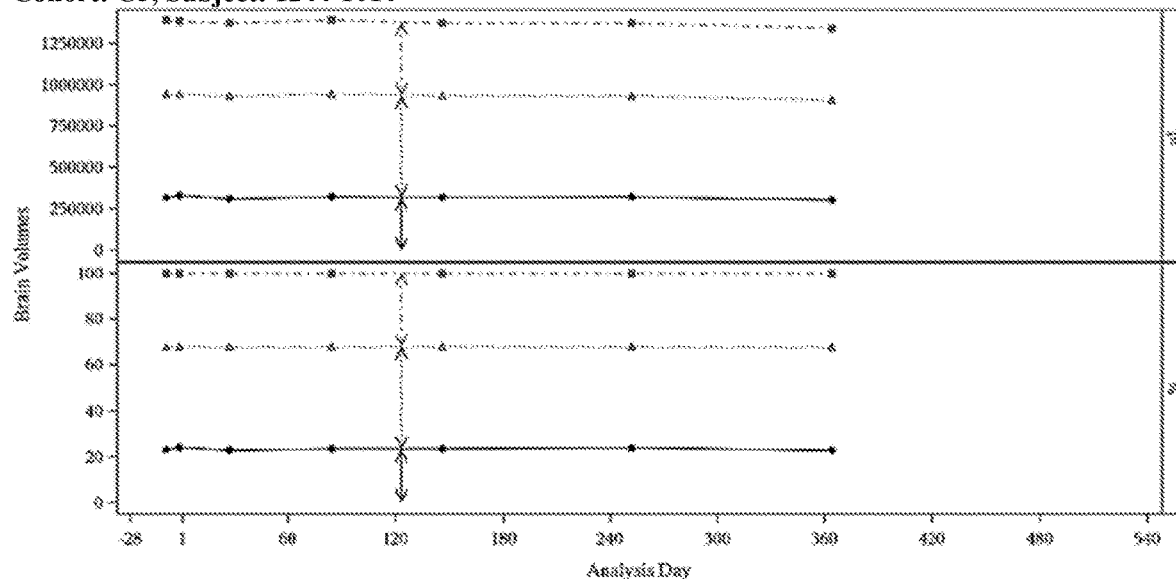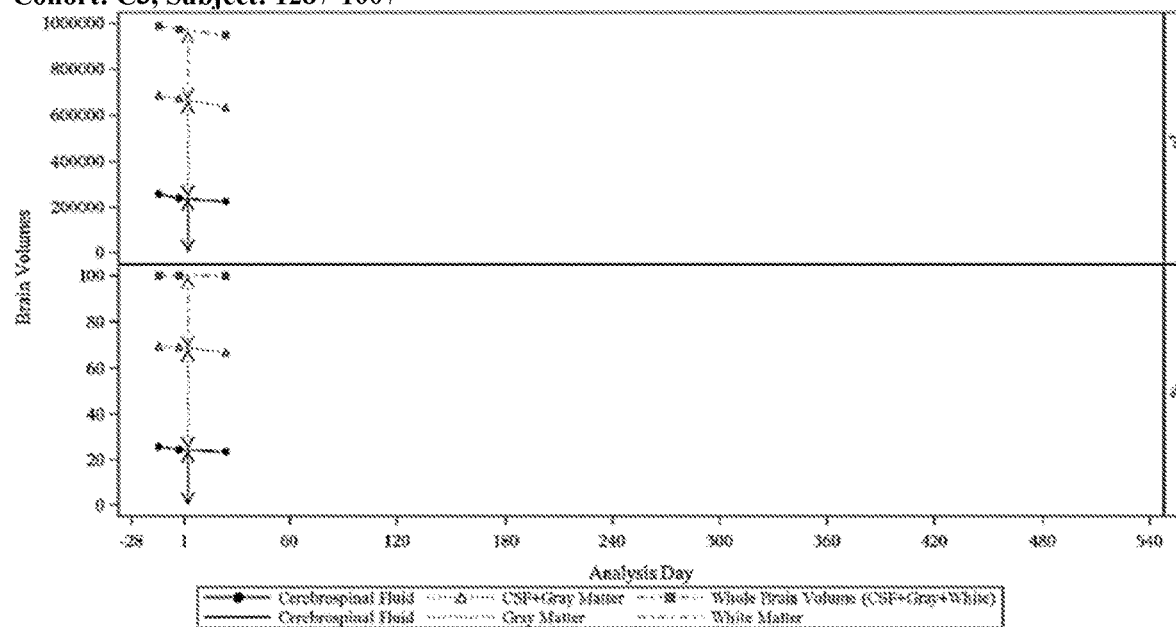
FIGURE 8E

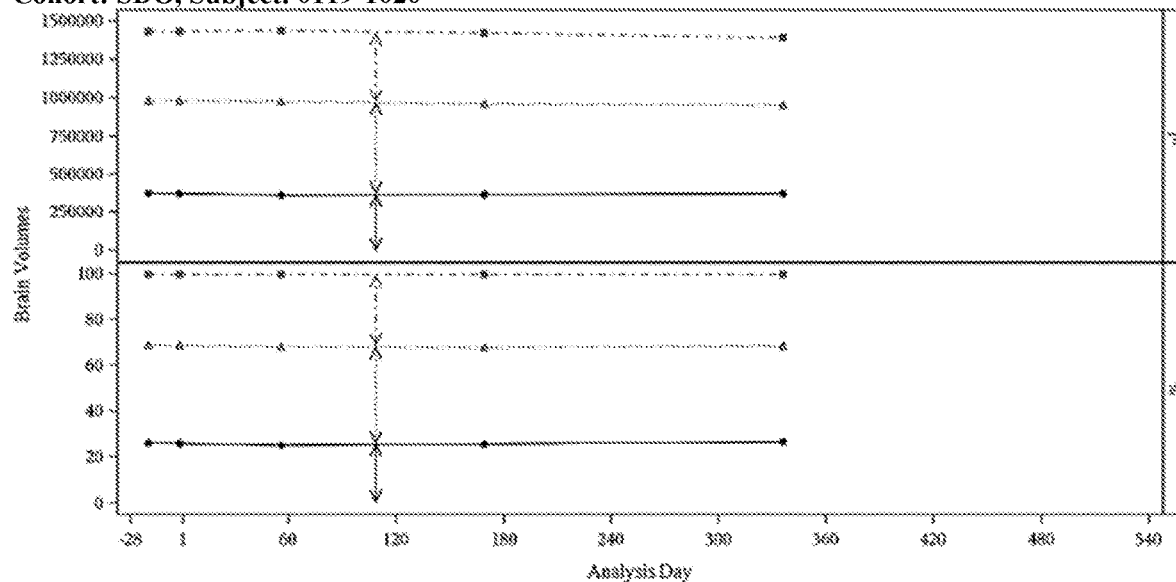
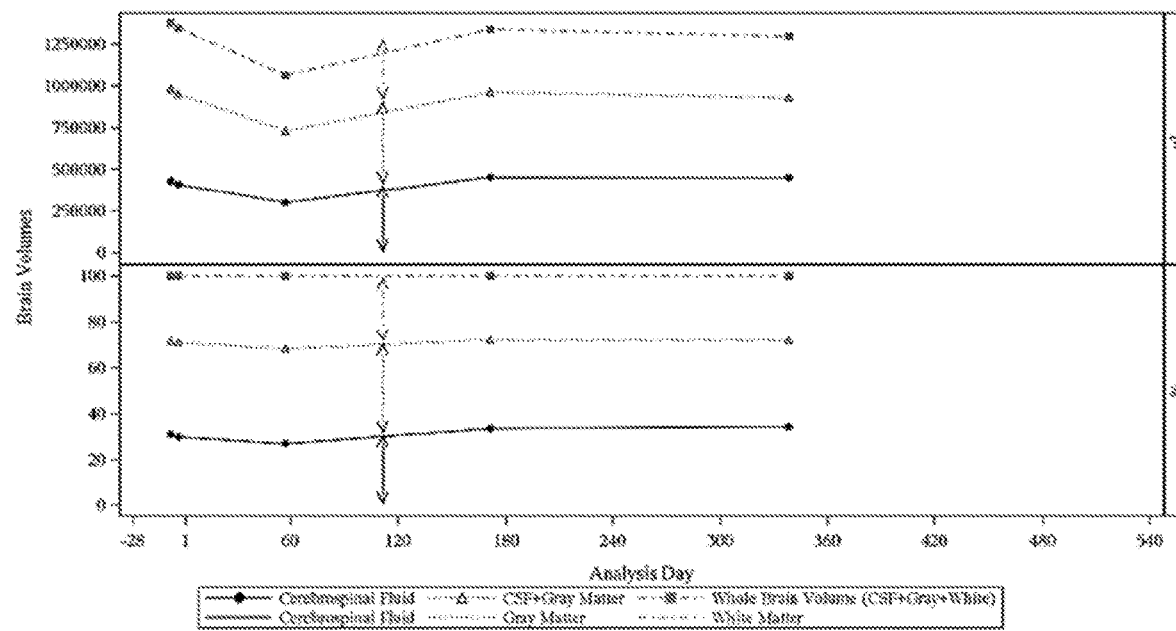
FIGURE 8F

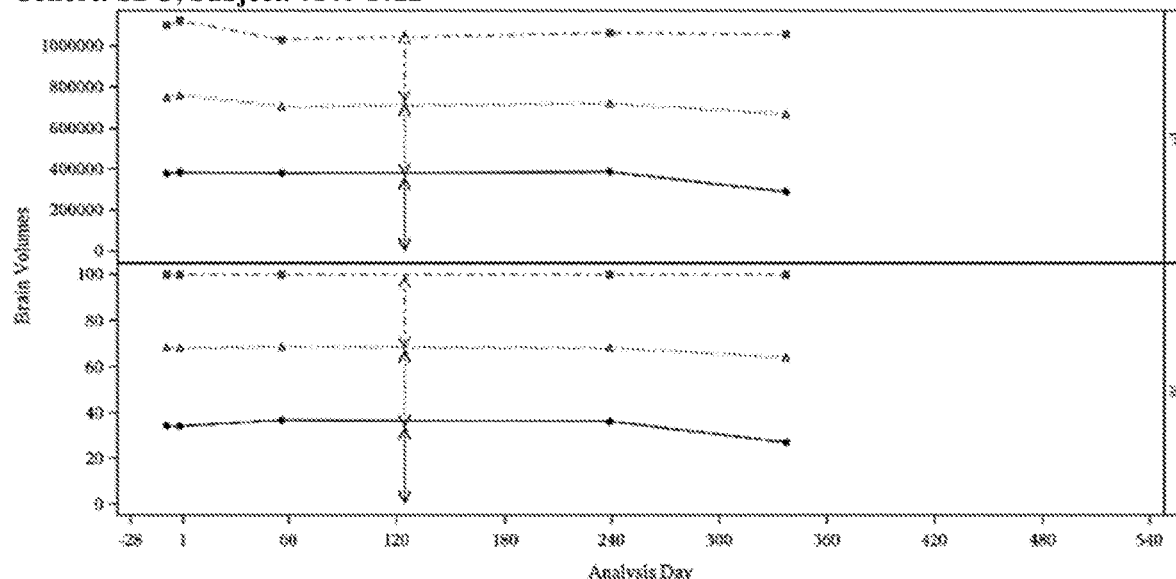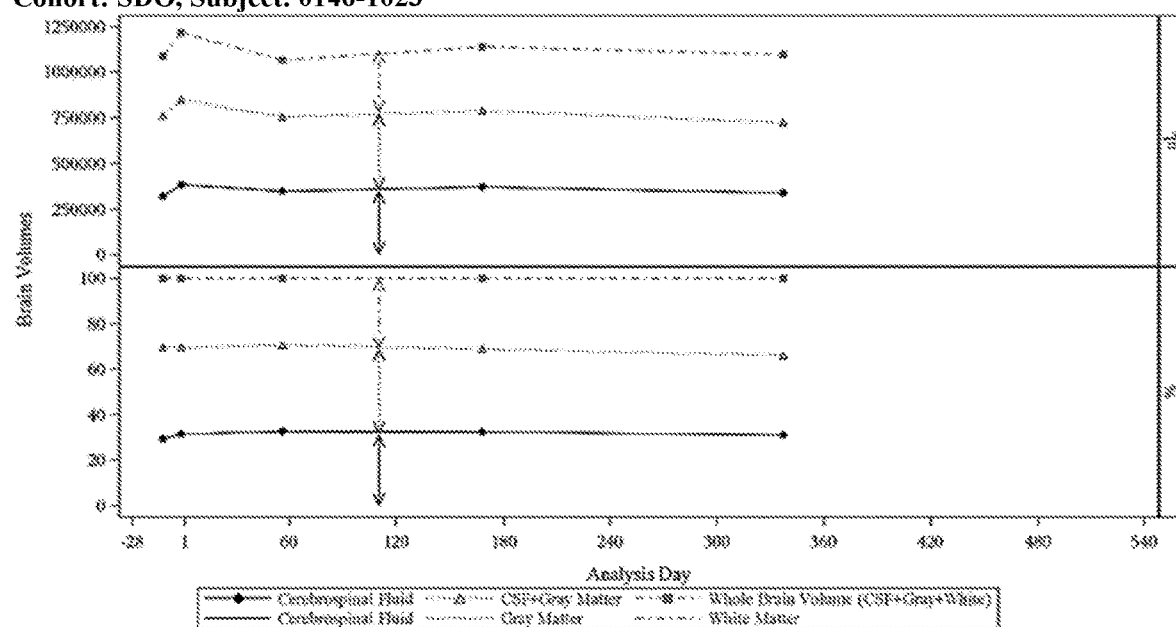
FIGURE 8G

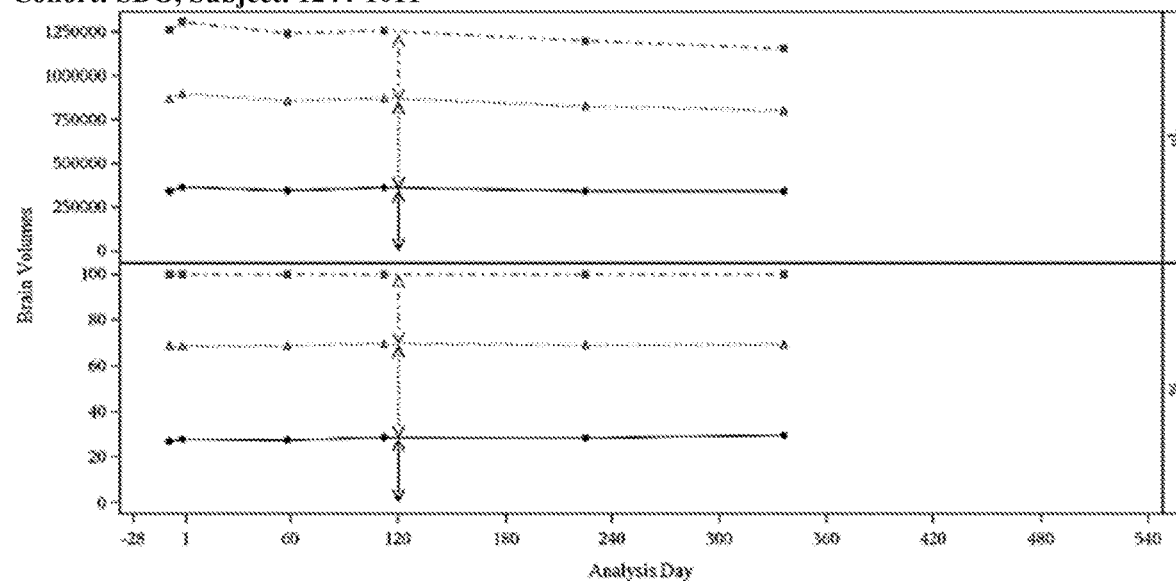
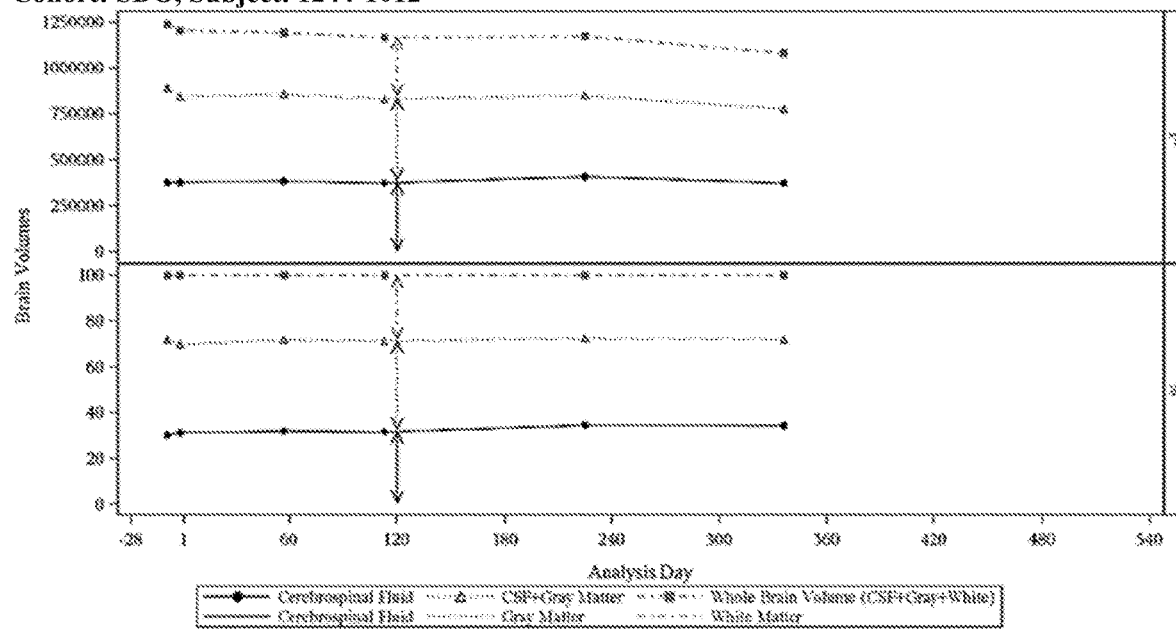
FIGURE 8H

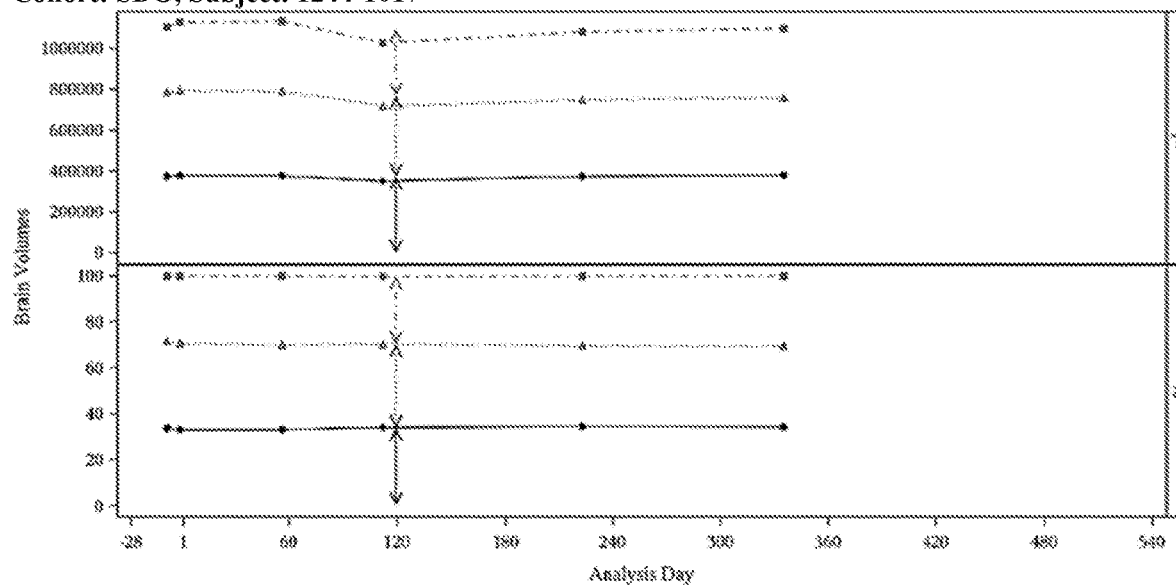
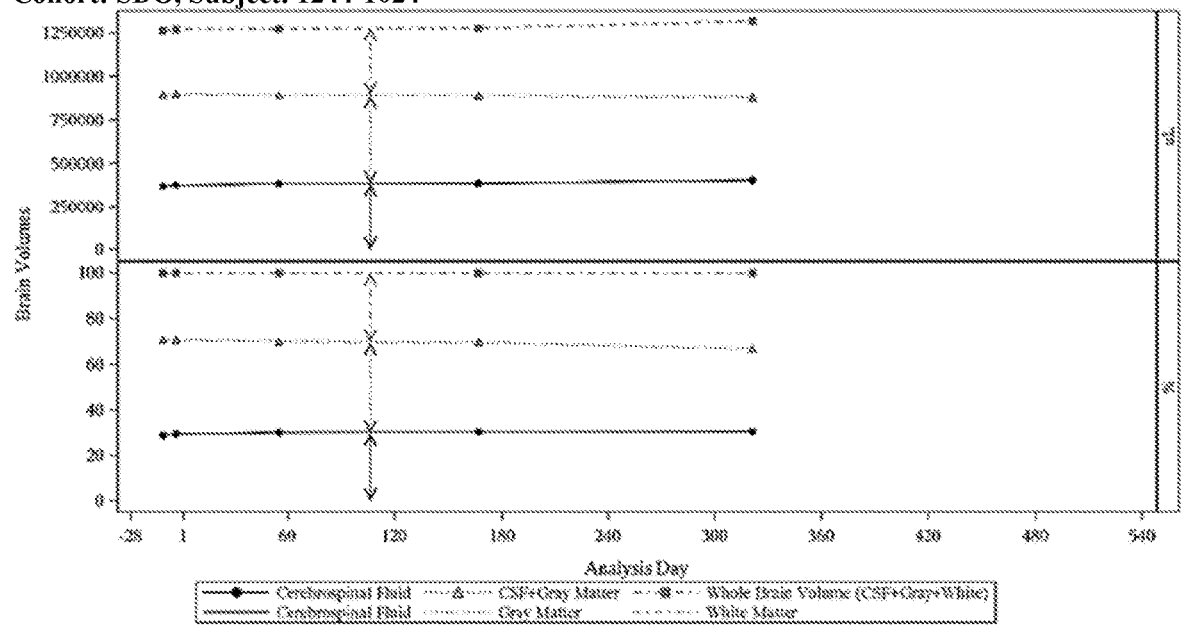
FIGURE 8I

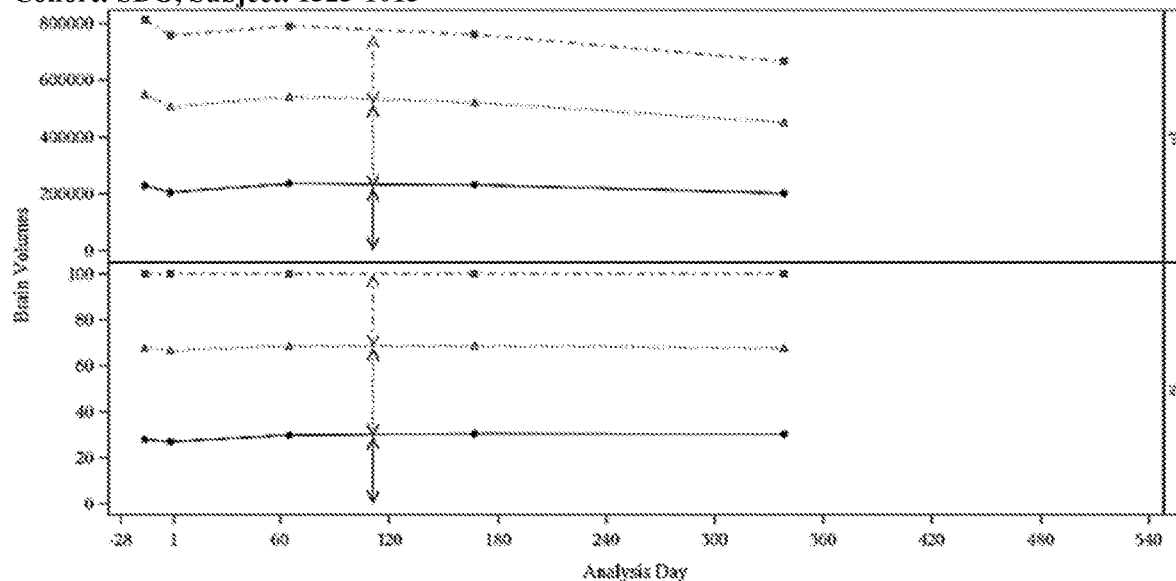
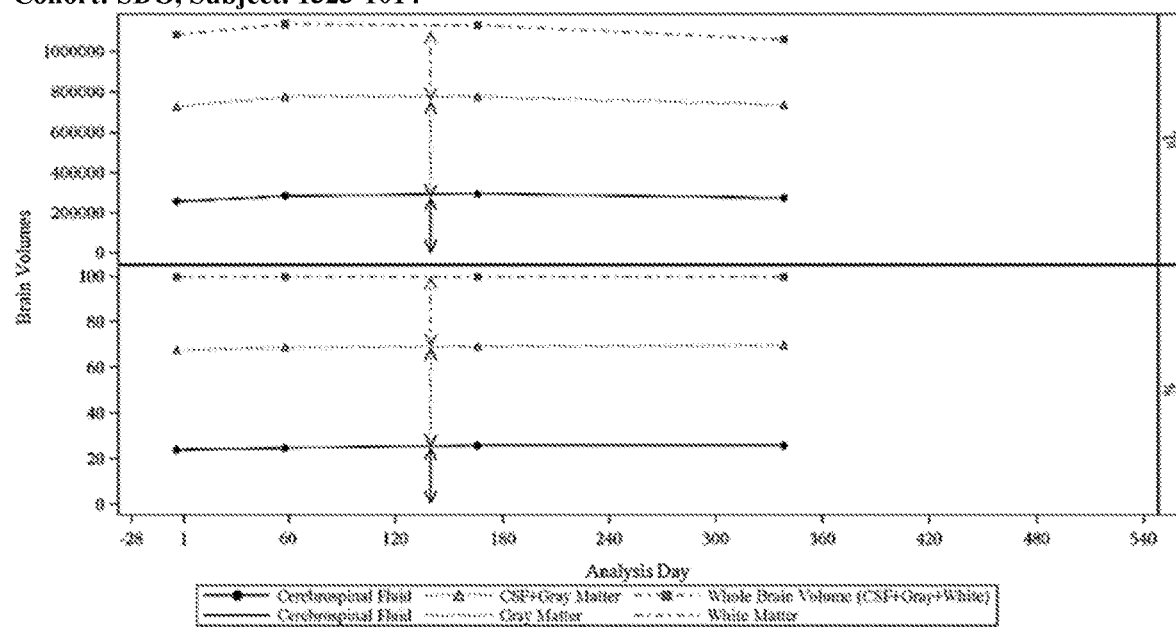
FIGURE 8J

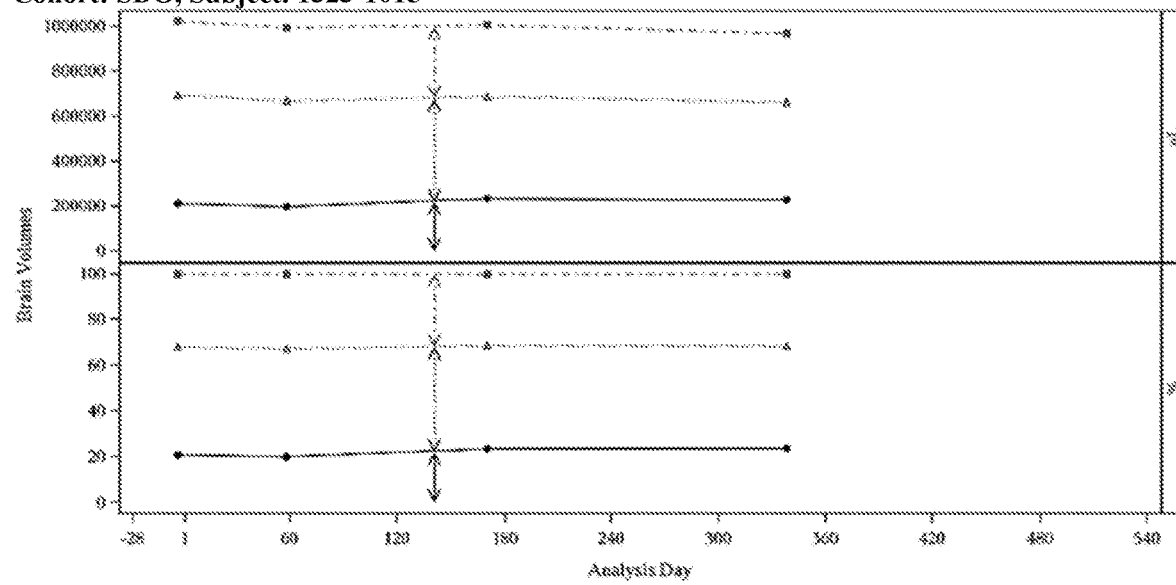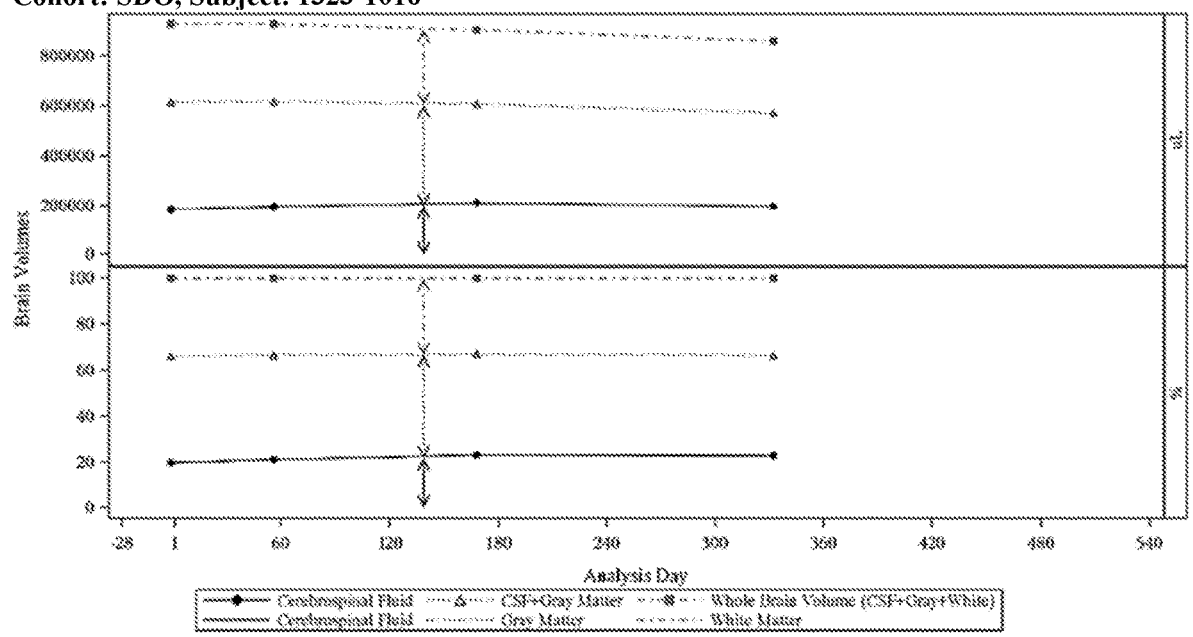
FIGURE 8K

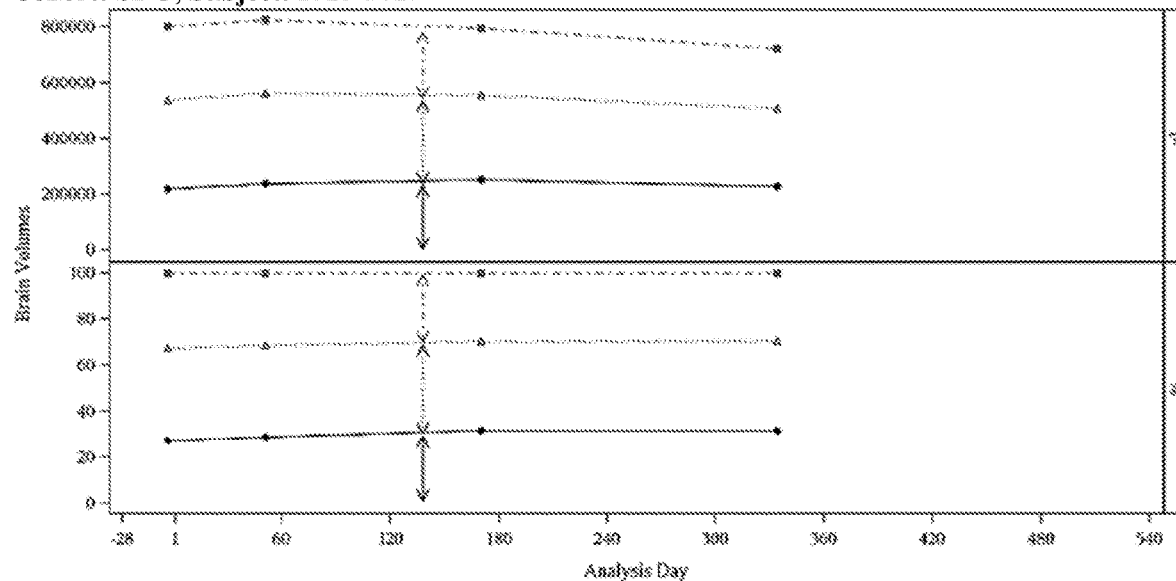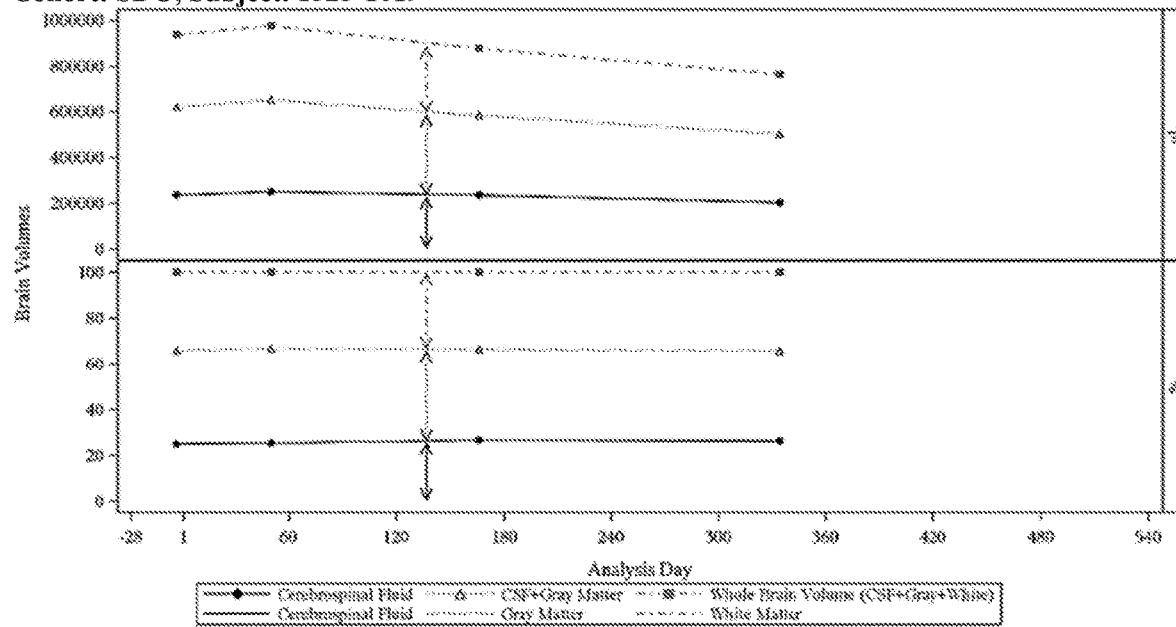
FIGURE 8L

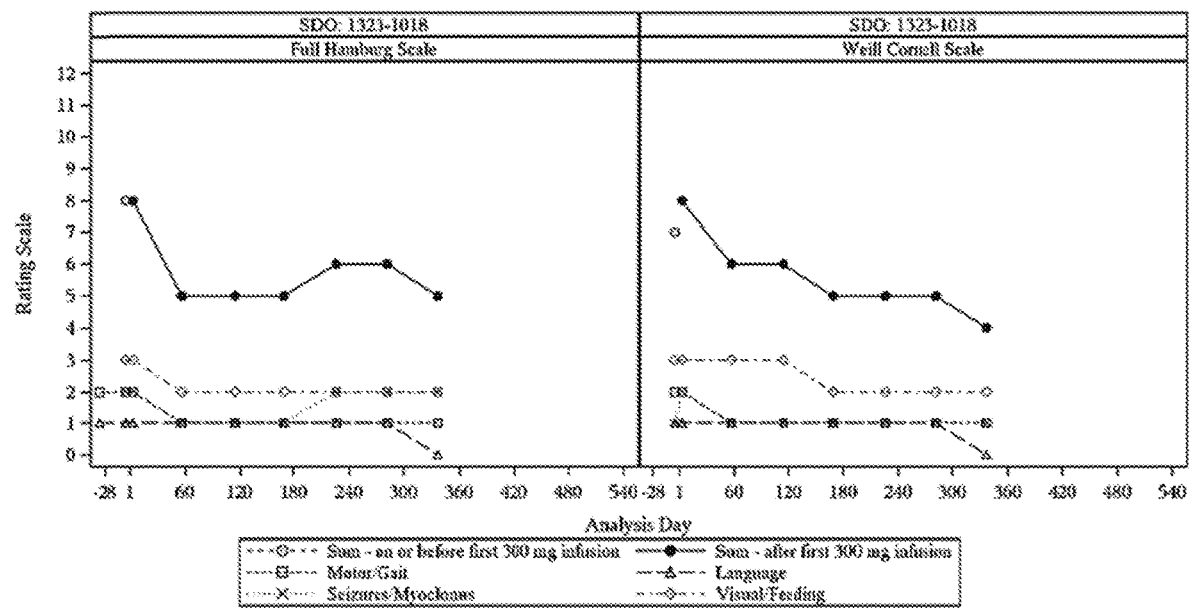
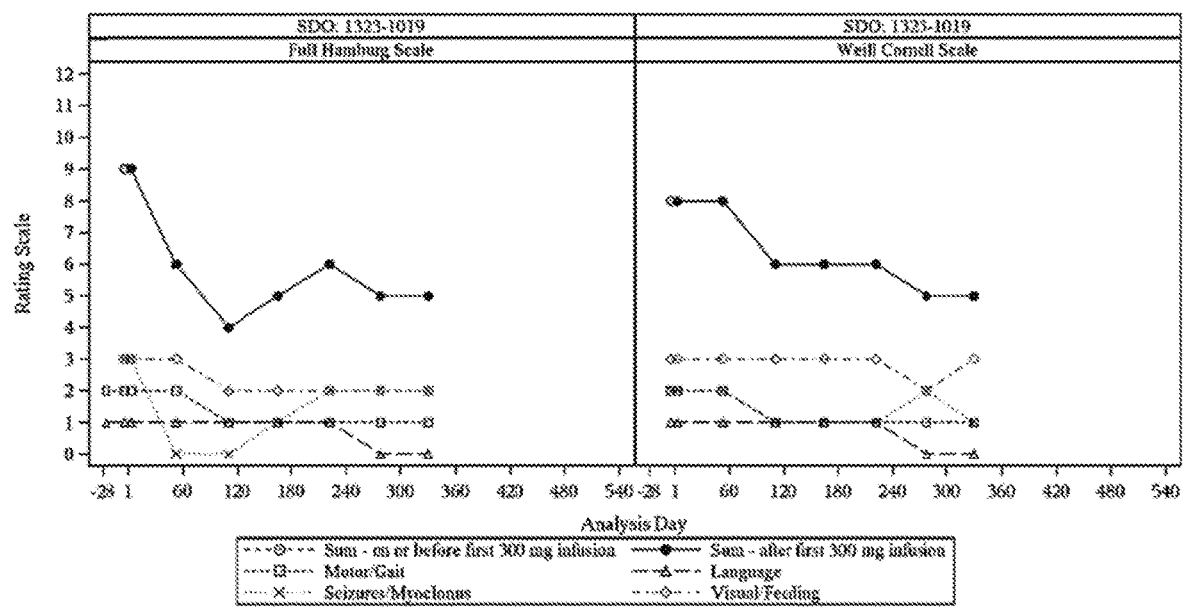
FIGURE 10L

TPP-1 FORMULATIONS AND METHODS FOR TREATING CLN2 DISEASE

CROSS-REFERENCE TO RELATED APPLICATIONS

This application is a Continuation of U.S. patent application Ser. No. 16/368,091, filed Mar. 28, 2019, which is a Continuation of U.S. patent application Ser. No. 15/147,485, filed May 5, 2016, now U.S. Pat. No. 10,279,015, issued on May 7, 2019, which claims the priority benefit under 35 U.S.C. § 119(e) of U.S. Provisional Patent Application No. 62/300,171, filed Feb. 26, 2016, and U.S. Provisional Patent Application No. 62/158,789, filed May 8, 2015, is hereby claimed, and the disclosure of each application is incorporated herein by reference in their entirety.

SEQUENCE LISTING

This application contains, as a separate part of the disclosure, a sequence listing in computer-readable form (49443B_Seqlisting.txt; Size: 8,307 bytes; created: Jul. 6, 2020), which is incorporated by reference in its entirety.

FIELD OF THE INVENTION

The present disclosure relates to formulations comprising recombinant human tripeptidyl peptidase-1 and their use in treating Neuronal Ceroid Lipofuscinosis disease and associated physiological symptoms.

BACKGROUND OF THE INVENTION

Neuronal Ceroid Lipofuscinosis (CLN2) disease is a rare genetic disease characterized by a deficiency of the lysosomal enzyme tripeptidyl peptidase-1 (TPP1) caused by mutations in the TPP1 gene. CLN2 disease is inherited as an autosomal recessive disorder, with an estimated incidence of 0.5 per 100,000 live births. In the absence of TPP1, lysosomal storage materials normally metabolized by the enzyme accumulate in many organs, and accumulation in the central nervous system leads to the neurodegenerative symptoms typical of CLN2 disease. The untreated disease progression of CLN2 disease has been well characterized, and the natural history of the disease is remarkably consistent and predictable, as demonstrated by natural history data from independent patient populations in North America and Europe.

CLN2 disease has a predominantly 'classic' late infantile phenotype. Children with CLN2 disease typically develop normally until about 3 years of age, when first symptoms emerge. Most commonly, CLN2 patients will have a first unprovoked seizure and begin to lag with acquiring normal language milestones. By age 3, all patients exhibit one or more signs of the disease, including for example, seizures, dementia, motor loss, movement disorder, blindness, clumsiness, ataxia and cognitive decline. From the onset of clinical symptoms, the course of the disease is rapid and aggressive, generally resulting in complete loss of language, cognition, gait, fine motor, bulbar function and vision within 2 to 4 years, rendering patients immobile, mute and blind. The patient remains in a vegetative state until death, which typically occurs between 6 and 12 years of age.

Two quantitative rating scales have been developed by expert clinicians in assessing the severity of CLN2 disease, and been employed in natural history studies: (1) the Hamburg scale (Steinfeld et al., *Am J Med Genet.* 2002; 112(4): 347-54); and (2) the Weill Cornell Medical College (WCMC) scale (Worgall et al., *Neurology.* 2007; 69(6):521-35). The structure and assessment methodology of the two scales is similar. Both scales measure the loss of previously attained important neurological milestones in CLN2 patients, with each unit lost in the disease rating scale representing a fundamental milestone in progressive decline.

Analysis of disease course in untreated CLN2-affected children shows that after the onset of disease, they predictably lose all language and gait in 3 years, with a loss of, on the average, 2.1 milestone events (i.e., 2.1 points lost in the disease rating scale) each year. Language decline usually precedes gait, such that the first year is characterized by loss of intelligible speech and progression to ataxic gait, the second year is characterized by loss of ambulation and intelligible language, and the third year is characterized by loss of any locomotion or communication.

Recombinant human tripeptidyl peptidase-1 (rhTPP1) is being developed as a possible treatment for CLN2 disease. The rhTPP1 protein (SEQ ID NO:1) is produced in cell culture as a zymogen (proenzyme), which does not have enzymatic activity. The proenzyme is auto-activated at acidic pH (and by lysosomal proteases) upon uptake to the lysosome. The mature native TPP1 protein is a lysosomal serine protease, and is the only known mammalian member of the sedolisin (serine-carboxyl peptidase) family characterized by a highly conserved Ser-Glu-Asp (SED) catalytic triad. The catalytic triad on rhTPP1 is formed by 5456, E253 and D341. The primary activity of the enzyme is as a tripeptidyl exopeptidase with a broad substrate specificity. Activity of the enzyme on its substrate leads to a sequential release of tripeptides from the N-terminus of the protein substrate (Oyama et al., *J Biochem.* 2005; 138(2):127-34). A secondary, significantly weaker endoproteolytic activity with a pH optimum of 3 has also been reported (Lin et al., *J Biol Chem.* 2001; 276(3):2249-55).

The only commercially available treatments for CLN2 are symptomatic and supportive; there are currently no approved therapeutic options to slow or halt the inexorable progression of CLN2, much less reverse the deleterious effects of the disease (Mole, S. E., and Williams, R. E., 2010, GeneReviews; Chang et al., in *The Neuronal Ceroid Lipofuscinoses (Batten Disease)*; 2011, Oxford Univ Press). Preservation of motor, language and/or vision capabilities for these children would be a clinically meaningful benefit for both patients and parents/caregivers. Thus, there is a need for new treatments for CLN2 which reduce or prevent deterioration of physiological functions associated with the disease.

SUMMARY OF THE INVENTION

The present disclosure is directed to formulations, kits, methods, and medical uses comprising recombinant human tripeptidyl peptidase-1 (rhTPP1) for treatment of Neuronal Ceroid Lipofuscinosis (CLN2) disease and the treatment or prevention of one or more physiological symptoms associated with onset of the disease. In one aspect, the disclosure provides a formulation comprising rhTPP1 for intracerebroventricular, intrathecal, or intraocular administration. Optionally, the rhTPP1 comprises the amino acid sequence of SEQ ID NO: 1 or SEQ ID NO:2, or a fragment thereof, for example, at a concentration of about 30 mg/mL in the formulation. The formulation may have a pH of about 6.5. The formulation may further comprise any of potassium chloride at a concentration of about 0.01 mg/mL to about 1 mg/mL, magnesium chloride hexahydrate at a concentration of about 0.01 mg/mL to about 1 mg/mL, calcium chloride dihydrate at a concentration of about 0.01 mg/mL to about 1 mg/mL, sodium phosphate dibasic heptahydrate at a concentration of about 0.01 mg/mL to about 1 mg/mL, sodium phosphate monobasic monohydrate at a concentration of about 0.01 mg/mL to about 1 mg/mL, sodium chloride at a concentration of about 1 mg/mL to about 20 mg/mL; or a combination of any or all of the foregoing. Optionally, the formulation is preservative-free and/or stable at about 5° C., e.g., for at least about 6 months. In one embodiment, the formulation comprises rhTPP1 at a concentration of about 30 mg/mL, sodium phosphate dibasic heptahydrate at a concentration of about 0.11 mg/mL, sodium phosphate monobasic monohydrate at a concentration of about 0.08 mg/mL, sodium chloride at a concentration of about 8.77 mg/mL, potassium chloride at a concentration of about 0.22 mg/mL, magnesium chloride hexahydrate at a concentration of about 0.16 mg/mL, and calcium chloride dihydrate at a concentration of about 0.21 mg/mL.

In another aspect, the disclosure provides a method of treating CLN2 disease, or one or more symptoms associated with CLN2 disease, comprising administering about 10 mL of a composition comprising a dose of about 300 mg of rhTPP1 to a subject in need thereof, wherein the composition is administered to the subject over a period of about 4 hours. The disclosure also provides a composition comprising rhTPP1 for use in treating CLN2 disease, or one or more symptoms associated with CLN2 disease in a subject, comprising about 10 mL of a composition comprising a dose of about 300 mg of rhTPP1, wherein the dose is to be administered to the subject over a period of about 4 hours. The disclosure also provides use of rhTPP1 in the manufacture of a medicament for treating CLN2 disease, or one or more symptoms associated with CLN2 disease, wherein the medicament comprises about 10 mL of a composition comprising a dose of about 300 mg of rhTPP1, wherein the dose is to be administered to the subject over a period of about 4 hours. In one aspect, the composition comprising rhTPP1 is administered to the subject via a catheter. Administration of the composition is optionally followed by flushing the catheter by administering a flushing solution in an amount up to about 5 mL, preferably in an amount of about 3 mL, more preferably in an amount of about 2 mL. The disclosure also provides a method of preventing or delaying the onset of one or more symptoms of CLN2 disease comprising administering about 10 mL of a composition comprising a dose of about 300 mg of rhTPP1 to a subject in need thereof, optionally wherein the subject has a family history of CNL2 disease and wherein the composition is administered to the subject over a period of about 4 hours. In one aspect, the composition comprising rhTPP1 is administered to the subject via a catheter. Administration of the composition is optionally followed by flushing the catheter by administering a flushing solution in an amount up to about 5 mL, preferably in an amount of about 3 mL, more preferably in an amount of about 2 mL. The composition may be administered intrathecally, intracerebroventricularly, and/or intraocularly, and is optionally administered every other week. Optionally, the composition is administered intracerebroventricularly or intrathecally and is administered without removal of cerebrospinal fluid from the subject just prior to administration of the composition comprising rhTPP1. In another embodiment, the composition may be administer in an isovolumetric fashion, i.e., with removal of a defined volume of CSF from the patient that is approximately equal to the volume of the composition intrathecally administered thereafter.

In one aspect, the disclosure provides a method of treating CLN2 disease, or one or more symptoms associated with the disease, comprising administering rhTPP1 to a subject in need thereof at a dose and/or frequency effective to maintain a physiological function or slow or reduce deterioration of a physiological function in the subject, wherein the physiological function is language function, motor function, vision or feeding function. The disclosure also provides a composition comprising rhTPP1 for use in treating CLN2 disease, or one or more symptoms associated with the disease, in a subject comprising a dose of rhTPP1 effective to maintain a physiological function or slow or reduce deterioration of a physiological function in the subject, wherein the physiological function is language function, motor function, vision or feeding function. The disclosure also provides use of rhTPP1 in the manufacture of a medicament for treating CLN2 disease, or one or more symptoms associated with the disease, wherein the medicament comprises a dose of rhTPP1 effective to maintain a physiological function or slow or reduce deterioration of a physiological function in the subject, wherein the physiological function is language function, motor function, vision or feeding function.

In another aspect, the disclosure provides a method of treating CLN2 disease in a subject, or one or more symptoms associated with the disease in a subject, comprising administering rhTPP1 to a subject in need thereof at a dose and/or frequency effective to improve physiological function in the subject, wherein the physiological function is language function, motor function, vision or feeding function. The disclosure also provides a composition comprising rhTPP1 for use in treating CLN2 disease, or one or more symptoms associated with the disease, in a subject comprising a dose of rhTPP1 effective to improve physiological function in the subject, wherein the physiological function is language function, motor function, vision or feeding function. The disclosure also provides use of rhTPP1 in the manufacture of a medicament for treating CLN2 disease, or one or more symptoms associated with the disease, wherein the medicament comprises a dose of rhTPP1 effective to improve physiological function in the subject, wherein the physiological function is language function, motor function, vision or feeding function. In another aspect, the disclosure provides a method of treating CLN2 disease in a subject, or one or more symptoms associated with the disease in a subject, comprising administering rhTPP1 to a subject in need thereof at a dose and/or frequency effective to prevent or treat a neurological symptom of the disease, wherein the neurological symptom is a decrease in brain volume, a decrease in gray matter in the brain, a seizure, or an increase in cranial cerebrospinal fluid. The disclosure also provides a composition comprising rhTPP1 for use in treating CLN2 disease, or one or more symptoms associated with the disease, in a subject comprising a dose of rhTPP1 effective to prevent or treat a neurological symptom of the disease, wherein the neurological symptom is a decrease in brain volume, a decrease in gray matter in the brain, a seizure, or an increase in cranial cerebrospinal fluid. The disclosure also provides use of rhTPP1 in the manufacture of a medicament for treating CLN2 disease, or one or more symptoms associated with the disease, wherein the medicament comprises a dose of rhTPP1 effective to prevent or treat a neurological symptom of the disease, wherein the neurological symptom is a decrease in brain volume, a decrease in gray matter in the brain, a seizure, or an increase in cranial cerebrospinal fluid. Optionally, the subject has a family history of CLN2 disease.

In another aspect, the disclosure provides a method of preventing or reducing CLN2-associated motor/gait deterioration in a subject comprising administering a therapeutically effective dose of rhTPP1 to the subject. The disclosure also provides a composition comprising a therapeutically effective dose of rhTPP1 for use in preventing or reducing CLN2-associated motor/gait deterioration in a subject. The disclosure also provides use of a therapeutically effective dose of rhTPP1 for the manufacture of a medicament for preventing or reducing CLN2-associated motor/gait deterioration in a subject. In one aspect, the method comprises administering a dose of rhTPP1 effective to prevent or reduce a decline in the subject's clinical disease rating compared to a previous rating determined before or during treatment, for example, as measured using a WCMC disease rating scale for gait or a Hamburg disease rating scale for motor.

In another aspect, the disclosure provides a method of preventing or reducing CLN2-associated language deterioration in a subject comprising administering a therapeutically effective dose of rhTPP1 to the subject. The disclosure also provides a composition comprising a therapeutically effective dose of rhTPP1 for use in preventing or reducing CLN2-associated language deterioration in a subject. The disclosure also provides use of a therapeutically effective dose of rhTPP1 for the manufacture of a medicament for preventing or reducing CLN2-associated language deterioration in a subject. In one aspect, the method comprises administering a dose of rhTPP1 effective to prevent or reduce a decline in the subject's clinical disease rating compared to a previous rating determined before or during treatment, for example, as measured using a WCMC or Hamburg disease rating scale for language.

In another aspect, the disclosure provides a method of preventing or reducing CLN2-associated vision deterioration in a subject comprising administering a therapeutically effective dose of rhTPP1 to the subject. The disclosure also provides a composition comprising a therapeutically effective dose of rhTPP1 for use in preventing or reducing CLN2-associated vision deterioration in a subject. The disclosure also provides use of a therapeutically effective dose of rhTPP1 for the manufacture of a medicament for preventing or reducing CLN2-associated vision deterioration in a subject. In one aspect, the method comprises administering a dose of rhTPP1 effective to prevent or reduce a decline in the subject's clinical disease rating compared to a previous rating determined before or during treatment, for example, as measured using a Hamburg disease rating scale for visual function.

In another aspect, the disclosure provides a method of preventing or reducing CLN2-associated brain volume deterioration in a subject comprising administering a therapeutically effective dose of rhTPP1 to the subject. The disclosure also provides a composition comprising a therapeutically effective dose of rhTPP1 for use in preventing or reducing CLN2-associated brain volume deterioration in a subject. The disclosure also provides use of a therapeutically effective dose of rhTPP1 for the manufacture of a medicament for preventing or reducing CLN2-associated brain volume deterioration in a subject. In one aspect, the method comprises administering a dose of rhTPP1 effective to prevent or reduce a decrease in brain volume and/or a decrease in gray matter volume compared to a previous volume determined before or during treatment.

In one aspect, the disclosure provides a kit comprising a formulation comprising rhTPP1 described herein and a flushing solution. The flushing solution may comprise any of the formulations of the disclosure, with the rhTPP1 omitted. For example, the flushing solution may comprise sodium phosphate dibasic heptahydrate at a concentration of about 0.11 mg/mL, sodium phosphate monobasic monohydrate at a concentration of about 0.08 mg/mL, sodium chloride at a concentration of about 8.77 mg/mL, potassium chloride at a concentration of about 0.22 mg/mL, magnesium chloride hexahydrate at a concentration of about 0.16 mg/mL, and calcium chloride dihydrate at a concentration of about 0.21 mg/mL. Optionally, the kit further comprises a reservoir for implantation and a catheter. Optionally, the kit may comprise one or more elements selected from the group consisting of an extension line, an in-line filter, a port needle, at least one (optionally two) syringe(s), at least one (optionally two) syringe needle(s), and combinations thereof.

The foregoing summary is not intended to define every aspect of the invention, and other features and advantages of the present disclosure will become apparent from the following detailed description, including the drawings. The present disclosure is intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the invention narrower in scope in any way than the variations specifically mentioned above. With respect to aspects of the disclosure described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature. Additional features and variations of the disclosure will be apparent to those skilled in the art from the entirety of this application, and all such features are intended as aspects of the disclosure.

BRIEF DESCRIPTION OF THE DRAWINGS

FIG. 1 depicts the amino acid sequence of rhTPP1 zymogen, lacking the associated signal peptide. The pro-segment of the enzyme is the first 176 amino acid residues, and the mature enzyme is 368 amino acids in length starting from position 177 (SEQ ID NO:1).

FIGS. 8A to 8L depict the brain volume of 24 treated patients. The volumes (top panel) and proportions (bottom panel) of white matter are shown as the difference between whole brain volume (dash-dot line) and CSF and gray matter (dashed line) and of gray matter as the difference between CSF and gray matter (dashed line) and CSF (solid line).

FIG. 9A depicts the CLN2 score for 23 patients treated with 300 mg rhTPP1 for 48 weeks (dashed line) and an untreated natural history cohort of 41 subjects (solid line). FIG. 9B depicts the change in CLN2 score from baseline for 23 patients treated with 300 mg rhTPP1 for 48 weeks.

FIGS. 10A to 10L depict the clinical assessments of 24 patients accrued over the treatment duration and show the 0 to 12 combined Hamburg (left panel) motor (squares), language (triangles), seizures (crosses), and visual composite score (diamonds) and the 0 to 12 combined WCMC (right panel) gait (squares), language (triangles), myoclonus (crosses), and feeding (diamonds) composite score. Open circles represent aggregate CLN2 scores obtained on or before the first 300 mg infusion of rhTPP1, while closed circles represent aggregate CLN2 scores obtained after the first 300 mg infusion of rhTPP1.

DETAILED DESCRIPTION OF THE INVENTION

Figure 2:
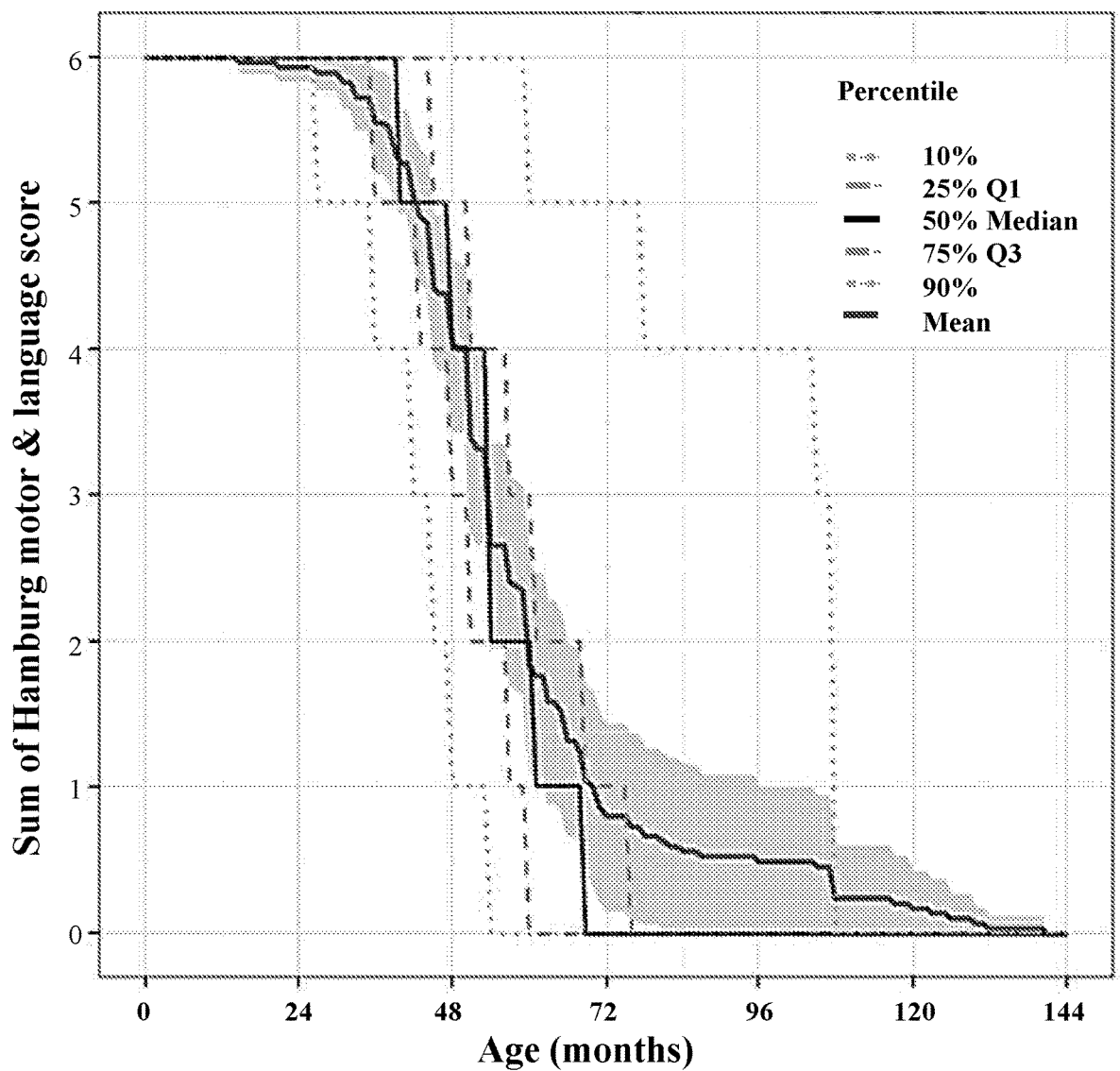
FIG. 2 depicts the clinical progression of untreated subjects having CLN2 disease in the natural history study and shows the 0 to 6 Hamburg motor and language composite score as a function of patient age. The median, quartile and 10%/90% distributions; in addition to the mean and 95% confidence interval, are shown.
Figure 3A:
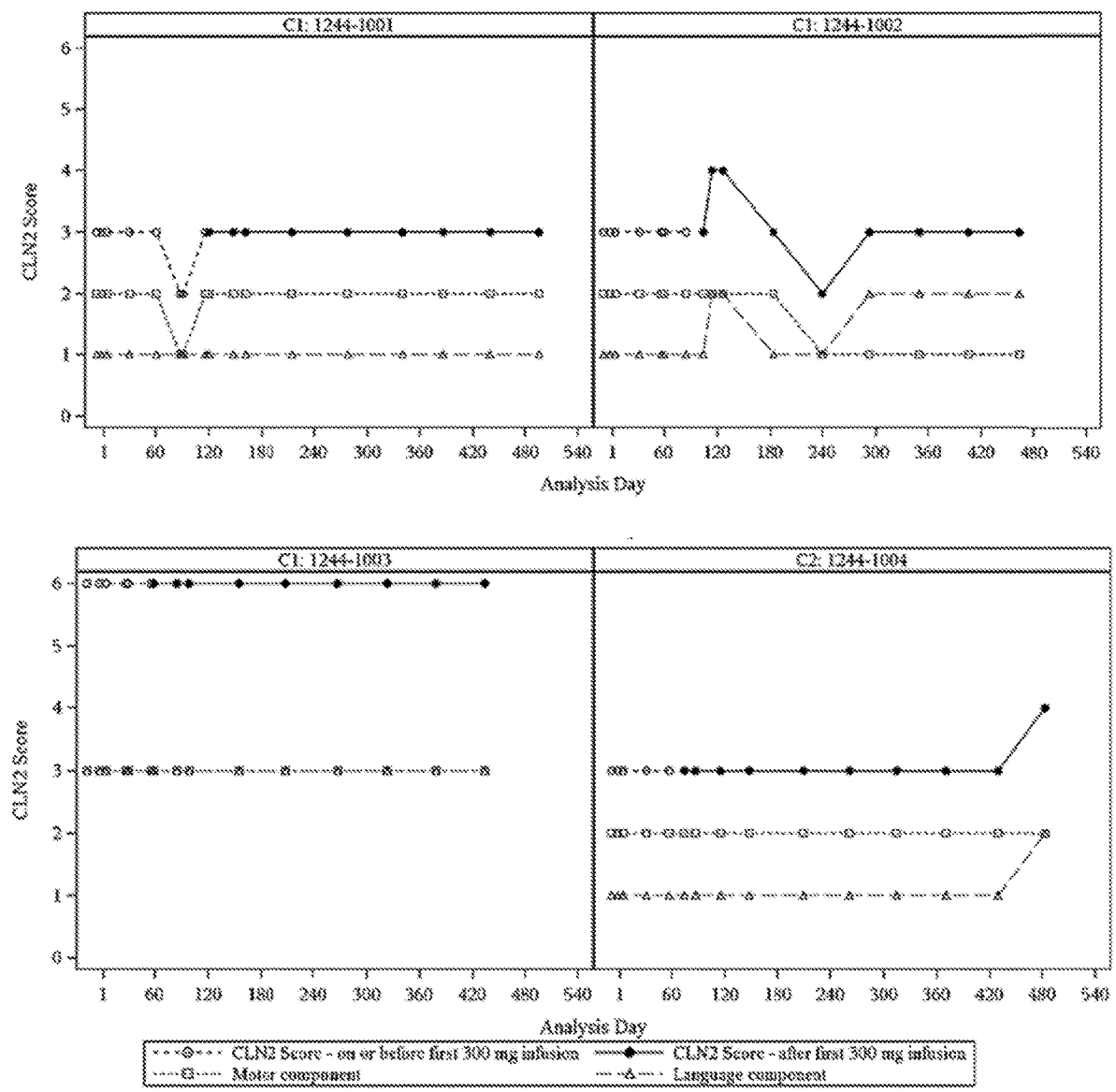
FIGS. 3A to 3F depict the clinical assessments of 24 patients accrued over the treatment duration and show the 0 to 6 Hamburg motor and language composite score. Open circles represent CLN2 scores obtained on or before the first 300 mg infusion of rhTPP1, while closed circles represent CLN2 scores obtained after the first 300 mg infusion of rhTPP1. Both the aggregate score (circles) and the contribution of motor/gait (squares) and language (triangles) to the aggregate score are shown. Analysis Day 1 is the date of the first infusion.
Figure 3B:
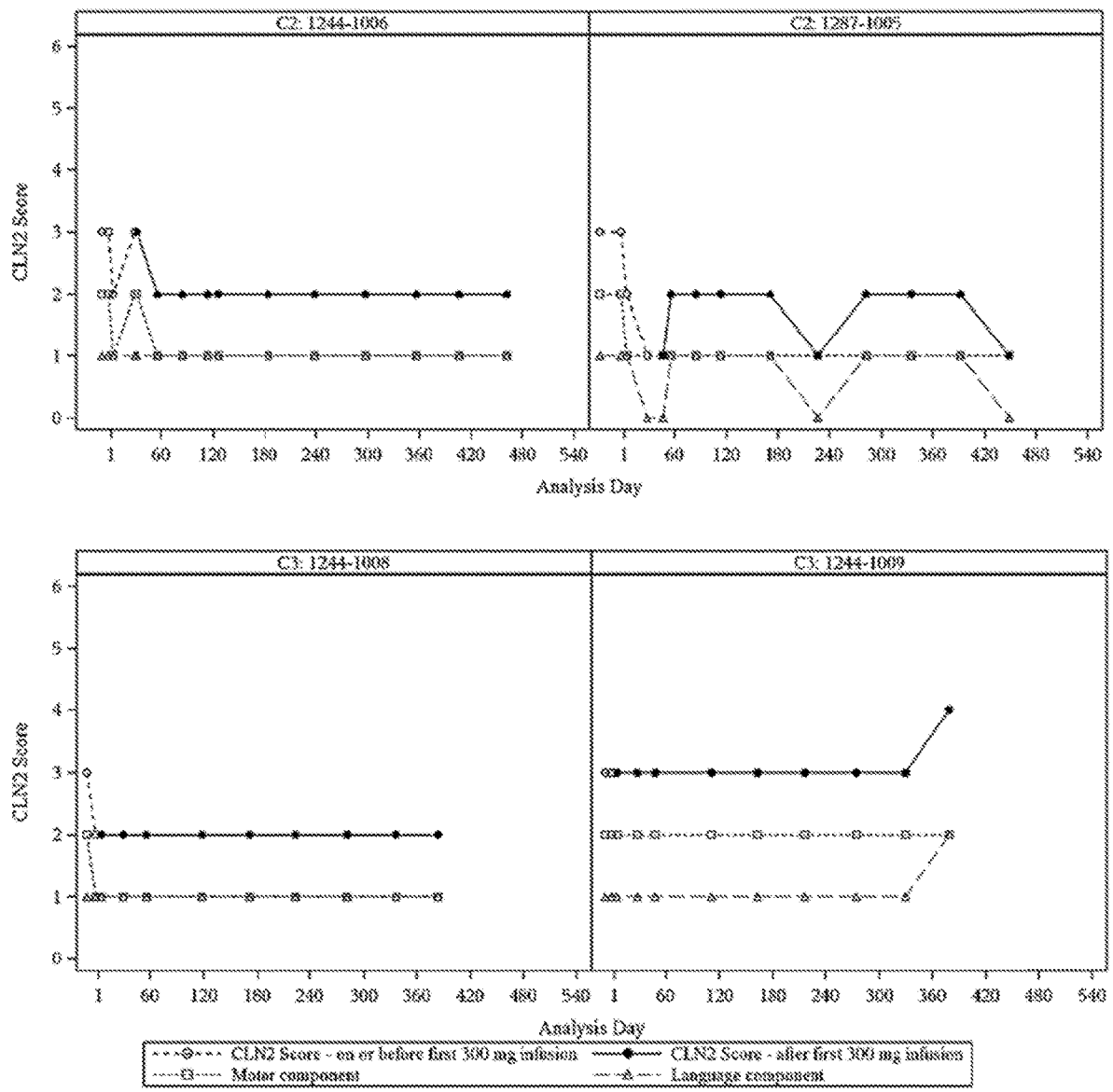
Figure 3C:
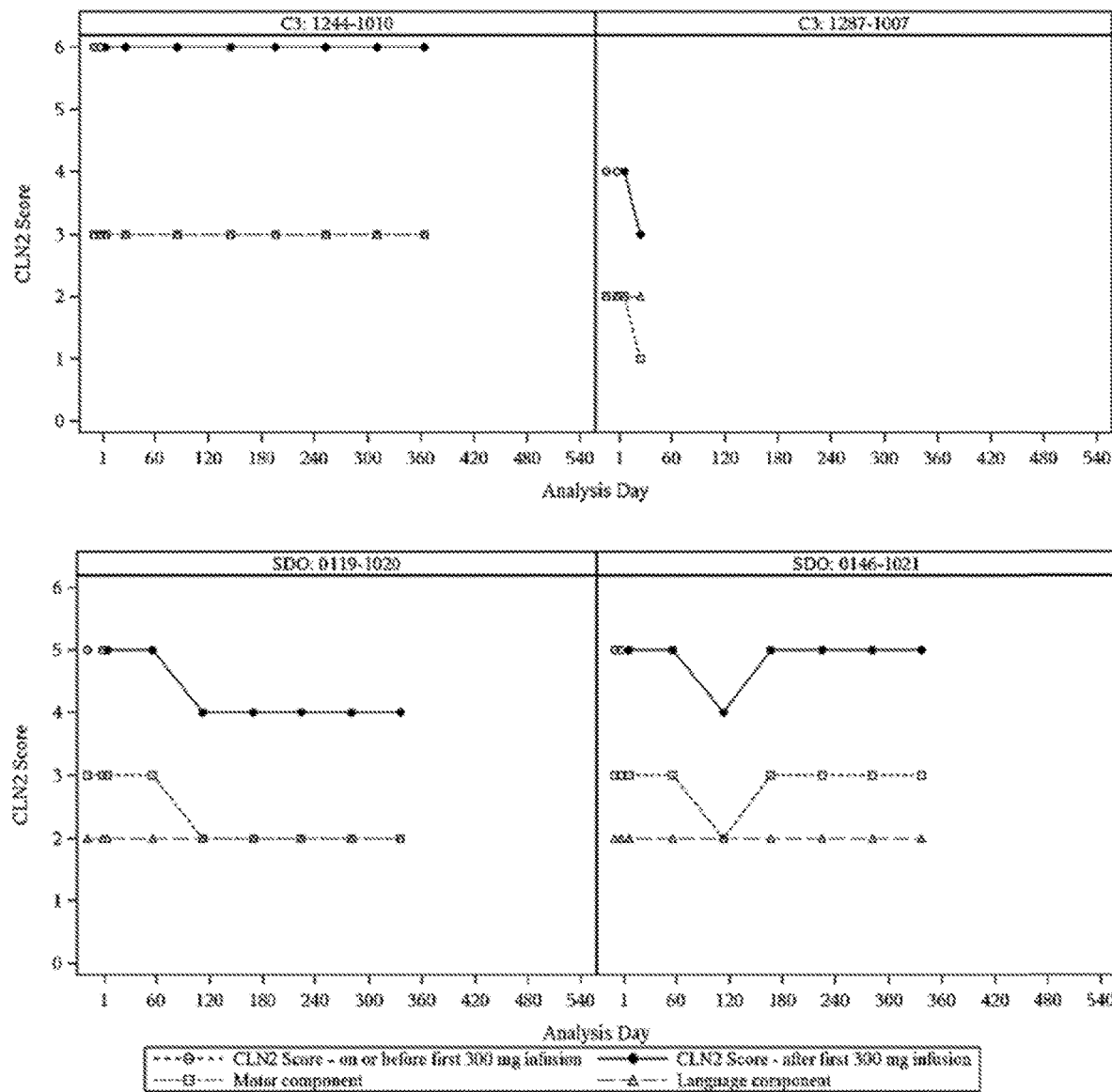
Figure 3D:
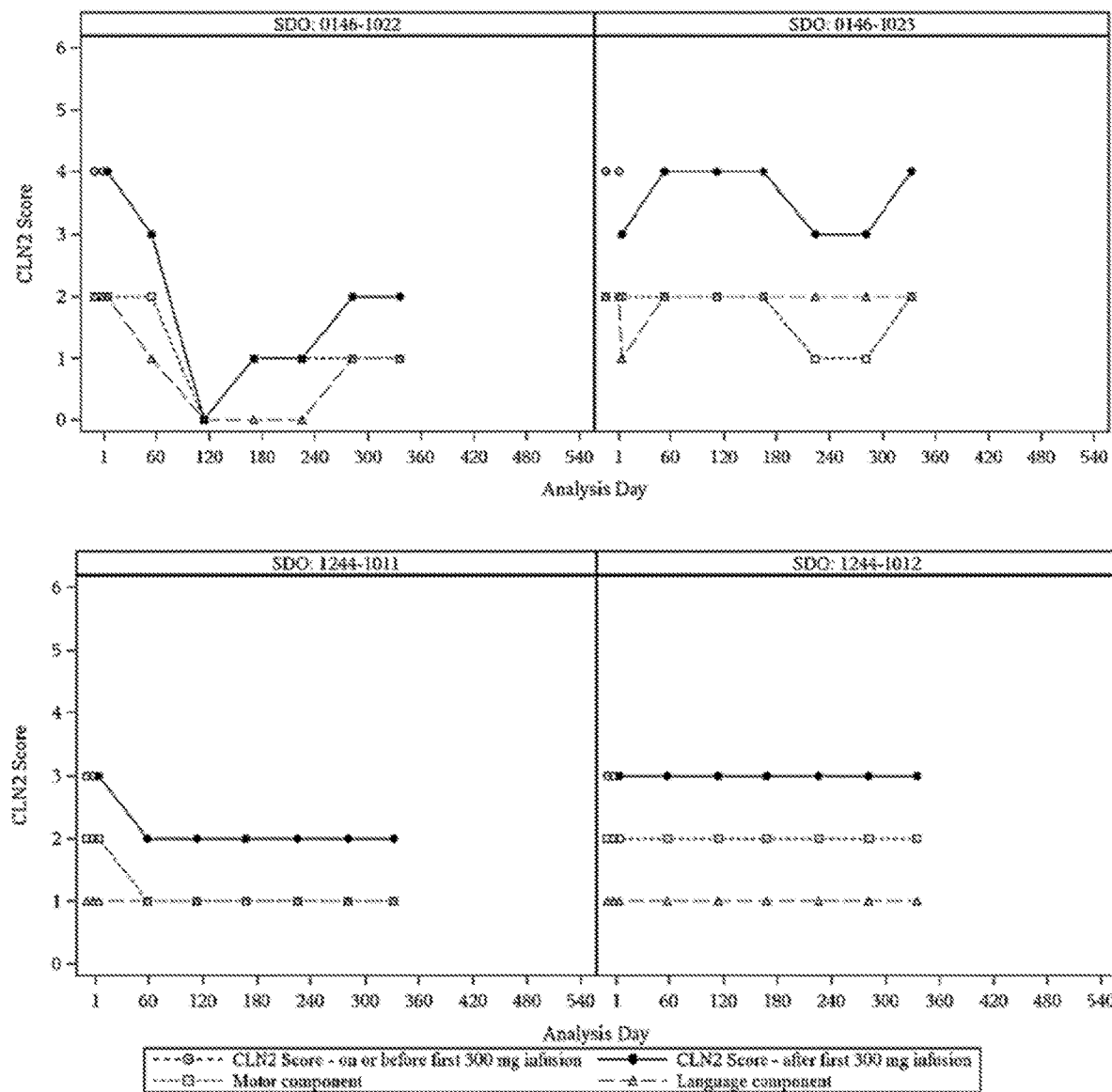
Figure 3E:
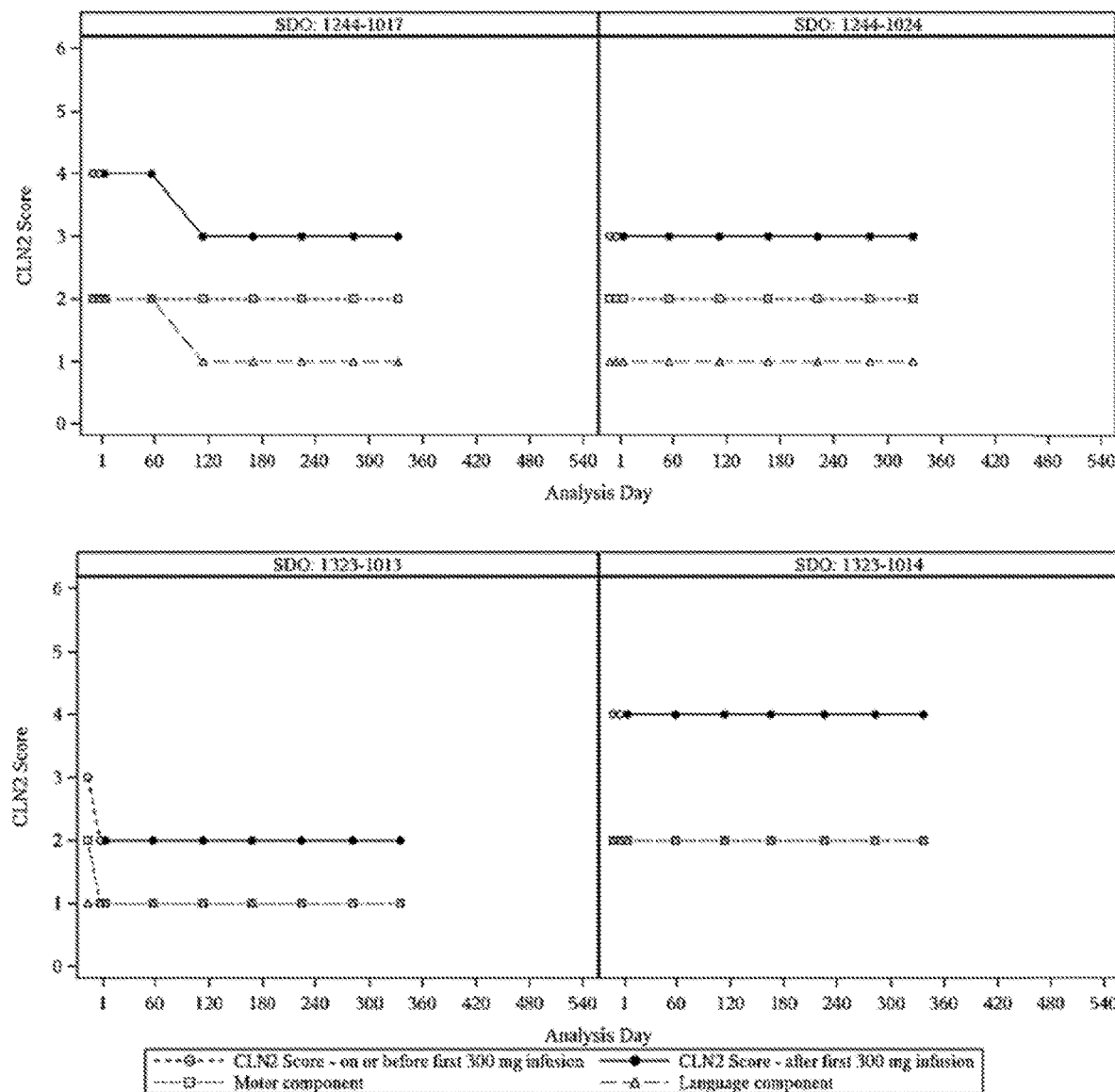
Figure 3F:
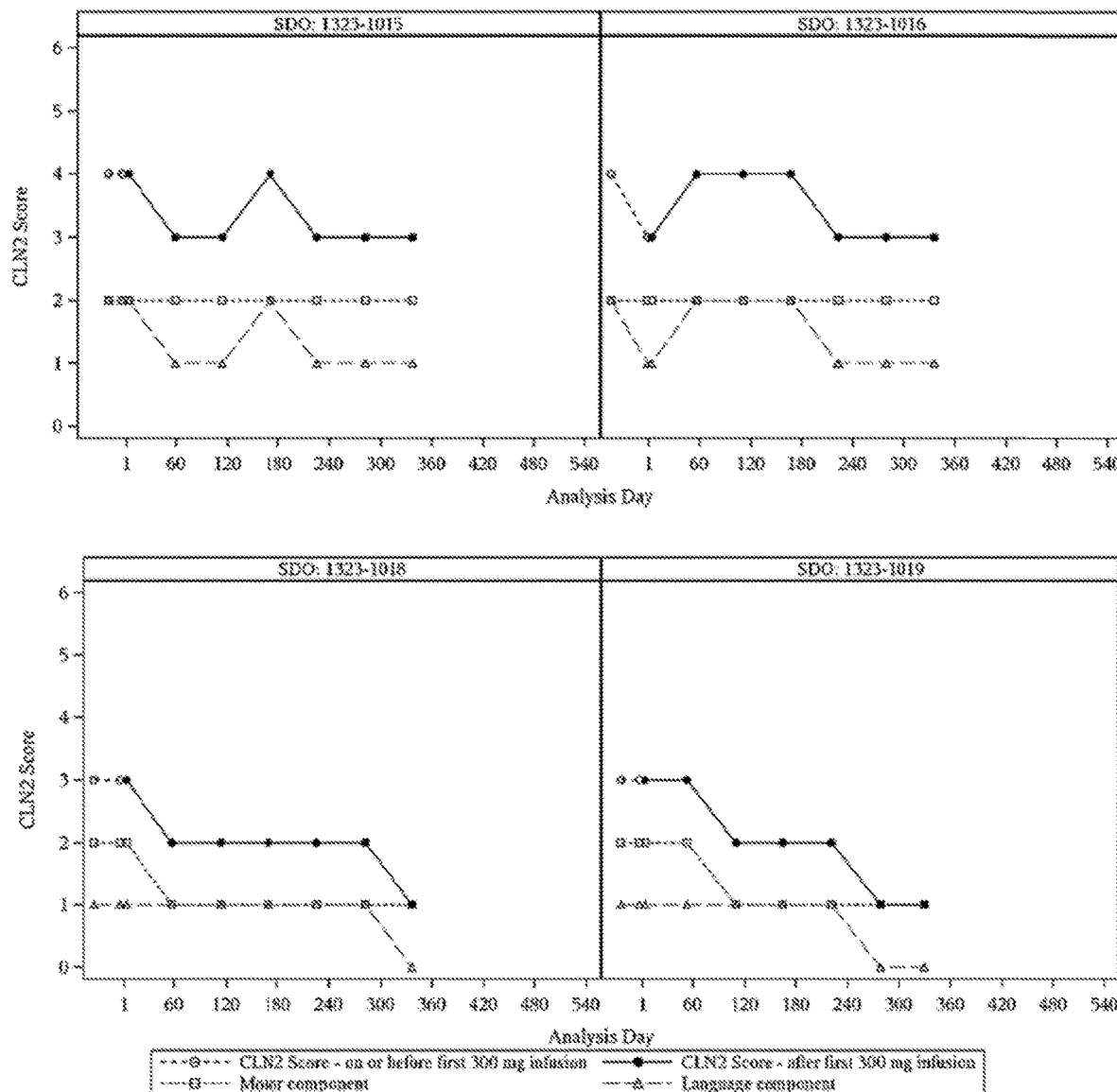

The following definitions may be useful in aiding the skilled practitioner in understanding the disclosure. Unless otherwise defined herein, scientific and technical terms used in the present disclosure shall have the meanings that are commonly understood by those of ordinary skill in the art. Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range.

The term "family history" refers to a subject having a blood relative diagnosed with CLN2 disease, e.g., a sibling, parent, grandparent, great-grandparent, etc.

The term "fragment" refers, in one aspect, to a recombinant protein comprising a portion of the rhTPP1 proenzyme amino acid sequence set forth in SEQ ID NO:1 and FIG. 1. For example, a fragment may contain at least about 60%, at least about 70%, at least about 80%, at least about 90%, or at least about 95% of the amino acid sequence set forth in SEQ ID NO:1. In another aspect, a fragment may comprise the full-length (368 amino acids long; amino acids 177-544 of SEQ ID NO:1) mature TPP1 enzyme amino acid sequence set forth in SEQ ID NO:2, a portion thereof, and/or at least the catalytic triad formed by the amino acid residues S456, E253, and D341. A fragment retains catalytic activity. For example, a fragment exhibits tripeptidyl exopeptidase activity and/or exhibits catalytic activity that results in the sequential release of tripeptides from the N-terminus of a protein substrate. In certain aspects, a "fragment" of the rhTPP1 proenzyme comprises at least 500 consecutive amino acids of SEQ ID NO:1, at least 450 consecutive amino acids of SEQ ID NO:1, at least 400 consecutive amino acids of SEQ ID NO:1, at least 368 amino acids of SEQ ID NO:1, at least 350 amino acids of SEQ ID NO:1 or at least 300 consecutive amino acids of SEQ ID NO:1. In other aspects, a "fragment" of the rhTPP1 proenzyme comprises at least 350 consecutive amino acids of SEQ ID NO:2, at least 325 consecutive amino acids of SEQ ID NO:2, at least 300 consecutive amino acids of SEQ ID NO:2, at least 275 consecutive amino acids of SEQ ID NO:2, at least 250 consecutive amino acids of SEQ ID NO:2 or at least 200 consecutive amino acids of SEQ ID NO:2.

The term "intracerebroventricular" refers to administration of a composition into the ventricular system of the brain, e.g., via injection, infusion, or implantation (for example, into a ventricle of the brain).

The term "intraocular" refers to the administration of a composition to the eye region, e.g., via injection, infusion, or implantation (for example, into the eyeball) or topical/ophthalmic administration (for example, using a cream, ointment, gel or liquid drops).

The term "intrathecal" refers to administration of a composition into the lumbar region, e.g., via injection, infusion, or implantation (for example, into the subarachnoid space of the spinal cord).

The term "therapeutically effective" refers to any therapeutic benefit that arises as a result of the treatment methods of the present invention. For example, such an effect can be the beneficial effects that manifest in an appropriate target tissue or organ, where such beneficial physiological effect is compared to that physiological parameter being measured in the absence of the enzyme replacement therapy. Such a therapeutic effect may be any reduction or elimination of one or more clinical or subclinical manifestations of CLN2 disease. For example, a therapeutically effective treatment improves, reverses, delays, prevents, or reduces deterioration of one or more physiological function and/or neurological symptom of CLN2 as described herein.

The term "stable" or "stabilized" refers to a protein-containing formulation in which the protein component therein essentially retains its physical, functional and/or chemical stability upon storage over time. Stability can be measured at a selected temperature for a selected time period. Preferably, the formulation is stable at room temperature (about 30° C.) or at about 40° C. for at least 1 month and/or stable at about 2° C. to about 8° C. for at least 1 year and preferably for at least 2 years. For example, the extent of protein degradation or aggregation during storage can be used as an indicator of protein stability. Thus, a "stable" formulation may be one wherein less than about 20%, more preferably less than about 10%, and most preferably less than about 5% of the protein component is present in a degraded or aggregated form in the formulation following storage. "Stable" formulations retain essentially the same functional or therapeutic characteristics of the newly prepared formulation. Various analytical techniques for measuring protein stability are available in the art and are reviewed, for example, in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993).

The term "prevents" or "reduces" or grammatical equivalents thereof when used in reference to the prevention or reduction of one or more symptoms or physiological consequences of CLN2 disease in a subject means that the rate of decline of that/those symptom(s) in the treated CLN2 subject is slower than that observed in an untreated CLN2 subject. In this regard, the untreated CLN2 may be the same subject that is subsequently treated with a composition of the present invention or may be the average rate of decline of the symptom(s) of interest as observed from the natural history study results disclosed herein.

In jurisdictions that forbid the patenting of methods that are practiced on the human body, the meaning of "administering" rhTPP1 or a formulation thereof to a human subject refers to medical uses for rhTPP1 or a formulation thereof, for example, rhTPP1 or a formulation thereof for use in treating CLN2 disease as described herein or use of rhTPP1 for the manufacture of a medicament for treating CLN2 disease as described herein. The broadest reasonable interpretation that is consistent with laws or regulations defining patentable subject matter is intended. In jurisdictions that do not forbid the patenting of methods that are practiced on the human body, "administering" rhTPP1 or a formulation thereof includes both methods practiced on the human body and also the foregoing activities.

The present disclosure provides formulations and kits comprising rhTPP1, and methods of using the same to treat CLN2 disease. Administration of rhTPP1 allows for cellular uptake of the protein by the cation independent mannose 6 phosphate receptor (CI-MPR) and localization to the lysosomes in cells throughout the central nervous system. The enzyme uptake into the lysosomes and subsequent activation promotes increased catabolism of storage material in affected tissues, reduces the progressive accumulation of the lysosomal storage material, and arrests decline of the disease. The formulations and methods of the disclosure provide therapeutic benefits that surpass those of currently approved treatments.

Formulations

The disclosure provides formulations comprising rhTPP1 for intracerebroventricular, intrathecal, and/or intraocular administration. In one aspect, the rhTPP1 comprises SEQ ID NO:1 or a fragment thereof. RhTPP1 proteins suitable for use in the formulations and methods described herein, and methods of obtaining the rhTPP1 proteins, are described in U.S. Pat. Nos. 6,302,685 and 8,277,800 incorporated herein by reference in their entirety.

In one aspect, the rhTPP1 comprises the amino acid sequence of SEQ ID NO:1 (amino acids 1-544 of the amino acid sequence shown in FIG. 1) or a fragment thereof possessing catalytic activity. In another aspect, the rhTPP1 comprises the amino acid sequence of SEQ ID NO:2 (amino acids 177-544 of the amino acid sequence shown in FIG. 1) or a fragment thereof possessing catalytic activity. In still another aspect, the rhTPP1 has detectable enzyme activity or is processed in vivo to a form of the enzyme that has detectable enzyme activity (i.e., is "functional") and has at least about 70% sequence identity with SEQ ID NO:1 or SEQ ID NO:2. For example, the functional rhTPP1 is at least about 70% identical, at least about 75% identical, at least about 80% identical, at least about 85% identical, at least about 90% identical, at least about 95% identical, or at least about 97% identical, to SEQ ID NO:1 or SEQ ID NO:2. In one aspect, the formulation is a liquid formulation that comprises rhTPP1 at a concentration of about 1 mg/mL to about 100 mg/mL, for example, about 10 mg/mL to about 50 mg/mL, about 25 mg/mL to about 40 mg/mL, or about 30 mg/mL to about 60 mg/mL. In various aspects, the formulation comprises rhTPP1 at a concentration of from about 1 mg/mL to about 100 mg/mL, from about 5 mg/mL to about 80 mg/mL, from about 10 mg/mL to about 50 mg/mL, from about 20 mg/mL to about 40 mg/mL, from about 25 mg/mL to about 35 mg/mL, more specifically about 1 mg/mL, about 10 mg/ml, about 20 mg/mL, about 30 mg/mL, about 40 mg/mL, about 50 mg/mL, about 60 mg/mL, about 70 mg/mL, about 80 mg/mL, about 90 mg/mL, or about 100 mg/mL. In one aspect, the formulation has a pH of about 5.5 to about 7.5 or about 6.0 to about 7.0, for example, about 5.5, about 6.0, about 6.5, about 7.0, or about 7.5.

In one aspect, a formulation comprising rhTPP1 of the disclosure further comprises one or more excipients that maintains the level of a key electrolyte in the cerebrospinal fluid (CSF) or ocular fluid. For example, in one aspect, in addition to the rhTPP1 or fragment thereof, the formulation further comprises potassium chloride at a concentration of about 0.01 mg/mL to about 1 mg/mL, for example, about 0.1 mg/mL to about 0.5 mg/mL, about 0.2 mg/mL to about 0.8 mg/mL, about 0.2 mg/mL to about 0.4 mg/mL, about 0.15 mg/mL to about 0.25 mg/mL, or about 0.05 mg/mL to about 0.3 mg/mL. In another aspect, the formulation further comprises magnesium chloride hexahydrate at a concentration of about 0.01 mg/mL to about 1 mg/mL, for example, about 0.1 mg/mL to about 0.5 mg/mL, about 0.1 mg/mL to about 0.8 mg/mL, about 0.1 mg/mL to about 0.3 mg/mL, about 0.15 mg/mL to about 0.25 mg/mL, or about 0.05 mg/mL to about 0.3 mg/mL. In another aspect, the formulation further comprises calcium chloride dihydrate at a concentration of about 0.01 mg/mL to about 1 mg/mL, for example, about 0.1 mg/mL to about 0.5 mg/mL, about 0.2 mg/mL to about 0.8 mg/mL, about 0.15 mg/mL to about 0.25 mg/mL, about 0.1 mg/mL to about 0.3 mg/mL, or about 0.05 mg/mL to about 0.3 mg/mL. In still another aspect, the formulation comprises a combination of all or any of the foregoing.

In another aspect, the formulation comprising rhTPP1 further comprises one or more buffering agents. For example, in various aspects, the formulation further comprises sodium phosphate dibasic heptahydrate at a concentration of about 0.01 mg/mL to about 1 mg/mL, for example, about 0.1 mg/mL to about 0.5 mg/mL, about 0.05 mg/mL to about 0.4 mg/mL, or about 0.1 mg/mL to about 0.3 mg/mL; and/or sodium phosphate monobasic monohydrate at a concentration of about 0.01 mg/mL to about 1 mg/mL, for example, about 0.01 mg/mL to about 0.2 mg/mL, about 0.05 mg/mL to about 0.3 mg/mL, or about 0.08 mg/mL to about 0.4 mg/mL.

In another aspect, the formulation further comprises an isotonicity agent, such as sodium chloride at a concentration of about 1 mg/mL to about 20 mg/mL, for example, about 1 mg/mL to about 10 mg/mL, about 5 mg/mL to about 15 mg/mL, or about 8 mg/mL to about 20 mg/mL. Other buffering agents and isotonicity agents known in the art are suitable and may be routinely employed for use in the formulations of the present disclosure.

In one aspect, a formulation comprising about 30 mg/mL of rhTPP1 further comprises sodium phosphate dibasic heptahydrate at a concentration of about 0.11 mg/mL, sodium phosphate monobasic monohydrate at a concentration of about 0.08 mg/mL, sodium chloride at a concentration of about 8.77 mg/mL, potassium chloride at a concentration of about 0.22 mg/mL, magnesium chloride hexahydrate at a concentration of about 0.16 mg/mL, calcium chloride dihydrate at a concentration of about 0.21 mg/mL, and a diluent, such as water for injection.

The rhTPP1 formulations of the present disclosure are stable and can be stored for extended periods of time without an unacceptable change in quality, potency, or purity. In one aspect, the formulation is stable at a temperature of about 5° C. (e.g., 2° C. to 8° C.) for at least 1 month, for example, at least 1 month, at least 3 months, at least 6 months, at least 12 months, at least 18 months, at least 24 months, or more. In another aspect, the formulation is stable at a temperature of less than or equal to about −20° C. for at least 6 months, for example, at least 6 months, at least 12 months, at least 18 months, at least 24 months, at least 36 months, or more. In another aspect, the formulation is stable at a temperature of less than or equal to about −40° C. for at least 6 months, for example, at least 6 months, at least 12 months, at least 18 months, at least 24 months, at least 36 months, or more. In another aspect, the formulation is stable at a temperature of less than or equal to about −60° C. for at least 6 months, for example, at least 6 months, at least 12 months, at least 18 months, at least 24 months, at least 36 months, or more.

In one aspect, a formulation of the disclosure is preservative-free and/or stabilizer-free and thus does not contain any of thimerosal, phenylmercurate salts, chlorhexidene, phenol, benzoic acid, sorbic acid, parabens, alcohols, or other preservatives commonly found in parenteral or ophthalmic formulations.

In another aspect, the formulation of the present invention may comprise one or more preservatives, stabilizers or excipients. In this regard, numerous well known and routinely employed preservatives, stabilizers and excipients useful for protein-containing formulations for intrathecal or ICV delivery are known in the art. More specifically, examples of such additives to enzyme-containing formulations for use in intrathecal or ICV delivery are described in WO2013/096899, which is herein incorporated by reference.

Methods

The disclosure provides methods of treating CLN2 disease comprising administering a therapeutically effective amount of a formulation comprising rhTPP1 described herein to a subject in need thereof. The disclosure also provides a composition comprising rhTPP1 for use in treating CLN2 disease described herein and use of rhTPP1 in the manufacture of a medicament for treating CLN2 disease described herein. In one aspect, severity and progression of CLN2 disease and the therapeutic benefit of administration of rhTPP1 in a patient can be measured using a Hamburg or WCMC clinical disease rating scale. Both the Hamburg and WCMC scales consist of four disease-related domains, which are scored in ratings on subscales of 0 to 3 points, such that 3 points is normal, 2 points is abnormal but functional, 1 point is abnormal and markedly dysfunctional, and 0 points is no residual function. Two of the four domains, gait/motor and language, are shared in common between the two scales, and have high intrinsic content validity. Each scale in total captures changes that occur as a function of both disease progression and disease management. Gait, language and vision scales capture disease progression. Seizure frequency, movement disorders and feeding are dependent on care decisions, particularly anticonvulsant medications and feeding tube management. The clinical progression is often assessed using the aggregate language and gait subscales, such that a rating of 6 points represents age-based normal and 0 points is complete loss of function. Table 1 depicts the WCMC and Hamburg CLN2 disease scales.

TABLE 1

| Weill Cornell Scale (WCMC) | | | Hamburg Scale | | |
|---|---|---|---|---|---|
| Gait | 3 | Normal | Motor | 3 | Walks normally |
| | 2 | Abnormal but independent | | 2 | Frequent falls, obvious clumsiness |
| | 1 | Abnormal requiring assistance | | 1 | No unaided walking or crawling only |
| | 0 | Nonambulatory | | 0 | Immobile, mostly bedridden |
| Language | 3 | Normal | Language | 3 | Normal |
| | 2 | Abnormal | | 2 | Recognizably abnormal |
| | 1 | Barely understandable | | 1 | Hardly understandable |
| | 0 | Unintelligible or no speech | | 0 | Unintelligible or no language |
| Myoclonus (motor) | 3 | None of myclonus, chorea/tremor/athetosis, and upgoing toes | Visual | 3 | Recognizes desirable object, grabs at it |
| | 2 | One of myclonus, chorea/tremor/athetosis, or upgoing toes | | 2 | Grabbing for objects uncoordinated |
| | 1 | Two of myclonus, chorea/tremor/athetosis, or upgoing toes | | 1 | Reacts to light |
| | 0 | Myoclonus and chorea/tremor/athetosis and upgoing toes | | 0 | No reaction to visual stimuli |
| Feeding | 3 | No swallowing dysfunction | Seizures | 3 | No seizure in 3 months |
| | 2 | Mild swallowing dysfunction | | 2 | 1-2 seizures in 3 months |
| | 1 | Moderate swallowing dysfunction | | 1 | 1 seizure per month |
| | 0 | Gastrostomy tube-dependent | | 0 | >1 seizure per month |

In various aspects, the disclosure provide a method of treating CLN2 disease, or one or more clinical symptoms of CLN2 disease, comprising administering a composition comprising a therapeutically effective amount of rhTPP1 to a subject in need thereof, use of rhTPP1 in the manufacture of a medicament for the treatment of CLN2 disease in a subject, or rhTPP1 for use in treating CLN2 disease in a subject.

The disclosure also provides methods of preventing one or more clinical symptoms of CLN2 disease comprising administering a formulation comprising rhTPP1 described herein to a subject in need thereof, optionally wherein the subject has a family history of CLN2 disease. In various aspects, the disclosure provide a method of preventing one or more clinical symptoms of CLN2 disease comprising administering a composition comprising a therapeutically effective amount of rhTPP1 to a subject in need thereof, use of rhTPP1 in the manufacture of a medicament for the prevention of one or more clinical symptoms of CLN2 disease in a subject, or rhTPP1 for use in preventing one or more clinical symptoms of CLN2 disease in a subject, optionally wherein the subject has a family history of CLN2 disease.

The disclosure further provides methods of treating CLN2 disease comprising administering rhTPP1 to a subject in need thereof at a dose effective to maintain a physiological function or slow or reduce deterioration of a physiological function in the subject, wherein the physiological function is language function, motor function, vision, or feeding function. The disclosure also provides use of rhTPP1 in the manufacture of a medicament for maintaining a physiological function or slowing or reducing deterioration of a physiological function in a subject having CLN2, and rhTPP1 for use in maintaining a physiological function or slowing or reducing deterioration of a physiological function in a subject having CLN2 disease; wherein the physiological function is language function, motor function, vision, or feeding function.

In one aspect, a method of treating a subject having CLN2 disease or a family history of CLN2 disease comprises administering a dose of rhTPP1 effective to maintain language function or slow or reduce deterioration of language function to the subject. In one aspect, the deterioration of language function is a reduction of at least one point compared to a previous rating determined before or during treatment as measured using a WCMC or Hamburg disease rating scale. In both the WCMC and Hamburg scales, a rating of 3 points indicates normal language; 2 points indicates (recognizably) abnormal language; 1 point indicates barely/hardly understandable language; and 0 points indicates unintelligible or no language. In one aspect, the dose of rhTPP1 is effective to maintain the subject's language rating at the same level as a previous rating determined before or during treatment, e.g., 3 points, 2 points or 1 point. In another aspect, the dose of rhTPP1 is effective to slow or reduce CLN2-associated deterioration of language function in the subject, which can be demonstrated by maintenance of the language rating at the same level for a longer period of time or a smaller decrease in the language function rating, compared to what would be expected considering the natural progression of the disease.

In another aspect, a method of treating a subject with CLN2 or a family history of CLN2 comprises administering a dose of rhTPP1 effective to maintain motor function or slow or reduce deterioration of motor function to the subject. In one aspect, the deterioration of motor function is a reduction of at least one point compared to a previous rating determined before or during treatment as measured using a WCMC or Hamburg disease rating scale. Either the clinical rating scale for gait in the WCMC scale or for motor in the Hamburg scale can be used to evaluate motor function. In both the WCMC and Hamburg scales, a rating of 3 points indicates normal walking; 2 points indicates abnormal but independent walking, e.g., with frequent falls or obvious clumsiness; 1 point indicates abnormal walking requiring assistance, e.g., no unaided walking or crawling only; and 0 points indicates the subject in non-ambulatory/immobile, e.g., mostly bedridden. In one aspect, the dose of rhTPP1 is effective to maintain the subject's motor function rating at the same level as a previous rating determined before or during treatment, e.g., 3 points, 2 points, or 1 point. In another aspect, the dose of rhTPP1 is effective to slow or reduce CLN2-associated deterioration of motor function in the subject, which can be demonstrated by maintenance of the motor rating at the same level for a longer period of time or a smaller decrease in the motor function rating, compared to what would be expected considering the natural progression of the disease.

In still another aspect, a method of treating a subject with CLN2 or a family history of CLN2 comprises administering a dose of rhTPP1 effective to maintain vision or slow or reduce deterioration of vision to the subject. In one aspect, the deterioration of vision is a reduction of at least one point compared to a previous rating determined before or during treatment as measured using a Hamburg disease rating scale. According to the Hamburg scale, a rating of 3 points indicates the subject recognizes a desirable object and grabs at it; 2 points indicates grabbing for objects uncoordinated; 1 point indicates the subject reacts to light, and 0 points indicates the subject has no reaction to visual stimuli. In one aspect, the dose of rhTPP1 is effective to maintain the subject's vision rating at the same level as a previous rating determined before or during treatment, e.g., 3 points, 2 points or 1 point. In another aspect, the dose of rhTPP1 is effective to slow or reduce CLN2-associated deterioration of vision in the subject, which can be demonstrated by maintenance of the vision rating at the same level for a longer period of time or a smaller decrease in the vision rating, compared to what would be expected considering the natural progression of the disease.

In another aspect, a method of treating a subject with CLN2 or a family history of CLN2 comprises administering a dose of rhTPP1 effective to maintain feeding function or slow or reduce deterioration of feeding function to the subject. In one aspect, the deterioration of feeding function is a reduction of at least one point compared to a previous rating determined before or during treatment as measured using a WCMC rating scale. According to the WCMC scale, a rating of 3 points indicates no swallowing dysfunction; 2 points indicates mild swallowing dysfunction; 1 point indicates moderate swallowing dysfunction, and 0 points indicates the subject is gastronomy-tube dependent. In one aspect, the dose of rhTPP1 is effective to maintain the subject's feeding function rating at the same level as the previous rating determined before or during treatment, e.g., 3 points, 2 points, or 1 point. In another aspect, the dose of rhTPP1 is effective to slow or reduce CLN2-associated deterioration of feeding function in the subject, which can be demonstrated by maintenance of the feeding function at the same level for a longer period of time or a smaller decrease in the feeding rating, compared to what would be expected considering the natural progression of the disease.

The disclosure further provides methods of treating CLN2 disease comprising administering rhTPP1 to a subject in need thereof at a dose effective to improve a physiological function, wherein the physiological function is language function, motor function, vision, or feeding function. The disclosure also provides use of rhTPP1 in the manufacture of a medicament for improving a physiological function in a subject having CLN2, or rhTPP1 for use in improving a physiological function in a subject having CLN2; wherein the physiological function is language function, motor function, vision, or feeding function. Considering the progressively degenerative nature of the disease, an improvement in language function, motor function, vision, and/or feeding function, indicating that the subject has regained lost function, is especially desirable, but difficult to achieve with current treatment options.

In one aspect, a method of treating a subject with CLN2 disease comprises administering a dose of rhTPP1 effective to improve language function to the subject. In one aspect, the improvement in language function is an increase of at least one point compared to a previous rating determined before or during treatment as measured using a WCMC or Hamburg disease rating scale. For example, a subject can improve from a rating of 1 point or 2 points to a rating of 3 points, indicating a return to normal language, or improve from a rating of 1 point to a rating of 2 points.

In another aspect, a method of treating a subject with CLN2 disease comprises administering a dose of rhTPP1 effective to improve motor function to the subject. In one aspect, the improvement in motor function is an increase of at least one point compared to a previous rating determined before or during treatment as measured using a WCMC or Hamburg disease rating scale. For example, a subject can improve from a rating of 1 point or 2 points to a rating of 3 points, indicating a return to normal walking, or improve from a rating of 1 point to a rating of 2 points.

In one aspect, a method of treating a subject with CLN2 disease comprises administering a dose of rhTPP1 effective to improve vision to the subject. In one aspect, the improvement in vision is an increase of at least one point compared to a previous rating determined before or during treatment as measured using a Hamburg disease rating scale. For example, a subject can improve from a rating of 1 point or 2 points to a rating of 3 points, or improve from a rating of 1 point to a rating of 2 points.

In another aspect, a method of treating a subject with CLN2 disease comprises administering a dose of rhTPP1 effective to improve feeding function to the subject. In one aspect, the improvement in feeding function is an increase of at least one point compared to a previous rating determined before or during treatment as measured using a WCMC disease rating scale. For example, a subject can improve from a rating of 1 point or 2 points to a rating of 3 points, indicating a return to normal swallowing, or improve from a rating of 1 point to a rating of 2 points or 3 points.

The disclosure further provides methods of treating CLN2 disease comprising administering rhTPP1 to a subject in need thereof at a dose effective to prevent or treat a neurological symptom of the disease, wherein the neurological symptom is a seizure, decrease in brain volume, decrease in gray matter in the brain, or increase of cranial cerebrospinal fluid (CSF). The disclosure also provides use of rhTPP1 in the manufacture of a medicament for preventing or treating a neurological symptom in a subject having CLN2 or a family history of CLN2, and rhTPP1 for use in preventing or treating a neurological symptom in a subject having CLN2 or a family history of CLN2; wherein the neurological symptom is a seizure, decrease in brain volume, decrease in gray matter in the brain, or increase of cranial CSF.

In one aspect, a method of treating a subject having CLN2 or a family history of CLN2 comprises administering a dose of rhTPP1 effective to maintain or reduce the number of seizures to a subject. In one aspect, the dose is effective to reduce the number of seizures per month that the subject experiences. In another aspect, the dose is effective to increase the seizure rating by at least one point compared to a previous rating determined before or during treatment as measured using a Hamburg disease rating scale. According to the Hamburg scale, a rating of 3 points indicates no seizure in 3 months; 2 points indicates 1 to 2 seizures in 3 months; 1 point indicates 1 seizure per month; and 0 points more than 1 seizure per month. In one aspect, the dose of rhTPP1 is effective to maintain the subject's seizure rating at the same level as the previous rating determined before or during treatment, e.g., 3 points, 2 points, or one point. In another aspect, the dose of rhTPP1 is effective to maintain or reduce the number of seizures in the subject, which can be demonstrated by maintenance of the number of seizures per month for a longer period of time or a smaller decrease in the seizure rating, compared to what would be expected considering the natural progression of the disease.

In another aspect, a method of treating a subject having CLN2 or a family history of CLN2 comprises administering a dose of rhTPP1 effective to maintain brain volume or slow or reduce the decrease in brain volume to a subject. Brain atrophy increases as the disease progresses, resulting in a loss of brain volume and an associated increase in the volume and relative proportion of intracranial CSF. Brain volume can be measured using methods known in the art, including imaging techniques such as magnetic resonance imaging (MRI), computed tomography (CT/CAT), positron emission tomography (PET), single photon emission computerized tomography (SPECT), electroencephalography (EEG), magnetoencephalography (MEG), and near infrared spectroscopy (NIRS). In one aspect, the dose of rhTPP1 is effective to slow or reduce the CLN2-associated decrease in brain volume in the subject, which can be demonstrated by maintenance of brain volume for a longer period of time or a smaller decrease in brain volume, compared to what would be expected considering the natural progression of the disease.

In another aspect, method of treating a subject having CLN2 or a family history of CLN2 comprises administering a dose of rhTPP1 effective to maintain gray matter in the brain or slow or reduce the decrease of gray matter in the brain to a subject. A loss of gray matter due to brain atrophy occurs as the disease progresses, resulting in a decrease in gray matter as a percentage of brain volume. The amount of gray matter in the brain can be assessed using methods known in the art, for example, imaging techniques such as MRI, CT/CAT, PET, SPECT, EEG, MEG, and NIRS. In one aspect, the dose of rhTPP1 is effective to slow or reduce the decrease in gray matter in the subject, which can be demonstrated by maintenance of gray matter volume for a longer period of time or a smaller decrease in gray matter as a percentage of brain volume, compared to what would be expected considering the natural progression of the disease.

In another aspect, a method of treating a subject having CLN2 or a family history of CLN2 comprises administering a dose of rhTPP1 effective to maintain the volume of cranial CSF or slow the increase in the volume of cranial CSF to a subject. Cranial CSF increases in volume and proportion of total CSF as a result of cerebral atrophy. The amount and proportion of cranial CSF can be assessed using methods known in the art, for example, imaging techniques such as MRI and CT/CAT. In one aspect, the dose of rhTPP1 is effective to slow or reduce the increase in cranial CSF in the subject, which can be demonstrated by maintenance of the volume of cranial CSF for a longer period of time or a smaller increase in cranial CSF as a percentage of total CSF, compared to what would be expected considering the natural progression of the disease.

The foregoing methods, compositions for use, and uses may further comprise any of the following features, alone and in combination.

In one aspect, a method, composition for use, or use of the disclosure comprises administering a formulation, composition or dose comprising rhTPP1 to a subject continuously or continually over a period of at least about 1 hour, for example, at least about 1 hour, at least about 2 hours, at least about 3 hours, at least about 4 hours, at least about 5 hours, at least about 6 hours, or more. In another aspect, a method or use of the disclosure comprises administering a formulation, composition or dose comprising about 20 mg to about 500 mg, about 30 mg to about 500 mg, about 50 mg to about 500 mg, about 100 mg to about 500 mg, about 200 mg to about 400 mg, about 250 mg to about 350 mg, or about 275 mg to about 325 mg of rhTPP1 to a subject in need thereof, for example, about 20 mg, about 30 mg, about 50 mg, about 100 mg, about 200 mg, about 300 mg, about 400 mg, or about 500 mg of rhTPP1. In one aspect, a method or use of the disclosure comprises administering a formulation, composition or dose having a volume of about 20 mL or less, about 15 mL or less, about 10 mL or less, about 7.5 mL or less, or about 5 mL or less, for example, about 20 mL, about 15 mL, about 10 mL, about 9 mL, about 8 mL, about 7 mL, about 6 mL, about 5 mL, about 4 mL, about 3 mL about 2 mL, about 1 mL, or about 0.5 mL per dose or administration event.

In various aspects, a method, composition for use, or use of the disclosure comprises administering a formulation, composition or dose comprising rhTPP1 to a subject at a rate of less than or equal to about 2.5 mL of the formulation, composition or dose per hour; less than or equal to about 75 mg of rhTPP1 per hour; or less than or equal to about 75 mg of rhTPP1 per 2.5 mL of formulation or composition per hour. The formulation, composition or dose is optionally administered continuously or continually over a period of at least about 4 hours.

In one aspect, a method, composition for use, or use of the disclosure comprises administering a formulation, composition or dose comprising rhTPP1 weekly or less frequently, for example, weekly, every other week, or monthly. More specifically, a method, composition for use, or use of the disclosure comprises administering a formulation, composition or dose comprising rhTPP1 once every 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, or 31 days. In one aspect, the formulation, composition or dose is administered intracerebroventricularly. In another aspect, the formulation, composition or dose is administered intrathecally. In still another aspect, the formulation, composition or dose is administered intraocularly. In one aspect, the formulation, composition or dose is administered intracerebroventricularly or intrathecally, as well as intraocularly. Intracerebroventricular delivery allows penetration to the deep gray structures of the brain such as the thalami, striatum and midbrain, due to the physiology of CSF flow in which ventricular delivery allows flow into third and fourth ventricles, but also percolates through the neuropil of the cerebral hemispheres, along a slight pressure gradient from ventricle to subarachnoid space. Intrathecal and intracerebroventricular administration of recombinant enzyme to treat lysosomal storage disorders are described in U.S. Pat. No. 7,442,372, incorporated herein by reference in its entirety.

A formulation, composition, or dose of rhTPP1 of the disclosure may be administered in a single bolus injection or series of injections (e.g., into the brain, lumbar region, or eye), or as a continuous or continual infusion, e.g., using an infusion pump or other implanted device. In one aspect, a formulation, composition, or dose of rhTPP1 is administered using an infusion system comprising tubing, an in-line filter (e.g., about 0.2 µm), a reservoir (e.g., intrathecal or intracerebroventricular), and a catheter. Frequently, when a composition is administered intrathecally or intracerebroventricularly, in order to prevent adverse side effects resulting from artificially increasing intracerebral or intrathecal pressure, a volume of CSF comparable to the volume of composition to be administered is first removed from the subject before the composition is administered. As described in Example 3, however, it is herein demonstrated that a formulation, composition, or dose of rhTPP1 of the disclosure may be administered without removal of any volume of CSF from the subject just prior to administration of the formulation, composition, or dose of rhTPP1.

In one aspect, a method or use of the disclosure comprises administering about 10 mL of a formulation, composition or dose comprising about 300 mg of rhTPP1 intracerebroventricularly over a period of about 4 hours every other week to a subject having CLN2.

The formulations and compositions of the present invention may be directly administered to a subject in need (i.e., non-isovolumetric) or may be administered subsequent to removal of a defined volume of CSF from the subject prior, wherein that defined volume is approximately the same as the volume of the composition subsequently administered (i.e., isovolumetric).

In one aspect, a method, composition for use, or use of the disclosure further comprises administering a flushing solution to the subject following administration of the rhTPP1. The flushing solution is administered via the same route as the rhTPP1 and using the same delivery system (e.g., an infusion system), to remove any rhTPP1 remaining in the delivery system and to ensure the subject received the full intended dose of rhTPP1. In one aspect, the flushing solution is administered (e.g., using the same catheter previously used to administer a composition comprising rhTPP1) to the subject in an amount between about 0.5 mL and about 5 mL, for example, about 0.5 mL, about 1 mL, about 2 mL, about 3 mL, or about 5 mL. In one aspect, the flushing solution comprises the same components as the formulation or composition comprising rhTPP1, but without the rhTPP1. In one aspect, the flushing solution comprises sodium phosphate dibasic heptahydrate at a concentration of about 0.11 mg/mL, sodium phosphate monobasic monohydrate at a concentration of about 0.08 mg/mL, sodium chloride at a concentration of about 8.77 mg/mL, potassium chloride at a concentration of about 0.22 mg/mL, magnesium chloride hexahydrate at a concentration of about 0.16 mg/mL, calcium chloride dihydrate at a concentration of about 0.21 mg/mL, and a diluent, such as water for injection.

Kits

The disclosure further provides kits comprising a formulation of rhTPP1 described herein, in a dose and form suitable for administration to a patient. In one aspect, the kit comprises a formulation comprising about 30 mg/mL of rhTPP1, sodium phosphate dibasic heptahydrate at a concentration of about 0.11 mg/mL, sodium phosphate monobasic monohydrate at a concentration of about 0.08 mg/mL, sodium chloride at a concentration of about 8.77 mg/mL, potassium chloride at a concentration of about 0.22 mg/mL, magnesium chloride hexahydrate at a concentration of about 0.16 mg/mL, calcium chloride dihydrate at a concentration of about 0.21 mg/mL, and a diluent, such as water for injection. In one aspect, the kit further comprise instructions for the intracerebroventricular, intrathecal, and/or intraocular administration of the therapeutic compositions of the present invention, in addition to the therapeutic formulation. In another aspect, the kit further comprises a flushing solution as described herein. In still another aspect, the kit further comprises a system for administering the formulation, comprising any or all of the following components: tubing, an in-line filter, a reservoir for implantation, and a catheter. In one aspect, the kit may comprise catheters, reservoirs, or other devices preloaded with the therapeutic formulations of the present disclosure. For example, catheters preloaded with about 100 mg of rhTPP1, about 200 mg of rhTPP1, about 300 mg of rhTPP1, about 400 mg of rhTPP1, or about 500 mg of rhTPP1, in a pharmaceutically acceptable formulation, are specifically contemplated. Alternatively, the kit may comprise catheters, reservoirs, or other devices that are refillable and appropriate amounts of the enzyme for refilling such devices.

In certain embodiments, kits of the present invention may comprise one or more of the following components: an extension line (e.g., product number 536040, Smiths Medical, Dublin O H), an in-line filter (e.g., product number FS116, Smiths Medical), a port needle (e.g., product number 21-2737-24, Smiths Medical), a syringe or two or more syringes (e.g., product number 309604, Becton Dickinson, Franklin Lakes, N.J.) or a syringe needle or two or more syringe needles (e.g., product number 305196, Becton Dickinson).

The present disclosure will be more readily understood by reference to the following Examples, which are provided by way of illustration and are not intended to be limiting.

EXAMPLES

The following Examples describe a formulation comprising rhTPP1 for intracerebroventricular (ICV) administration and the results of administering the formulation to human patients compared to matched, untreated natural history patients.

Example 1

Formulation of rhTPP1 for Intracerebroventricular Administration

RhTPP1 was produced in a genetically engineered CHO host cell line and purified by standard chromatography methods, as described in U.S. Pat. No. 6,302,685 and Sleat et al. 1997, *Science* 277:1802-1805, incorporated herein by reference in their entirety. The rhTPP1 was produced as an inactive proenzyme to be auto-activated at acidic pH upon uptake to the lysosome. The proenzyme form of rhTPP1 has a calculated isotope average molecular weight of approximately 59 kDa. The mature enzyme has an apparent molecular weight of approximately 46 kDa. The amino acid sequence of the rhTPP1 proenzyme is set forth in SEQ ID NO:1 and shown in FIG. 1. The pro-segment of the enzyme is the first 176 amino acid residues, and the mature enzyme is 368 amino acids in length starting at position 177 and is set forth in SEQ ID NO:2.

The rhTPP1 formulation used in the Examples was a sterile solution for ICV infusion. It was a clear and colorless to pale yellow liquid containing rhTPP1 protein formulated at a concentration of 30 mg/mL. The formulation was packaged in a container closure system consisting of a Type 1 clear borosilicate glass vial closed with a fluoropolymer coated butyl rubber stopper and capped with aluminum seal. The formulation was stored at a temperature of −40° C.±10° C. and supplied frozen. The target pH value of the formulation was pH 6.5.

The composition of the rhTPP1 formulation used in the Examples is provided in Table 2.

TABLE 2

| Component | Concentration (mg/mL) | Composition per vial | Function | Compendial Grade |
|---|---|---|---|---|
| rhTPP1 | 30 | 30 mg | Active Ingredient | NA |
| Sodium Phosphate Dibasic, Heptahydrate | 0.11 | 0.11 mg | Buffering Agent | USP/Ph.Eur |
| Sodium Phosphate Monobasic Monohydrate | 0.08 | 0.08 mg | Buffering Agent | USP/Ph.Eur |
| Sodium Chloride | 8.77 | 8.77 mg | Isotonicity Agent | USP/Ph.Eur/JP |
| Potassium Chloride | 0.22 | 0.22 mg | Maintain the level of key CSF electrolyte | USP/Ph.Eur/JP |
| Magnesium Chloride Hexahydrate | 0.16 | 0.16 mg | Maintain the level of key CSF electrolyte | USP/Ph. Eur |
| Calcium Chloride Dihydrate | 0.21 | 0.21 mg | Maintain the level of key CSF electrolyte | USP/Ph.Eur/JP |
| Water for Injection (qs) | NA | 1.00 mL | Diluent | USP/Ph.Eur/JP |

The rhTPP1 formulation was carefully designed to mimic characteristics of human CSF, such as the concentrations of key electrolytes are similar to those found in human CSF in vivo and the formulation did not contain any conventional preservatives or stabilizers as excipients. No significant safety issues, i.e., serious adverse reactions, were reported or observed following administration of the rhTPP1 formulation, which could not have been previously predicted.

Stability studies were conducted at long-term (≤−60° C.) and accelerated conditions (5±3° C.) in accordance with ICH guidelines and per protocol to monitor the time-temperature stability. Stability samples were stored in small-scale bottles composed of the same materials as the full-scale packaging. Stability data collected on supportive and clinical batches demonstrated that the rhTPP1 formulation was stable at ≤−60° C. for at least 36 months and at 5±3° C. for at least 6 months, which was surprising considering the formulation lacked preservatives and stabilizers commonly found in pharmaceutical products. Table 3 shows the results of the stability testing.

TABLE 3

| Test | Specification | Storage | \multicolumn{8}{c}{Time Point (months)} |
| --- | --- | --- | --- | --- | --- | --- | --- | --- | --- | --- |
| | | | 0 | 3 | 6 | 9 | 12 | 18 | 24 | 36 |
| QUALITY | | | | | | | | | | |
| Appearance | Colorless to pale yellow liquid | Long-term | X | X | X | X | X | X | X | X |
| | | Accelerated | X | X | X | | | | | |
| Sialic Acid | 2-7 mol/mol | Long-term | X | | X | | X | X | X | X |
| | | Accelerated | X | | X | | | | | |
| POTENCY | | | | | | | | | | |
| Specific Activity, Acid Activated | 5-15 U/mg | Long-term | X | X | X | X | X | X | X | X |
| | | Accelerated | X | X | X | | | | | |
| Specific Activity Without Acid Activation | ≤0.075 U/mg | Long-term | X | X | X | X | X | X | X | X |
| | | Accelerated | X | X | X | | | | | |
| Oligosaccharide Profile | Comparable to reference 10-26% bis-mannose-6-phosphate oligomannose$_7$ | Long-term | X | X | X | X | X | X | X | X |
| | | Accelerated | X | X | X | | | | | |
| Cellular Uptake | ≤10 nM | Long-term | X | | X | | X | X | X | X |
| | | Accelerated | X | | X | | | | | |
| STRENGTH | | | | | | | | | | |
| Protein Concentration | 27-33 mg/mL | Long-term | X | X | X | X | X | X | X | X |
| | | Accelerated | X | X | X | | | | | |
| PURITY | | | | | | | | | | |
| Related Substances by RP-HPLC | Report Result (% Main Peak) | Long-term | X | X | X | X | X | X | X | X |
| | | Accelerated | X | X | X | | | | | |
| Molecular Size Variants | ≥95% Monomer | Long-term | X | X | X | X | X | X | X | X |
| | | Accelerated | X | X | X | | | | | |
| Charge Heterogeneity | Comparable to reference ≥95% Main Peak | Long-term | X | X | X | X | X | X | X | X |
| | | Accelerated | X | X | X | | | | | |
| Related Substances | Comparable to reference | Long-term | X | X | X | X | X | X | X | X |
| | | Accelerated | X | X | X | | | | | |
| COMPOSITION | | | | | | | | | | |
| pH | 6.0-7.0 | Long-term | X | X | X | X | X | X | X | X |
| | | Accelerated | X | X | X | | | | | |
| Osmolality | 270-330 mOSm/Kg | Long-term | X | X | X | X | X | X | X | X |
| | | Accelerated | X | X | X | | | | | |

Example 2

Natural History Study

The quantitative assessment of CLN2 natural history disease progression was analyzed in a cohort of 41 untreated CLN2 patients. The Hamburg clinical scale was used for the assessment of age-appropriate neurological and functional domains affected by disease.

The quantitative description of the clinical decline in the untreated natural history CLN2 subjects is shown in FIG. 2. The natural history analysis demonstrated a clear and predictable relationship of age to disease severity. After the onset of motor and language symptoms, there was essentially a rapid linear decline in which children, on average, lost about 2 milestone events each year (linear rate of decline 2.1 points per year). There was a largely predictable course, however, there were some 'late onset' cases which made up less than 20% of the population in the cohort. These patients tended to have later onset of symptoms and a longer period of mild disease, but then succumbed to rapid and active decline, typically 2 to 3 years later than the classic form.

Quantitative clinical progression from the Hamburg cohort was corroborated by superimposing the clinical ratings assessments from an independent (patients and raters) cohort from WCMC (n=49). Although clinical descriptions of independent CLN2 cohorts are similar, this was the first confirmation of strong quantitative relationship in disease progression in separate patient groups. Both cohorts of CLN2 patients had a large majority of classic late infantile onset and progression, and a smaller proportion of children that had a 'late onset' phenotype, usually having early manifestations of disease at age 5 years rather than at 3 years. The scale using motor (gait) and language function reproducibly captured the neurologic decline of CLN2 patients. Based on the foregoing analyses, the cohort of natural study subjects was determined to be an appropriate non-treatment control population, and the average rate of decline of a symptom of CLN2 disease in this untreated, natural history population can be used as an effective and informative comparator for any prevention or reduction in the rate of decline of a symptom in a subject suffering from CLN2 disease caused by administration of a composition of the present invention.

Example 3

Phase 1/Phase 2 Open Label Dose-Escalation Study in CLN2 Patients

The study was an open label treatment clinical trial to evaluate the safety, tolerability and efficacy of a rhTPP1 formulation of the disclosure delivered to children with CLN2 disease through an ICV catheter at a dose of 300 mg (10 mL total volume) every other week. The study was designed to assess safety and tolerability starting at low doses (30 mg and 100 mg), but all patients escalated to the high expected therapeutic dose (300 mg) when the lower doses were noted by an independent data monitoring committee to be safe. The study duration for all enrolled patients was 48 weeks of treatment at the stable expected therapeutic dose of 300 mg ICV every other week. The primary study objectives were to evaluate safety and tolerability of a rhTPP1 formulation of the disclosure administered to subjects with CLN2 disease by an implanted ICV reservoir and cannula and to evaluate effectiveness using a CLN2 disease-specific rating scale score in comparison with natural history data after 12 months of treatment. The secondary study objectives were to evaluate the impact of treatment on measurement of brain atrophy in comparison with CLN2 disease natural history data after 12 months of treatment.

The major inclusion criteria were a CLN2 diagnosis and an enrollment age of at least 3 years old. Patients having a baseline disease rating score less than 3 at the time of screening (using the Hamburg 0 to 6 aggregate motor/language scale) were excluded from the study. Patients less than 3 year old were likely to not progress due to age rather than treatment, as depicted by the horizontal line on the progression curve. Patients with a score at screening of 2 or less were also less linear, more variable and considered potentially more refractory to treatment due to the stage of disease. Thus, the treatment group was simply defined by age and score to include early and highly predictable decline.

Mean age at enrollment was 4.0 years old, slightly more girls than boys, predominantly Caucasian. The clinical CLN2 score at screening and baseline is shown in Table 4 below, which shows the Hamburg motor/language score for each study cohort and totals at both screening and baseline.

TABLE 4

CLN2 Ratings—6 point Hamburg Scale—Last Assessment within Each Dosing Period Analysis Population: Intent-to-treat Analysis Dataset: Entire Dosing Period

|   | Cohort 1 (n =3) | Cohort 2 (n =3) | Cohort 3 (n =3) | Stable Dosing Only (n =14) | Overall (n =23) |
|---|---|---|---|---|---|
| Screening | | | | | |
| 6 | 1 (33%) | 0 | 1 (33%) | 0 | 2 (9%) |
| 5 | 0 | 0 | 0 | 2 (14%) | 2 (9%) |
| 4 | 0 | 0 | 0 | 6 (43%) | 6 (26%) |
| 3 | 2 (67%) | 3 (100%) | 2 (67%) | 6 (43%) | 13 (57%) |
| Study Baseline | | | | | |
| 6 | 1 (33%) | 0 | 1(33%) | 0 | 2 (9%) |
| 5 | 0 | 0 | 0 | 2 (14%) | 2 (9%) |
| 4 | 0 | 0 | 0 | 5 (36%) | 5 (22%) |
| 3 | 2 (67%) | 3 (100%) | 1 (33%) | 6 (43%) | 12 (52%) |
| 2 | 0 | 0 | 1 (33%) | 1 (7%) | 2 (9%) |
| 1 | 0 | 0 | 0 | 0 | 0 |
| 0 | 0 | 0 | 0 | 0 | 0 |

Overall, there was a skew in the pre-treatment CLN2 scores towards more advanced disease. Given the rapid progression of the disease and the ascertainment difficulties, a skew towards the lower scores was expected. Further, there was some decline in the score at screening and in the period (up to two weeks) to the baseline assessment (just before placement of the ICV reservoir). Four patients from the screening group that scored 3 slipped a point at baseline, and two patients in the screening group that scored a 4 lost a point to 3 at baseline. The two patients that entered as a 6 (i.e., grossly normal) were siblings of affected children. The disposition, demographics, and characteristics of the subject population are summarized in Table 5 below.

TABLE 5

|   |   | Overall |
|---|---|---|
| Disposition | Subjects enrolled | 24 |
|  | Subjects treated | 24 |
|  | Subjects completed | 23 |
|  | Subjects discontinued | 1[a] |
| Age (years) | Mean (SD) | 4.3 (1.24) |
| Baseline CLN2 score | 6 | 2 |
| Sum of | 5 | 2 |
| Motor/Language | 4 | 6 |
|  | 3 | 12 |
|  | 2 | 2 |
|  | Mean (SD), Median | 3.6 (1.06), 3.0 |
| Genotype[b] | Common* | 9 (37.5%) |
|  | Common x Other | 8 (33.3%) |
|  | Other | 7 (29.2%) |

[a]Enrolled patient 1287-1007 had a single dose and withdrew consent due to inability to comply with study procedures
[b]Similar distribution to natural history population
*Common Genotypes: c.622C > T and c.509-1G > C All patients enrolled received stable dosing of 300 mg ICV every other week. Cohort 1 was exposed to ≥1 month at 30 mg ICV every other week, then ascended to 100 mg ICV every other week for ≥4 weeks, while Cohort 2 was started on 100 mg ICV every other week for ≥4 weeks. Both Cohort 1 and Cohort 2 ascended to 300 mg ICV every other week, and all subsequent patients including Cohort 3 initiated dosing at the stable dose regimen of 300 mg ICV every other week and continued for ≥48 weeks. The 300 mg dose was administered in 10 mL infused over a period of about 4 hours via an ICV catheter. A volume of CSF, e.g., equivalent to the amount of the rhTPP1 formulation to be administered, was not removed just prior to the start of the infusion, which was atypical, but surprisingly did not cause any adverse effects. Immediately following administration of the 300 mg dose, a flushing solution in an amount of about 2 mL was administered to the subject via the same ICV catheter. The flushing solution was identical to the formulation in Table 2, but did not contain rhTPP1. The bolus dose of 300 mg of enzyme per administration event was significantly higher than previous intrathecal or ICV administered enzyme replacement therapies and, as such, the safety and efficacy profiles observed after administration of such a high dose of drug could not have been previously predicted. More specifically, administration of a 300 mg bolus dose of rhTPP1 without associated serious, unmanageable adverse events could not have been previously predicted.

Results

Effect of Treatment on Clinical Assessments of Gait and Language:

The primary assessment tool for the quantitative evaluation of clinical severity was the 0 to 6 point aggregate of the gait and language subscales common to both the Hamburg and WCMC disease rating scales. This scale captured the predictable, rapid, and progressive clinical decline in matched, untreated natural history patients that was used as a comparator for the primary efficacy analysis.

The gait/language disease rating score for 23 patients with treatment duration of more than 42 weeks is shown in FIGS. 3A to 3F. Of the 23 patients, 3 patients (1244-1001, 1244-1002, and 1244-1003) were from Cohort 1 (C1), 3 patients (1244-1004, 1244-1006, and 1287-1005) were from Cohort 2 (C2), 3 patients (1244-1008, 1244-1009, 1244-1010) were from Cohort 3 (C3), and 14 patients (0119-1020, 0146-1021, 0146-1022, 0146-1023, 1244-1011, 1244-1012, 1244-1017, 1244-1024, 1323-1013, 1323-1014, 1323-1015, 1323-1016, 1323-1018, and 1323-1019) were from the 300 mg Stable Dosing Only (SBO) group. As expected, language deficit was typically more advanced than gait deficit. Entry scores were not randomly distributed; 12 patients had significant disease progression with a combined entry score of 3 points, and 2 patients had a combined entry score of 6 points. Given rapid progression and disease ascertainment, children frequently present with evident decline or as siblings of those with evident decline.

Following treatment with a rhTPP1 formulation of the disclosure (shown in Table 2 above), the CLN2 gait/language disease rating score was stabilized, as shown in FIGS. 3A to 3F. Eleven of 23 patients had no unreversed decline over the treatment period. Four patients had a single unit decline early in the treatment period, but no un-reversed decline thereafter. Two patients (1244-1008 and 1323-1013) decreased by one unit from 3 to 2 points between screening and baseline, but did not experience any additional loss in ratings while on treatment. Based on the results, there was evident treatment benefit in all patients regardless of cohort (starting dose) or entry score. In a number of patients, there were reversed ratings drops. For example, Patient 1287-1005 (FIG. 3B) had a rating decrease of 2 units in the first month of treatment, which represented a loss of function for both gait and language. However, this patient regained a unit at treatment day 60, and had no net change afterwards until analysis day 440. The regained score was the acquisition of language, underscoring the clinical importance of single unit changes.

Neither of the 2 patients with a score of 6 at entry lost a rating unit. Seven of the 12 patients with an entry score of 3 had no unreversed decline, and 2 were stable after an initial single unit decline. Thus, treatment benefit was evident in patients with significant deficits and disease progression.

As demonstrated in the CLN2 natural history study, the median rate of decline in the untreated natural history population was estimated at 2.1 units each year. Thus, all patients in the treatment group had improved ratings compared to the expected outcomes of the untreated natural history population.

To establish a clearer relationship in the disease course between treated and matched, untreated natural history patients, each study patient was matched with untreated natural history patients by the parameters of baseline CLN2 score, age and genotype. Although there are no clear subgroups or factors predictive of progression in CLN2 disease, these parameters are most commonly used to define disease severity. Individual treated patients were compared to each member of the natural history cohort that had similar gait/language rating score at baseline, as shown in FIGS. 4A to 4I. Patients in the study were matched by baseline CLN2 score, as follows: for a given study patient with a given baseline score, all natural history patients who reported one or more CLN2 evaluations with that same CLN2 score were identified. If the study patient's baseline CLN2 score was 2, 3, 4, or 5, then each natural history patient's CLN2-vs-time profile was time-shifted left or right so that it overlaid the study patient's baseline score. If the natural history patient had multiple assessments equaling the study patient's baseline CLN2 score, then the mid-time point of the multiple assessments was used for time-shifting. If the study patient's baseline CLN2 score was 6 points, then the natural history patient's last score of 6 points was used for time-shifting. Sensitivity analyses were conducted using other matching criteria, and results from these analyses were consistent with the score-matched analyses.

FIGS. 4A to 4I show results from subjects treated with a rhTPP1 formulation of the disclosure plotted against matched, untreated natural history patients. The treated subjects and untreated natural history patients were matched by disease rating score using the 0 to 6 unit gait and language subscales as an aggregate. The ratings of each were compared over the period of one year of treatment. There was a treatment benefit for the subjects that received rhTPP1 compared to all members of the matched, untreated natural history patient group. Subject 1244-1001 (FIG. 4A) had a rating decrease from 3 units to 2 units after 120 days of treatment, but regained a unit and had no net change afterwards. Subject 1244-1002 (FIG. 4B) had a rating increase from 3 units to 4 units, a decrease from 4 units to 2 units, and an increase from 2 units to 3 units, resulting in overall maintenance of the disease rating at the end of the study compared to Day 1. Subjects 1244-1003 (FIG. 4C) and 1244-1010 (FIG. 4I) maintained a rating of 6 units, i.e., normal motor and language function, throughout the study. Subjects 1244-1004 (FIG. 4D) and 1244-1009 (FIG. 4H) maintained a rating of 3 units throughout the study. Subject 1244-1006 (FIG. 4E) had a rating decrease from 3 units to 2 units initially, but regained a unit before decreasing again from 3 units to 2 units with no net changes afterwards. Subject 1244-1008 (FIG. 4G) had a rating decrease from 3 units to 2 units initially, with no net changes afterwards.

In contrast to all of the treated subjects, the majority of their matched, untreated natural history patients had an unreversed rating decrease from 3 units to 0 units by the end of the comparative period, indicating a progression to complete lack of function for gait and language combined. The matching analysis demonstrates the treatment benefit for those patients that maintain their disease rating score and also that have an initial ratings drop, but subsequently stabilize.

Figure 4A:
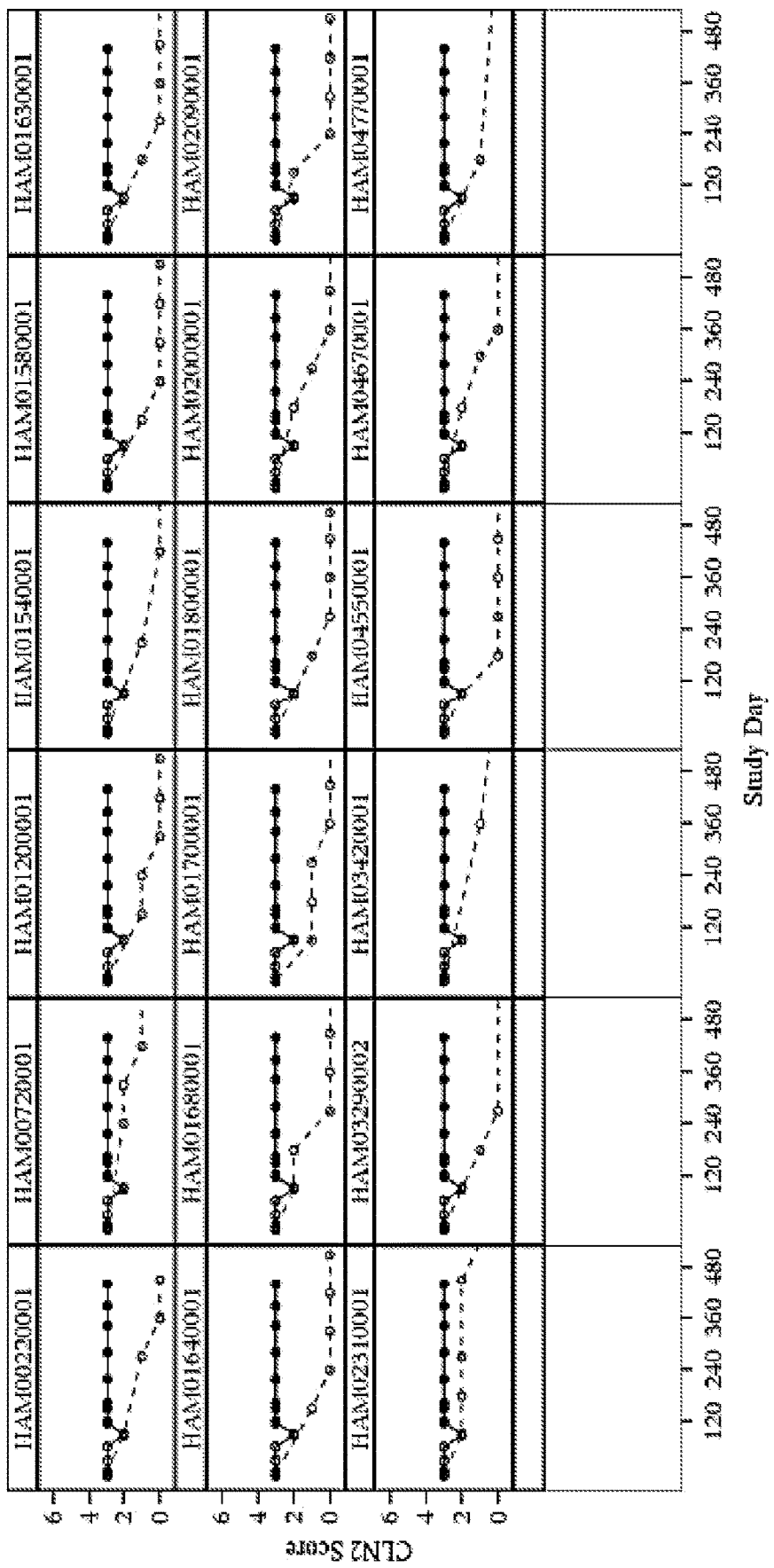
FIGS. 4A to 4I compare the change in CLN2 score from 9 patients treated with rhTPP1 to untreated natural history patients matched to the treated subjects by disease rating score (denoted with the prefix "HAM") on the 0 to 6 Hamburg motor and language aggregate scale. Results for the treated patients are shown with a solid line in each panel compared to results for matched, untreated natural history patients, which are shown with a broken line.
Figure 4B:
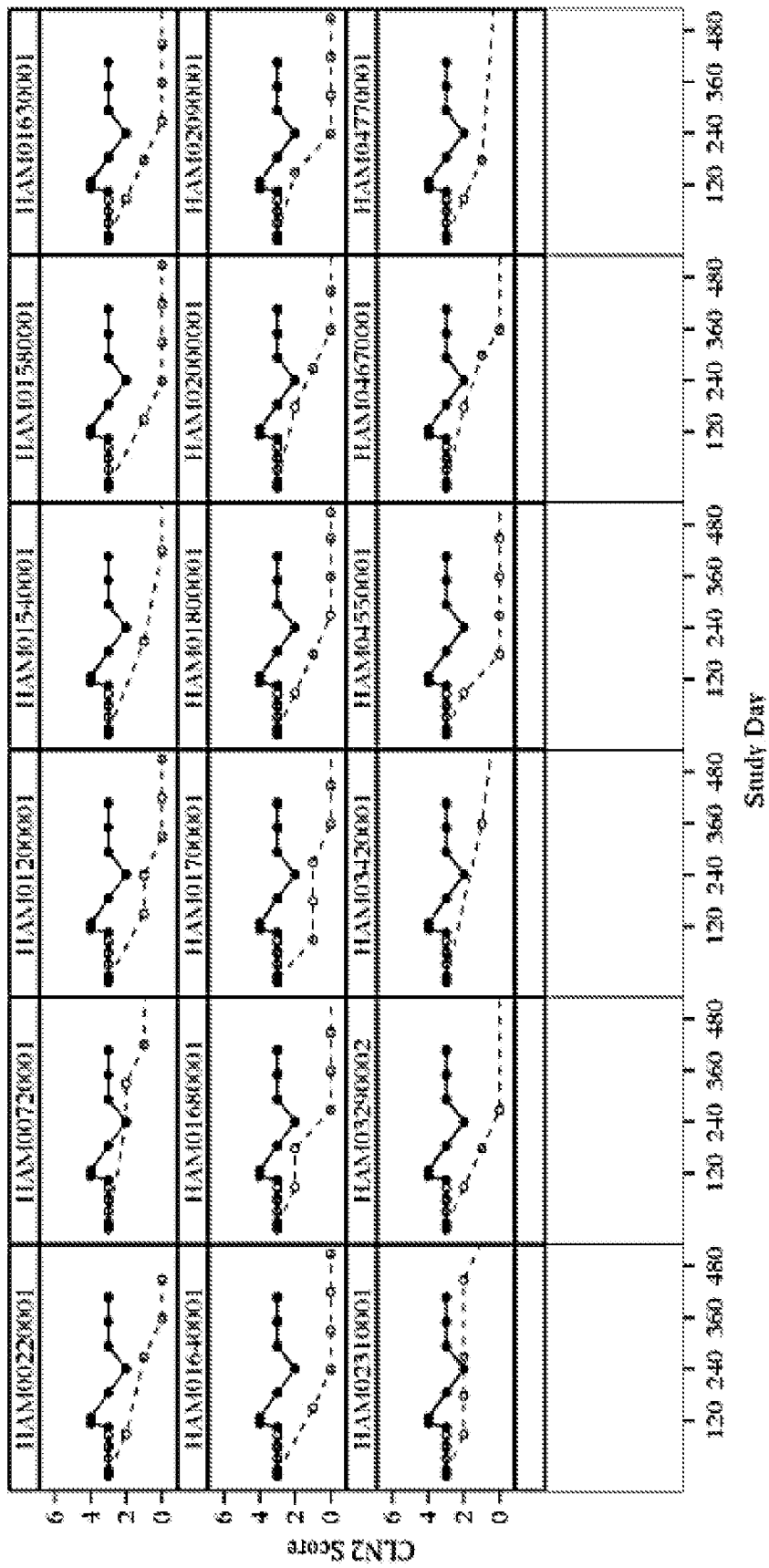
Figure 4C:
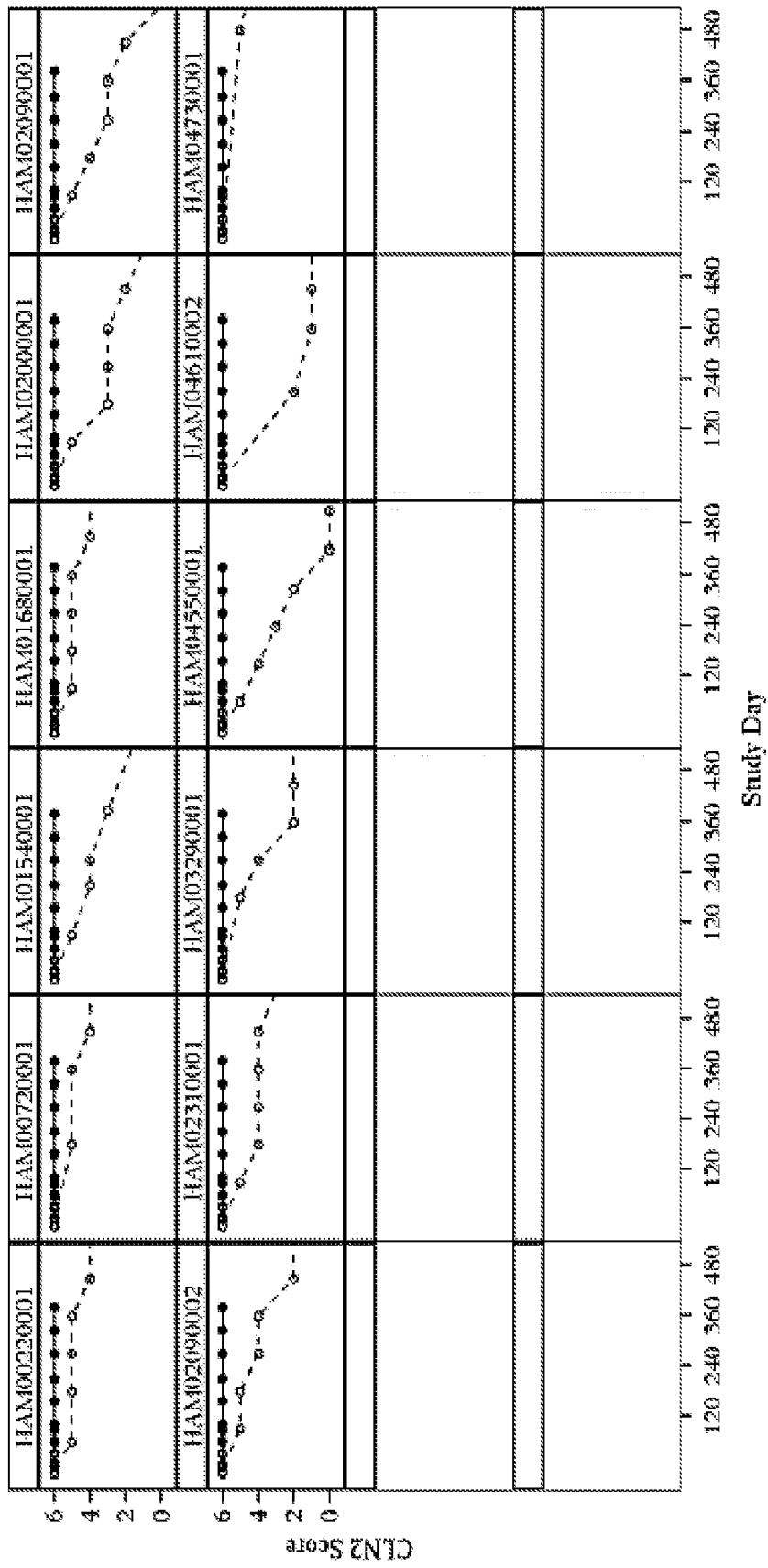
Figure 4D:
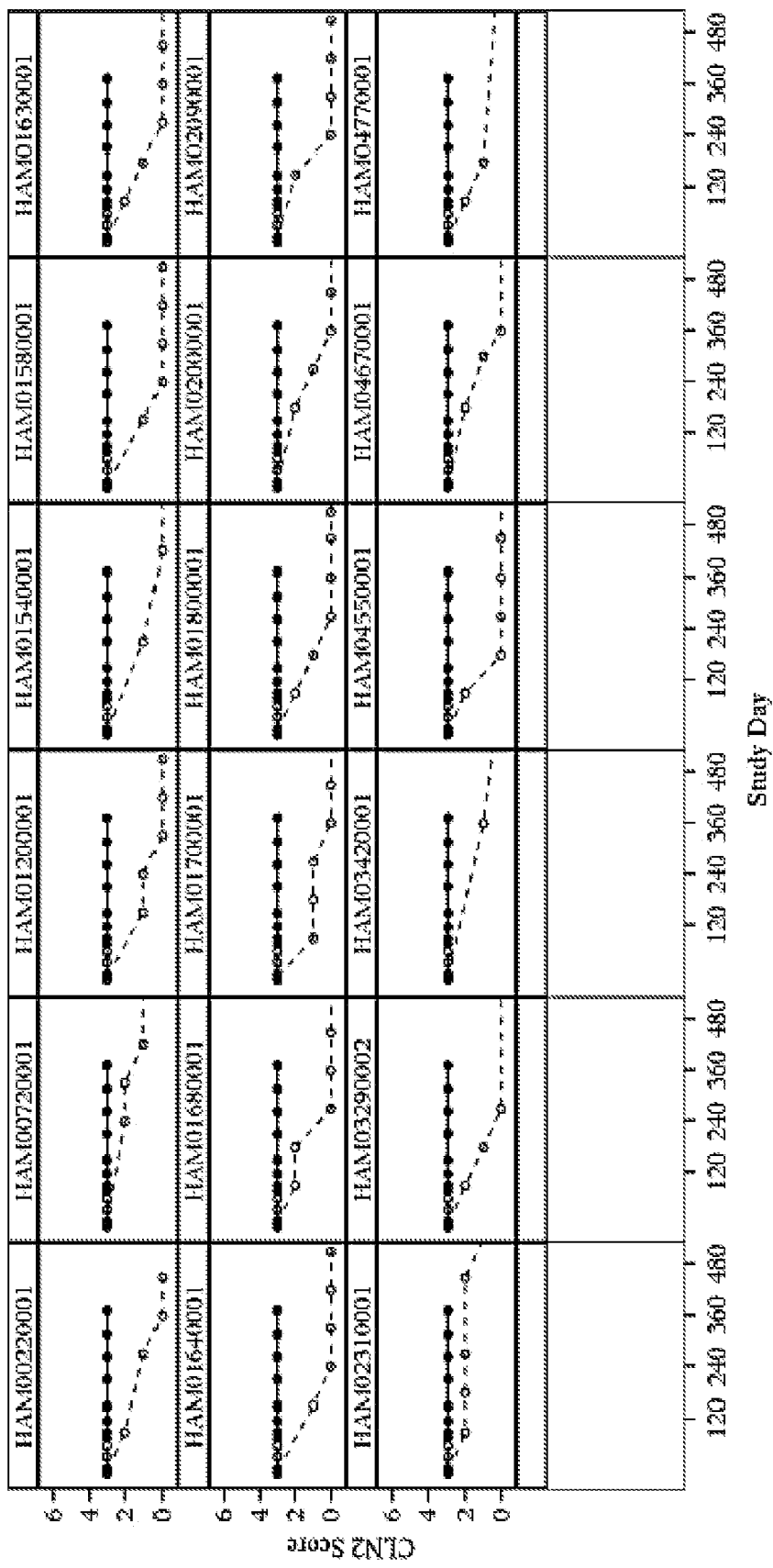
Figure 4E:
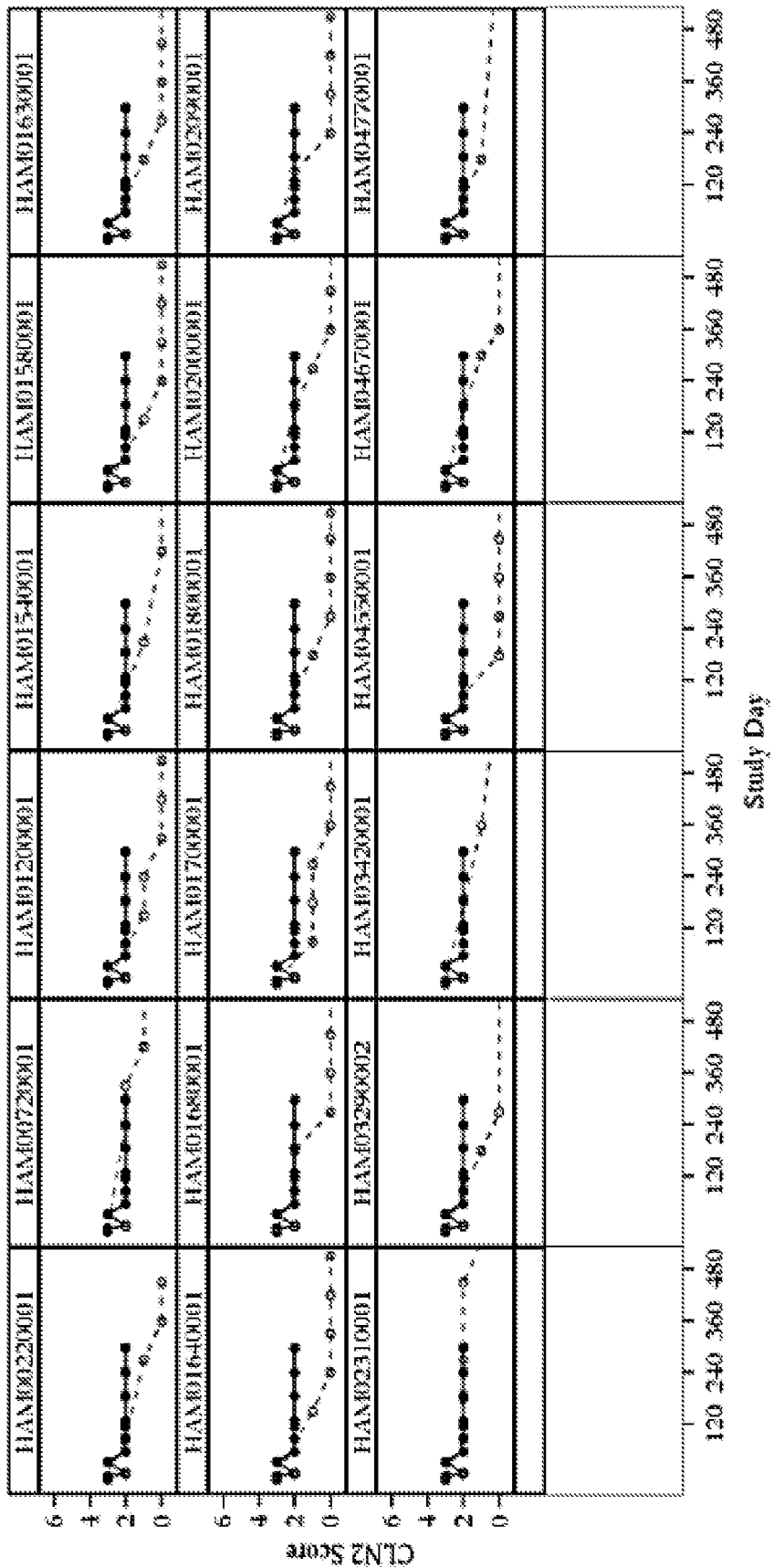
Figure 4F:
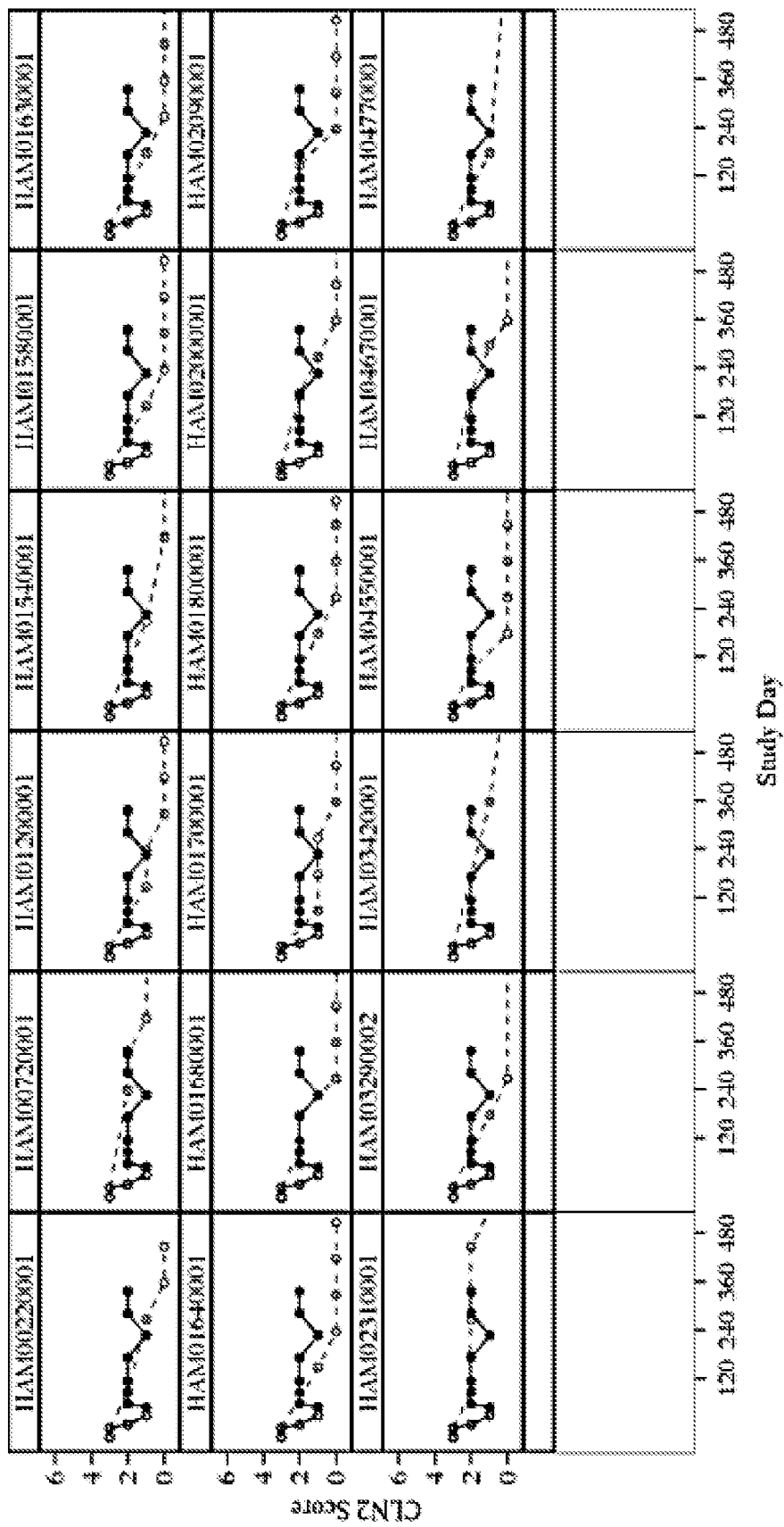
Figure 4G:
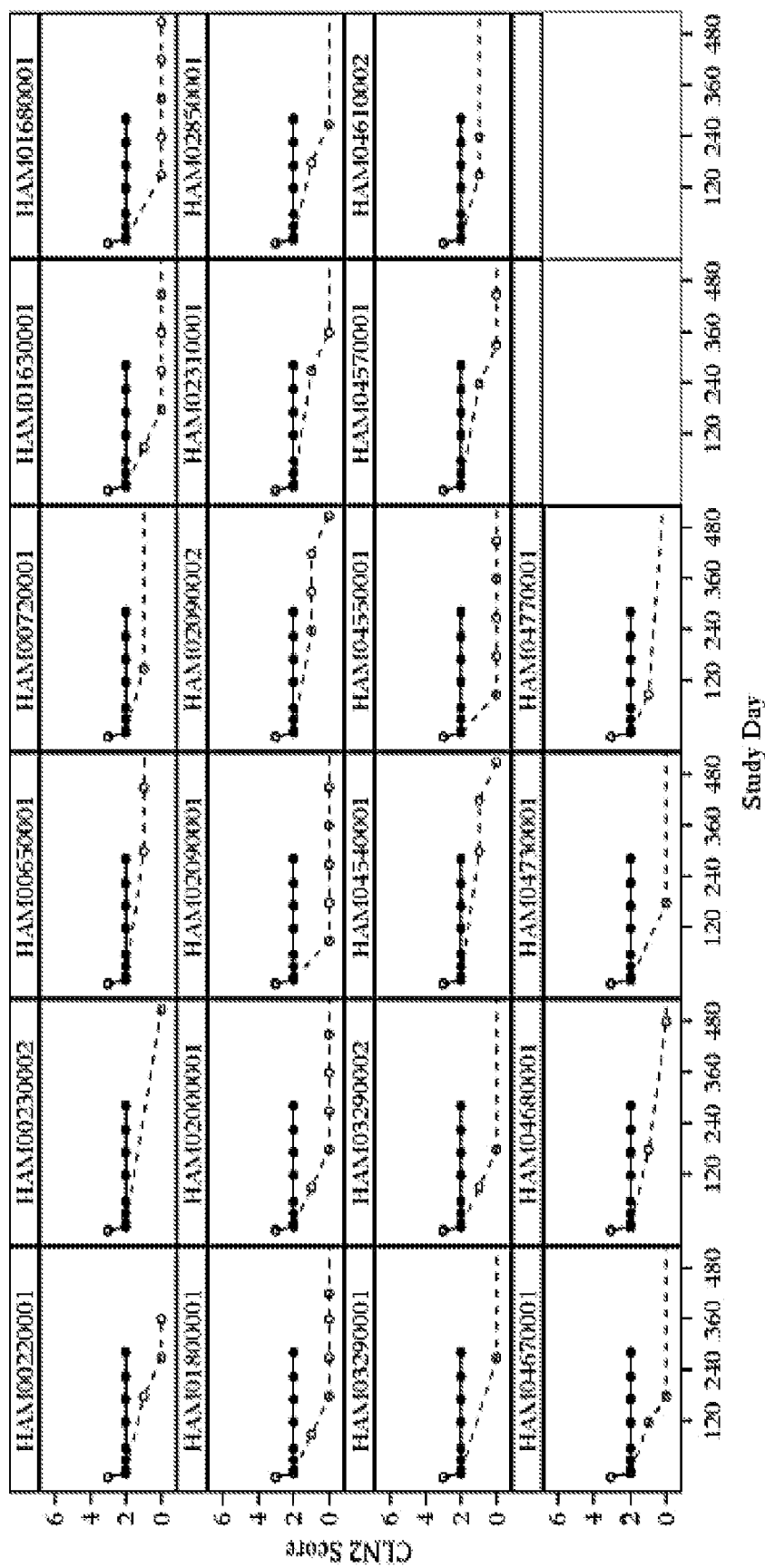
Figure 4H:
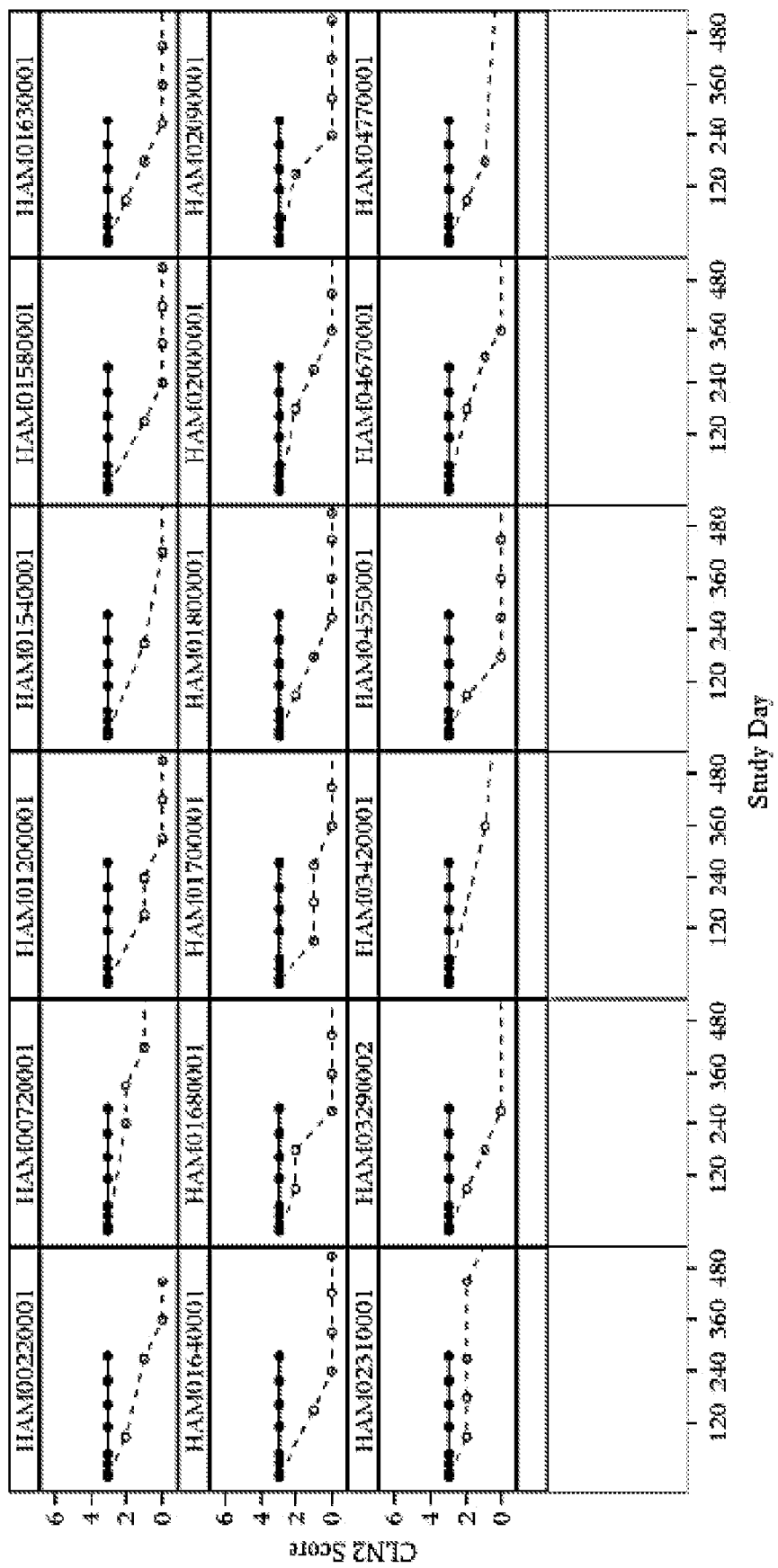
Figure 4I:
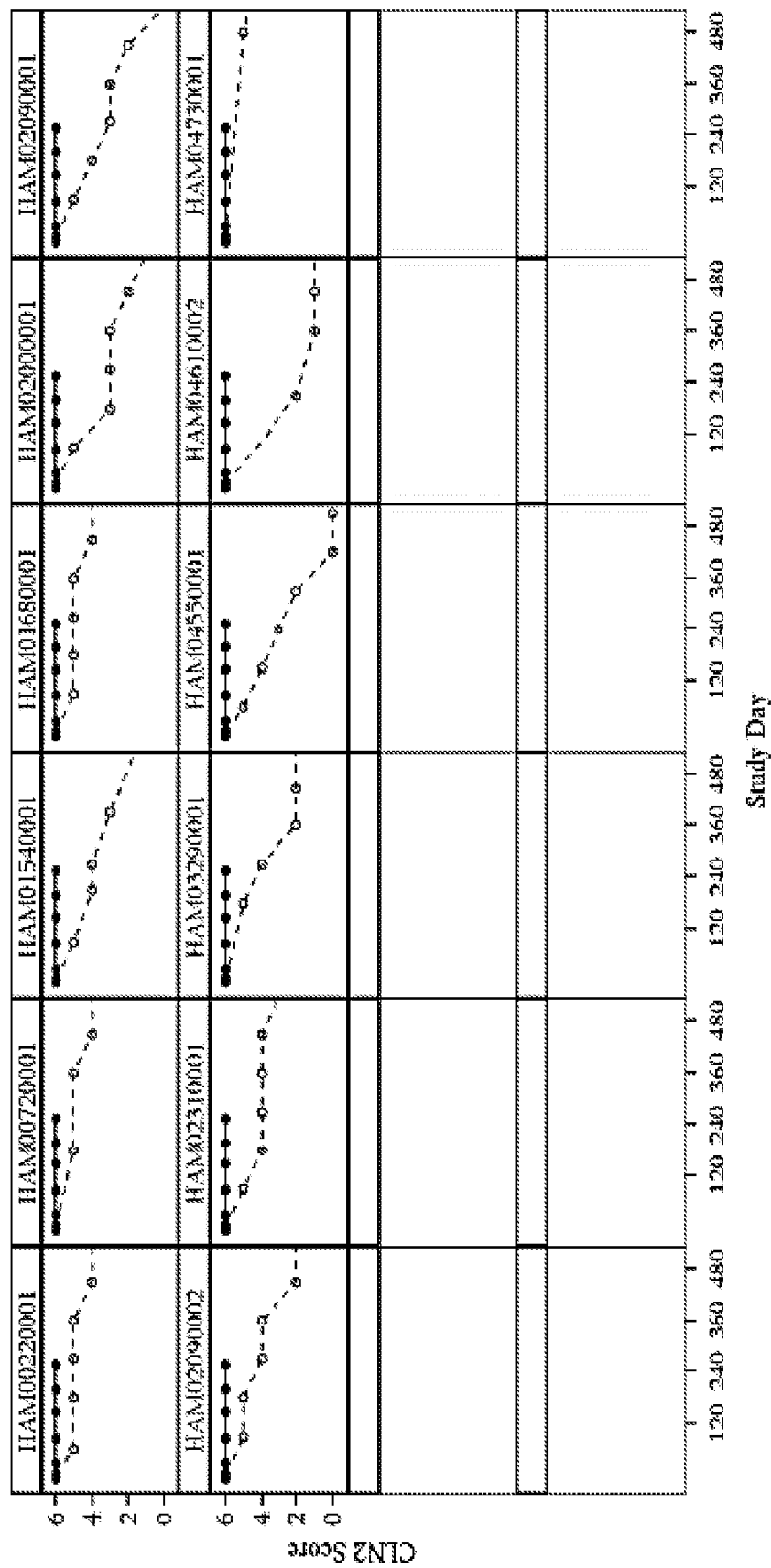

The most complicated response (Subject 1287-1005) is shown in FIG. 4F. Although this patient dropped rapidly by 2 units from a baseline score of 3 points to a study score of 1 in the first month of the study, the patient was able to regain a unit and stabilize at a score of 2 points. The interpretation of this course was clarified by comparison to score-matched untreated natural history patients. The clinical progress was worse in 15 of the 18 score-matched untreated natural history patients, and the same in just 2 score-matched untreated natural history patients (a single untreated natural history match was non-evaluable). The clinical course in untreated patients always was worsening, frequently with little time between lost milestones. There was never re-establishment of lost function and subsequent stabilization. Matching to the most complex treated profile was also indicative, therefore, of a clear treatment benefit.

Figure 5:
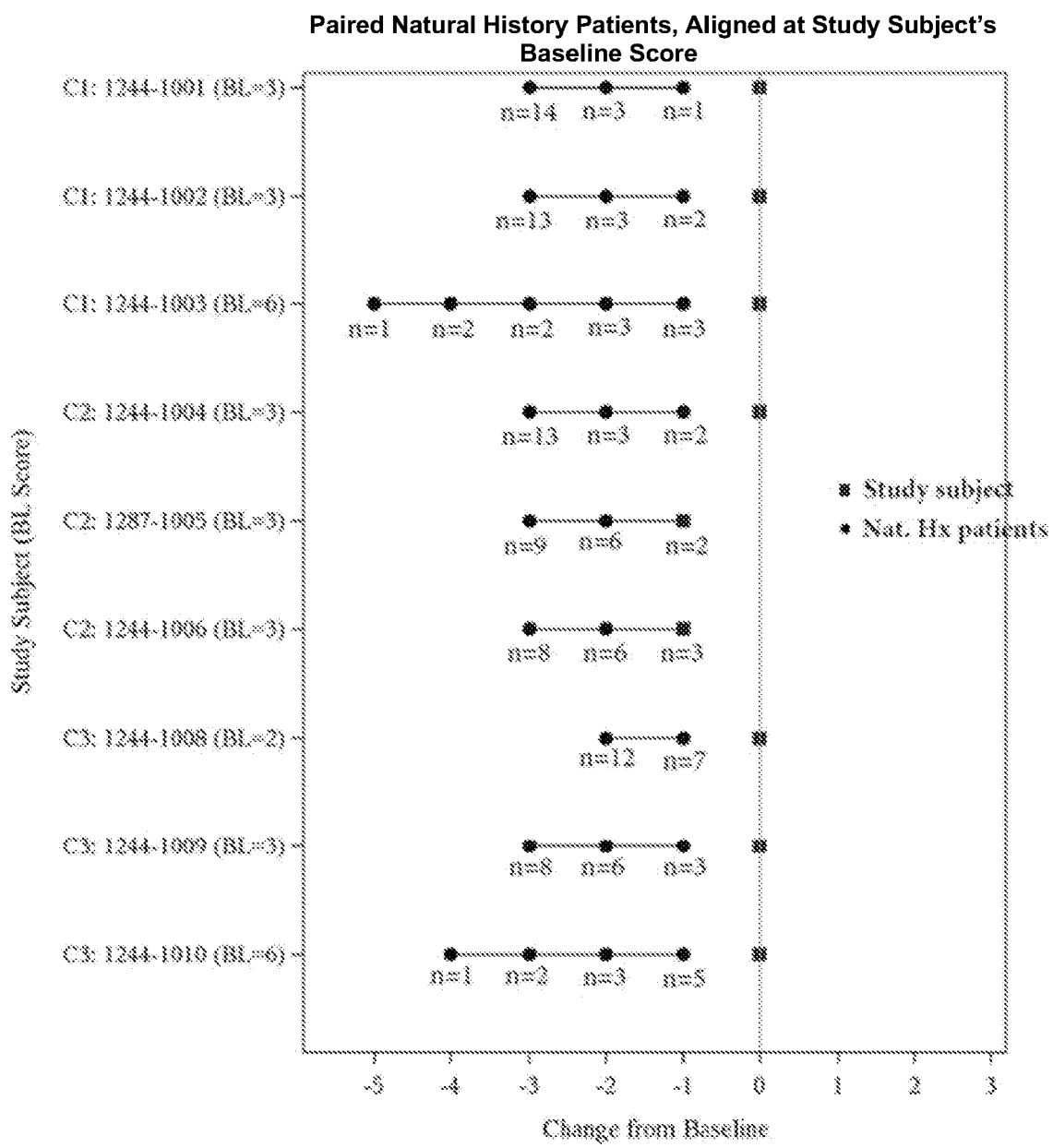
FIG. 5 depicts the distribution of clinical change from baseline for matched, untreated natural history patients (circles) for the treatment duration of the patient match compared to the study subjects (squares).
Figure 6A:
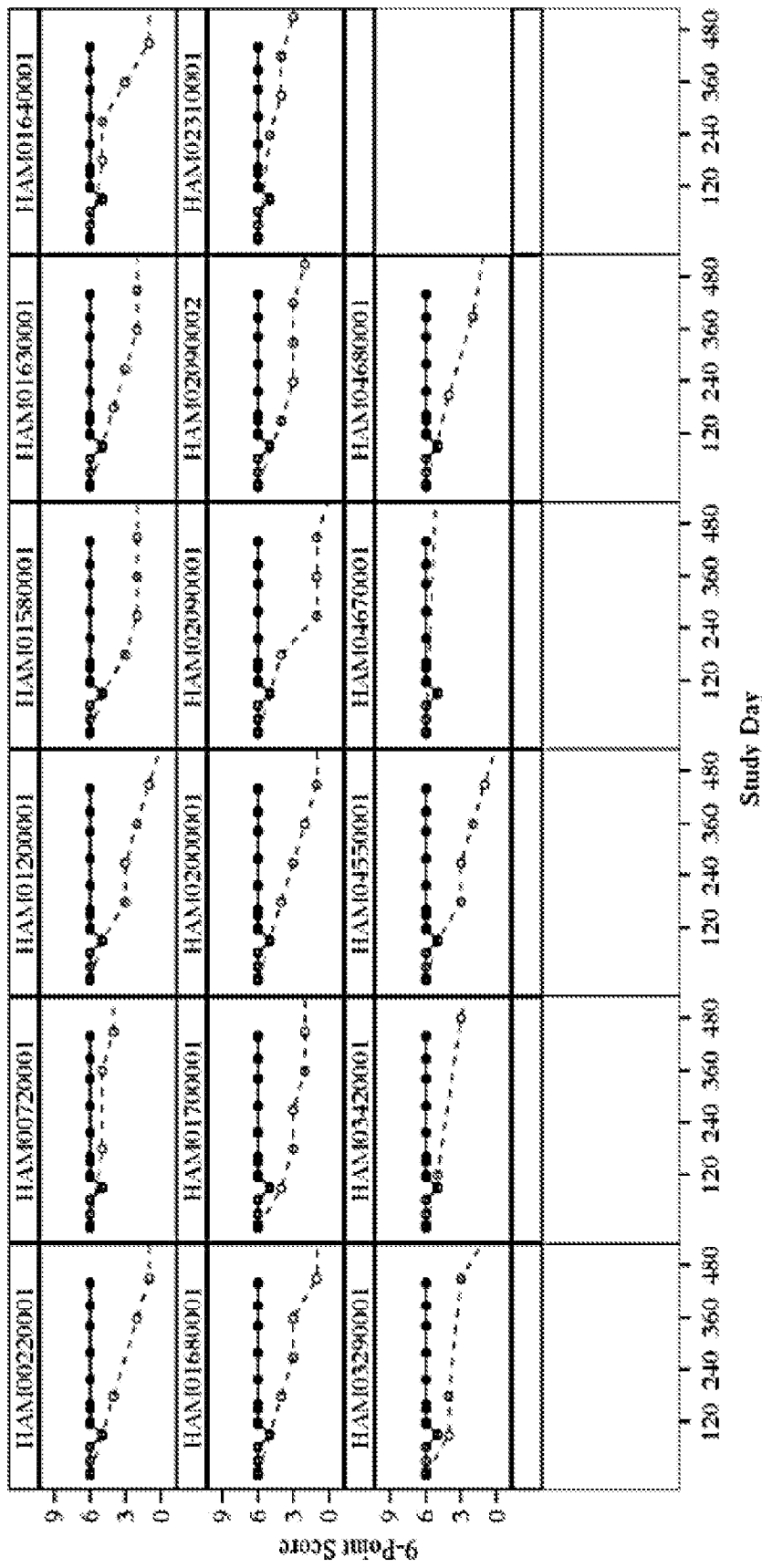
FIGS. 6A to 6I depict the change in CLN2 score from 9 patients treated with rhTPP1 to untreated natural history patients matched by disease rating score on the 0 to 9 Hamburg motor/language/vision aggregate scale. Results for the treated patients are shown with a solid line in each panel compared to results for matched, untreated natural history patients, which are shown with a broken line.
Figure 6B:
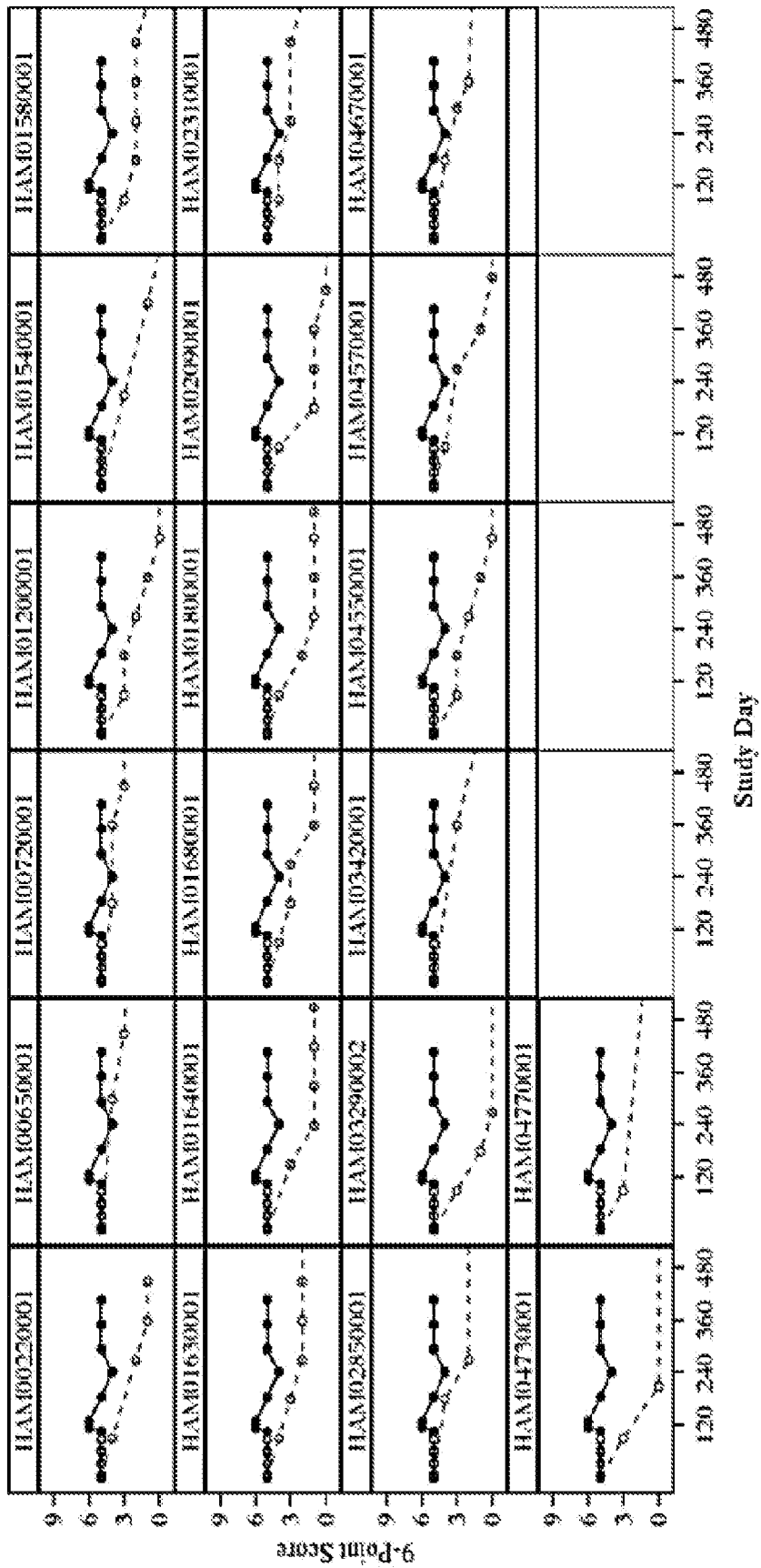
Figure 6C:
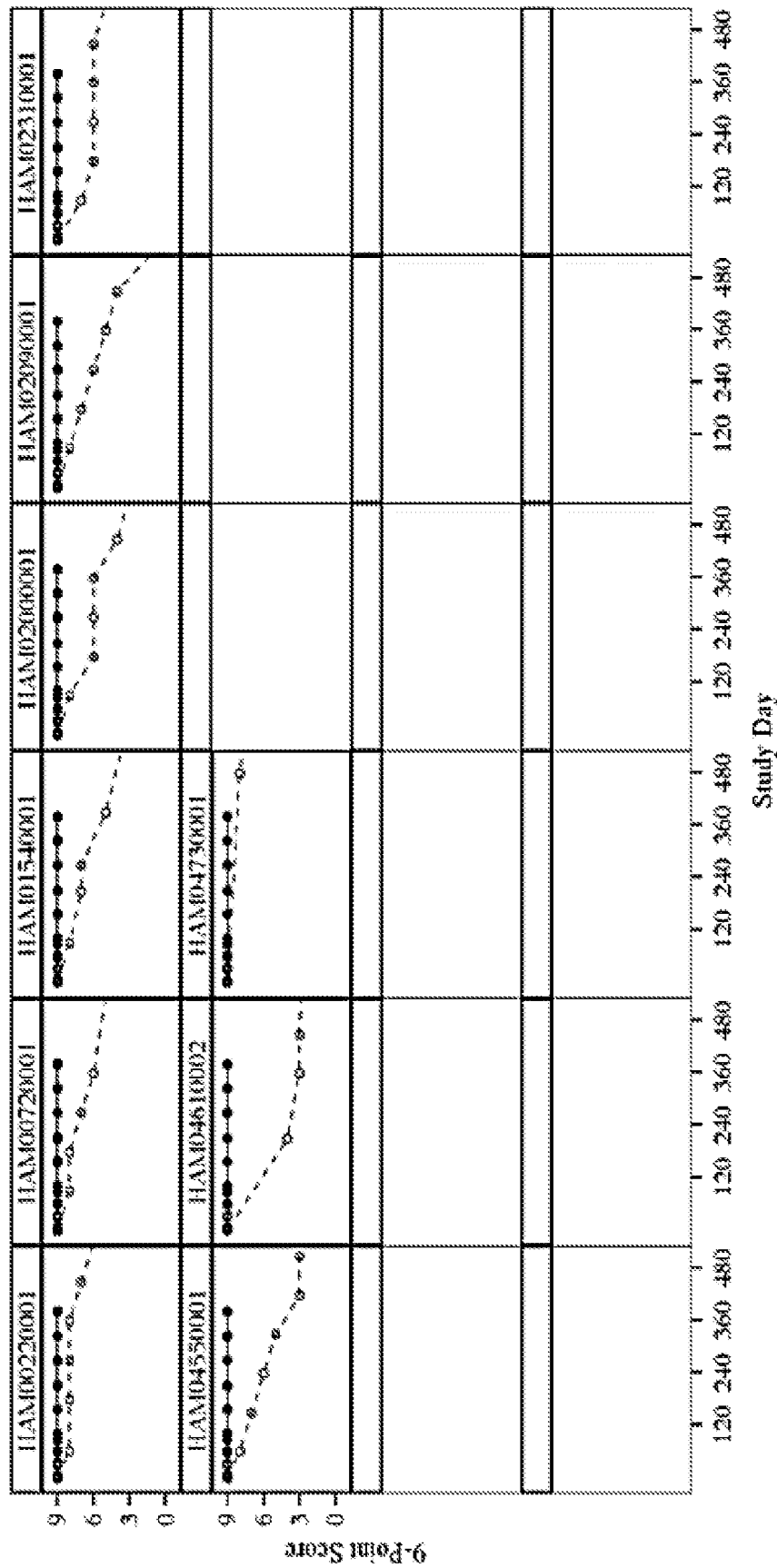
Figure 6D:
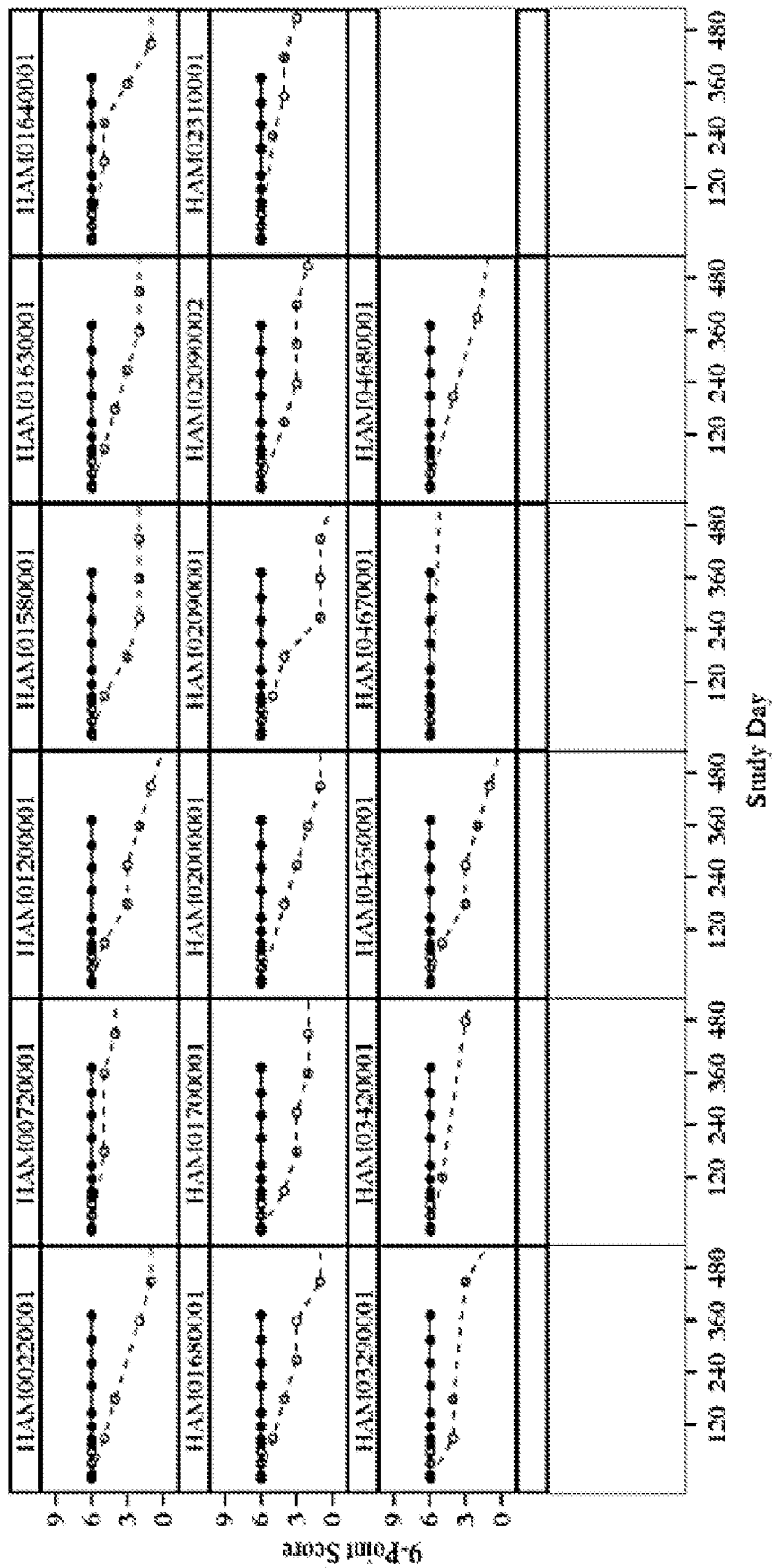
Figure 6E:
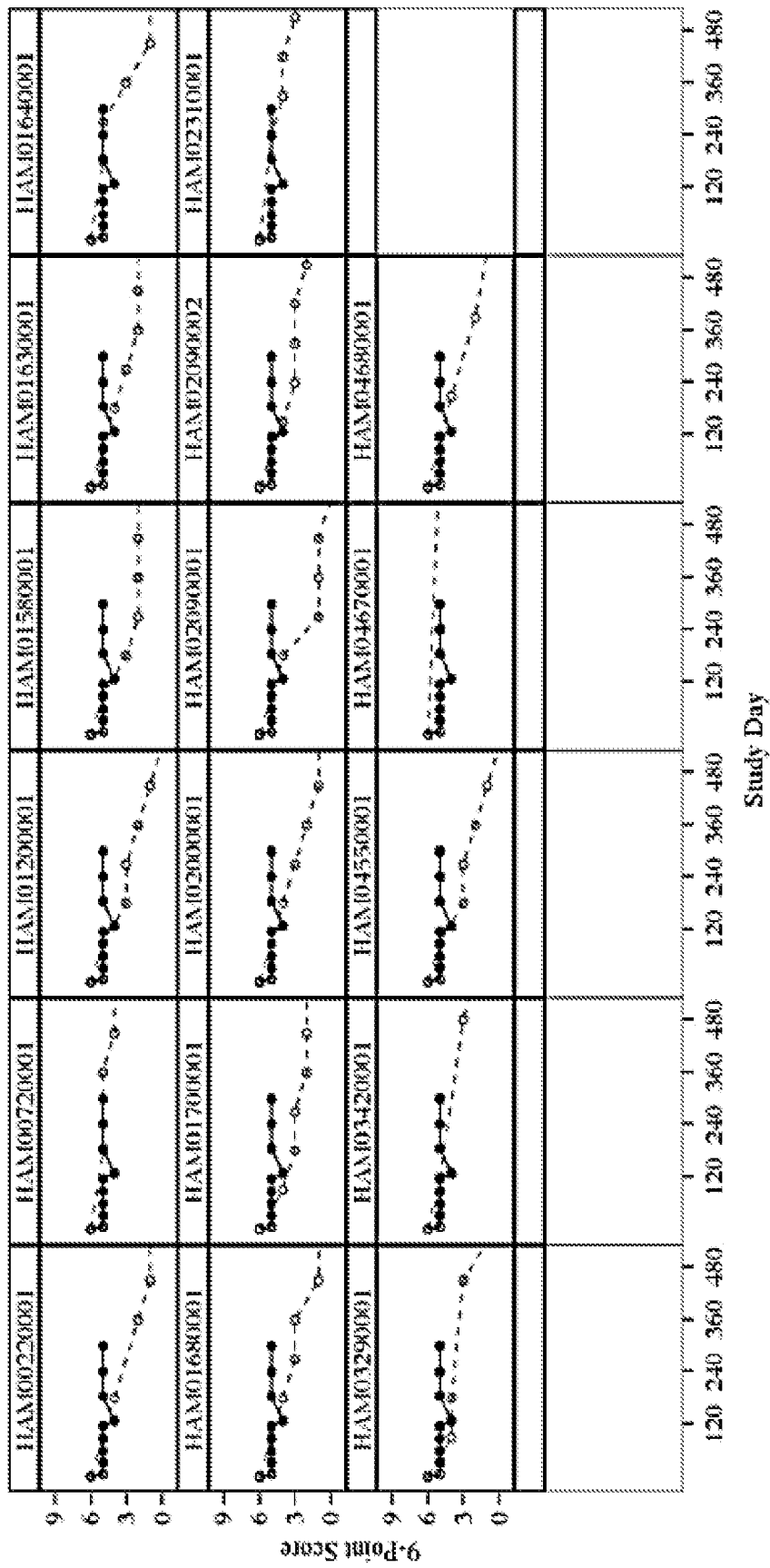
Figure 6F:
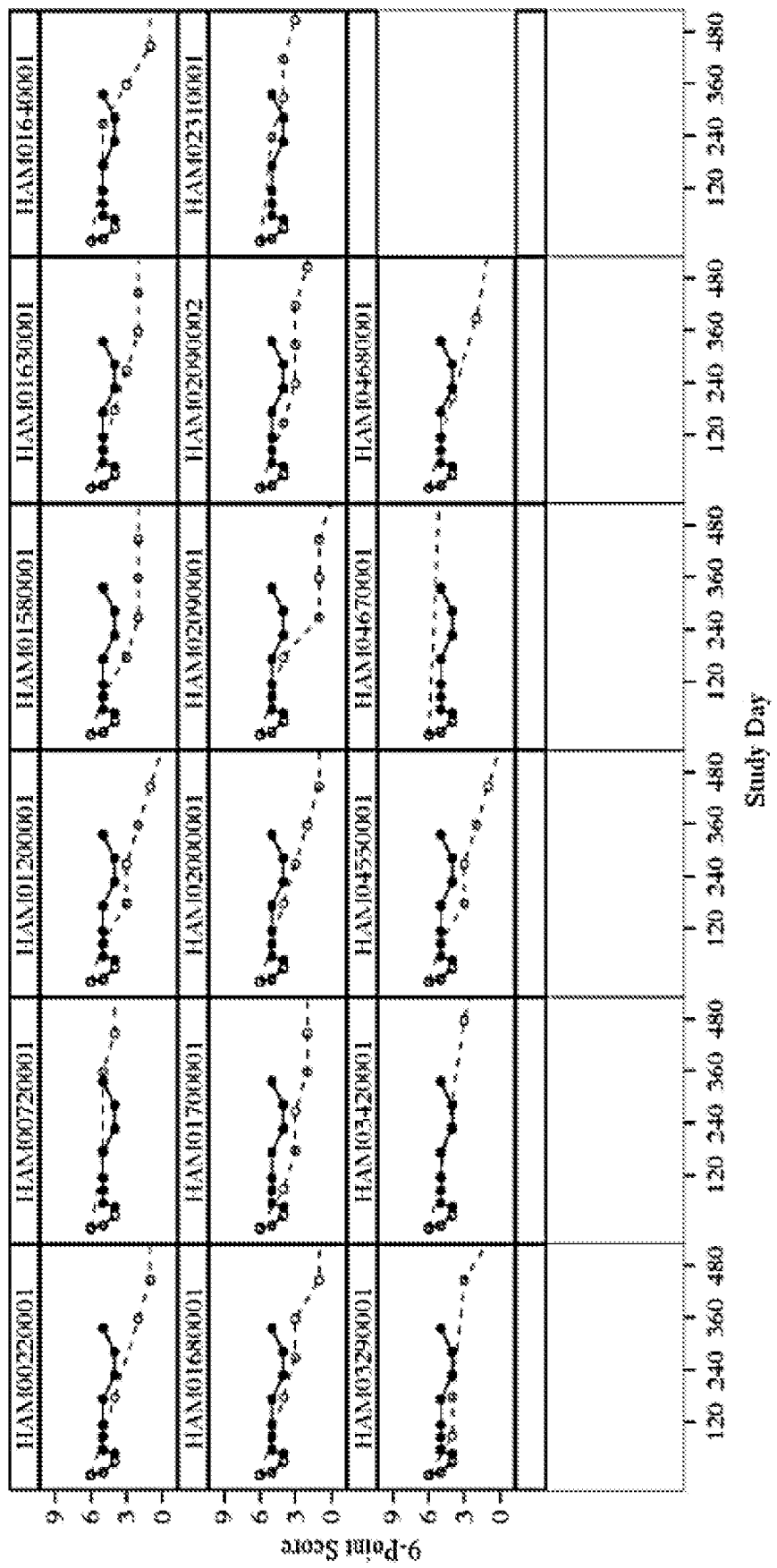
Figure 6G:
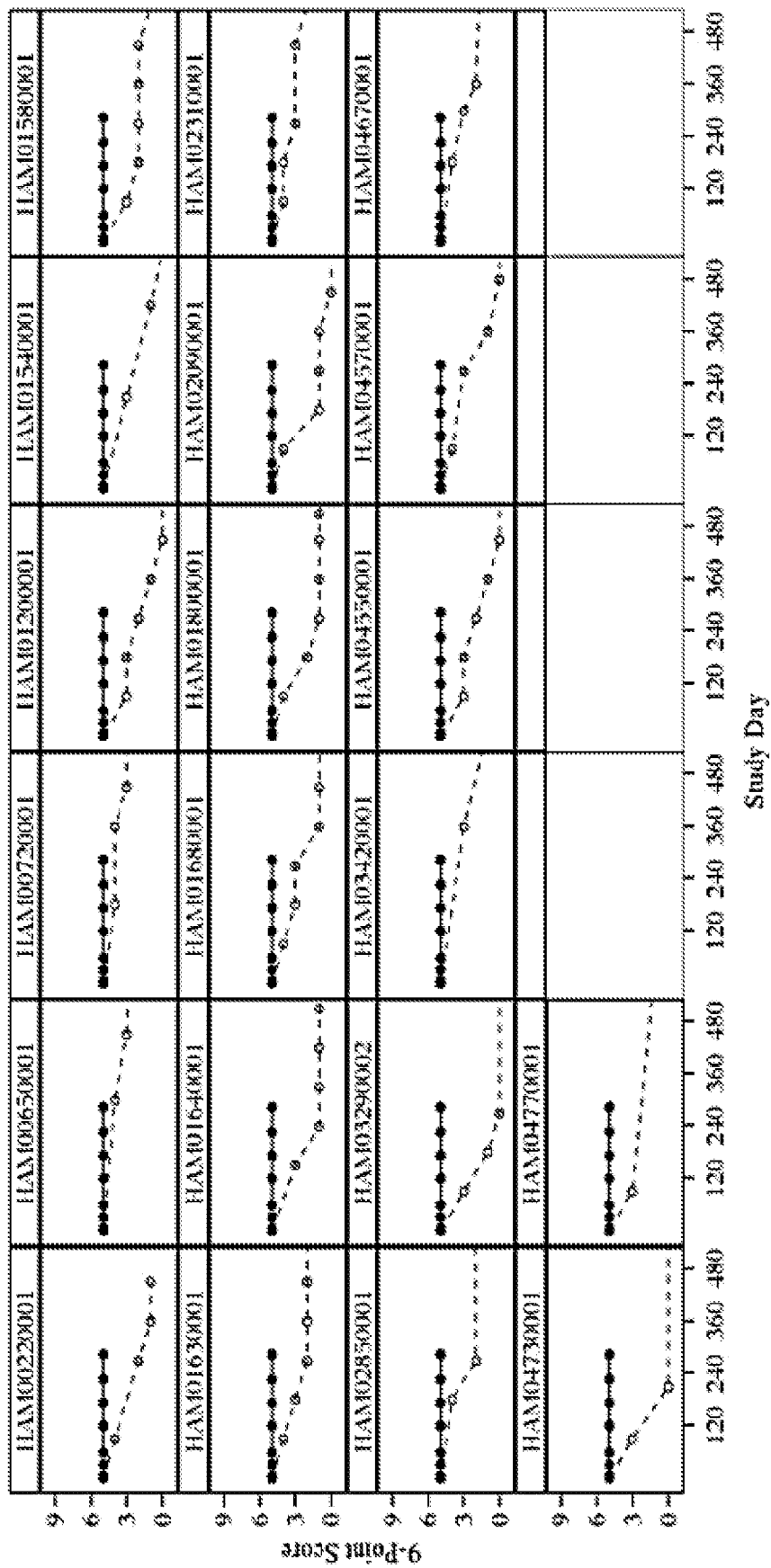
Figure 6H:
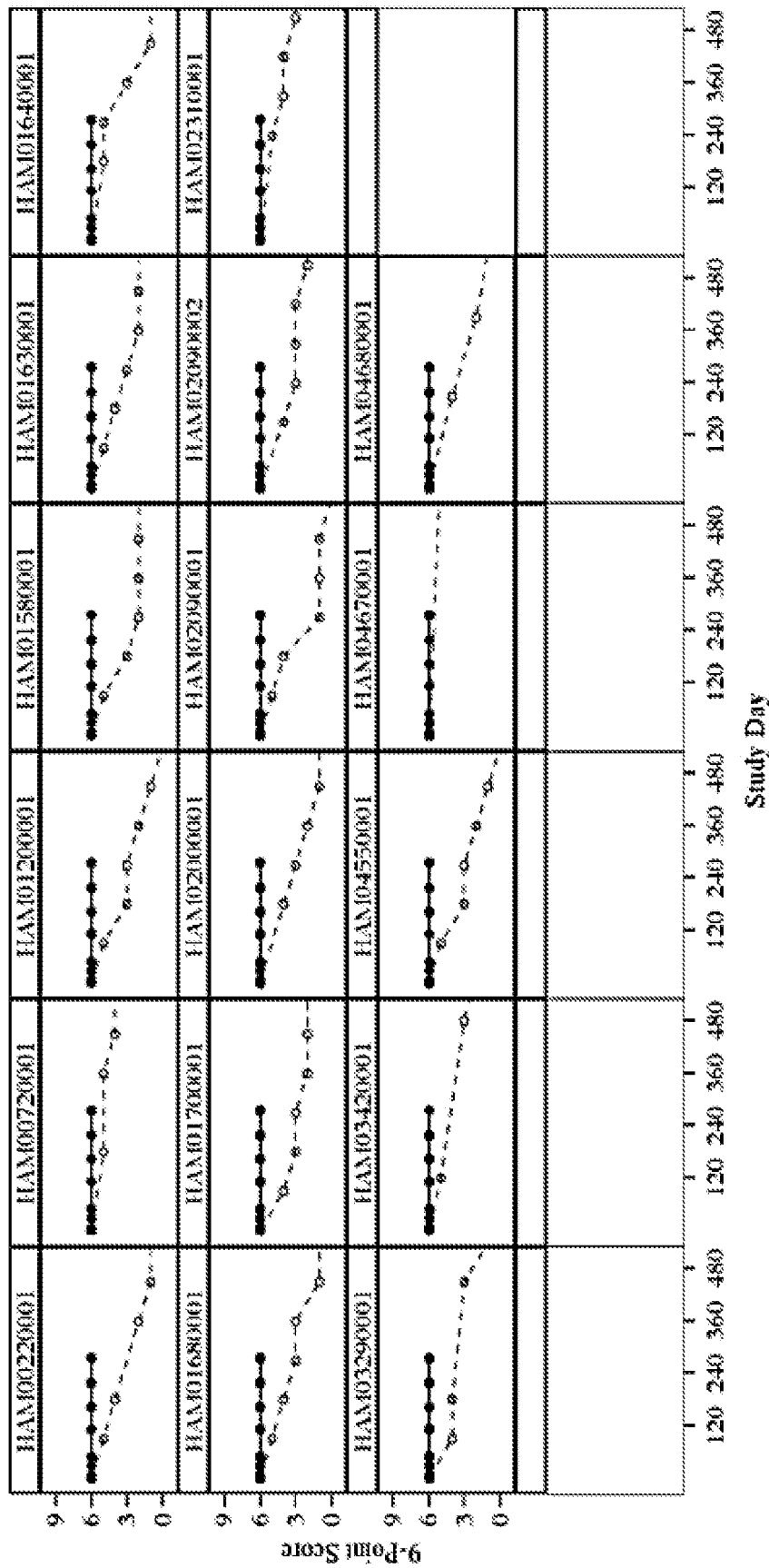
Figure 6I:
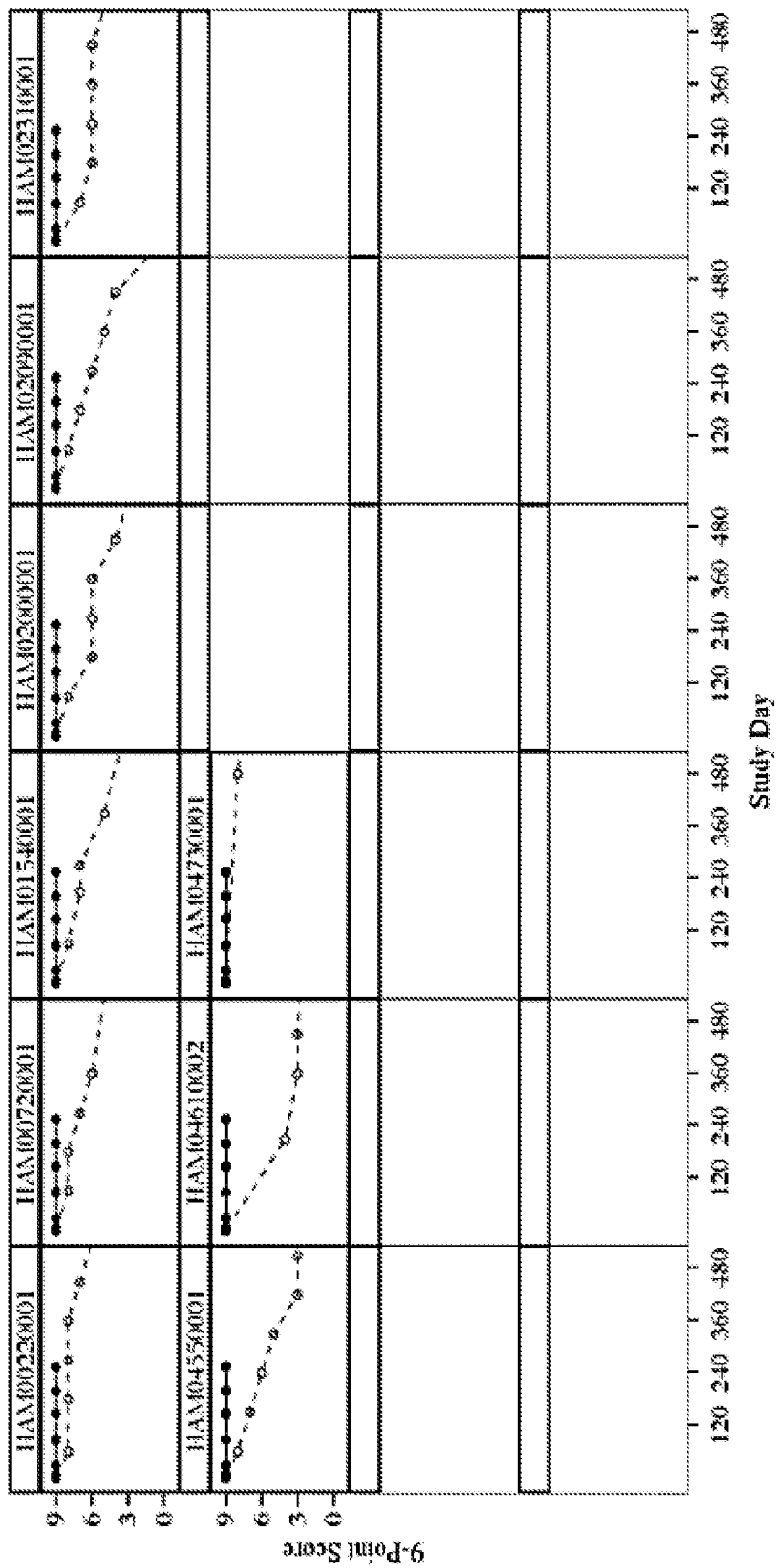

FIG. 5 displays the distribution of clinical change from baseline in matched, untreated natural history patients for the treatment duration of the patient match compared to the study subjects. As previously stated, 7 of 9 (>75%) patients had no change in baseline disease rating scale. For those 7 patients in the treatment period, all matched untreated natural history patients had at least a single unit decline, but more common was a multiple unit decline or 2 units to 4 units. As an example, Patient 1244-1001 had 1 match that lost a single point, 3 matches that lost 2 points and 14 matches that lost all 3 available language/gait disease rating points. Therefore, in the same period of time, there was no change in the treated patient, but 14 of 18 (>75%) matched untreated natural history patients lost all gait and language function. There was a floor effect with a baseline entry score of 3 points in which many matched untreated natural history patients lost all available rating units, however, the 2 patients with entry scores of 6 points (Patients 1244-1003 and 1244-1010) importantly showed these matches also were actively deteriorating, some with 4 and 5 point declines in the treatment period. This observation was a clear clinical demonstration of substantial treatment effect; most treated children retained entry clinical ratings in the context of untreated natural history matches that actively lost language and independent gait in the same time period, many to complete loss of function. The remaining 2 treated patients that lost a single point (Subjects 1287-1005 and 1287-1006) still had better clinical ratings than the vast majority of matches in the treatment period. In total, of the score-matched untreated natural history patients, 97% had worse ratings than the treated subjects.

Using multiple matching criteria (e.g., baseline, age, and genotype), nearly 100% of comparisons showed a favorable treatment effect compared to matched untreated natural history patients. The average treatment difference across matching criteria in all treated patients as compared to natural history patients ranged from 1.9 to 2.1 points depending on the matching criteria utilized.

Figure 9A:
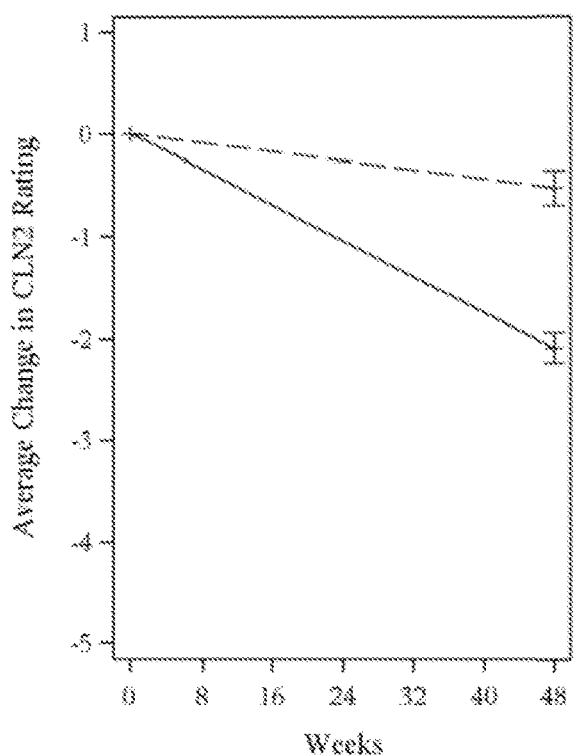
FIGS. 9A and 9B depict the average change in CLN2 score for patients treated with rhTPP1 and untreated natural history patients.
Figure 9B:
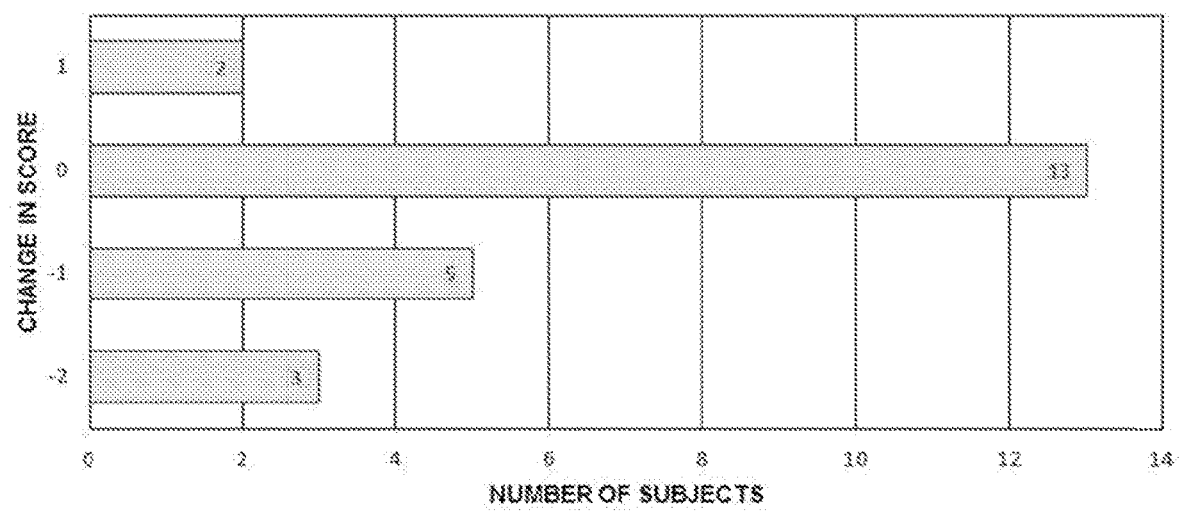
Figure 10A:
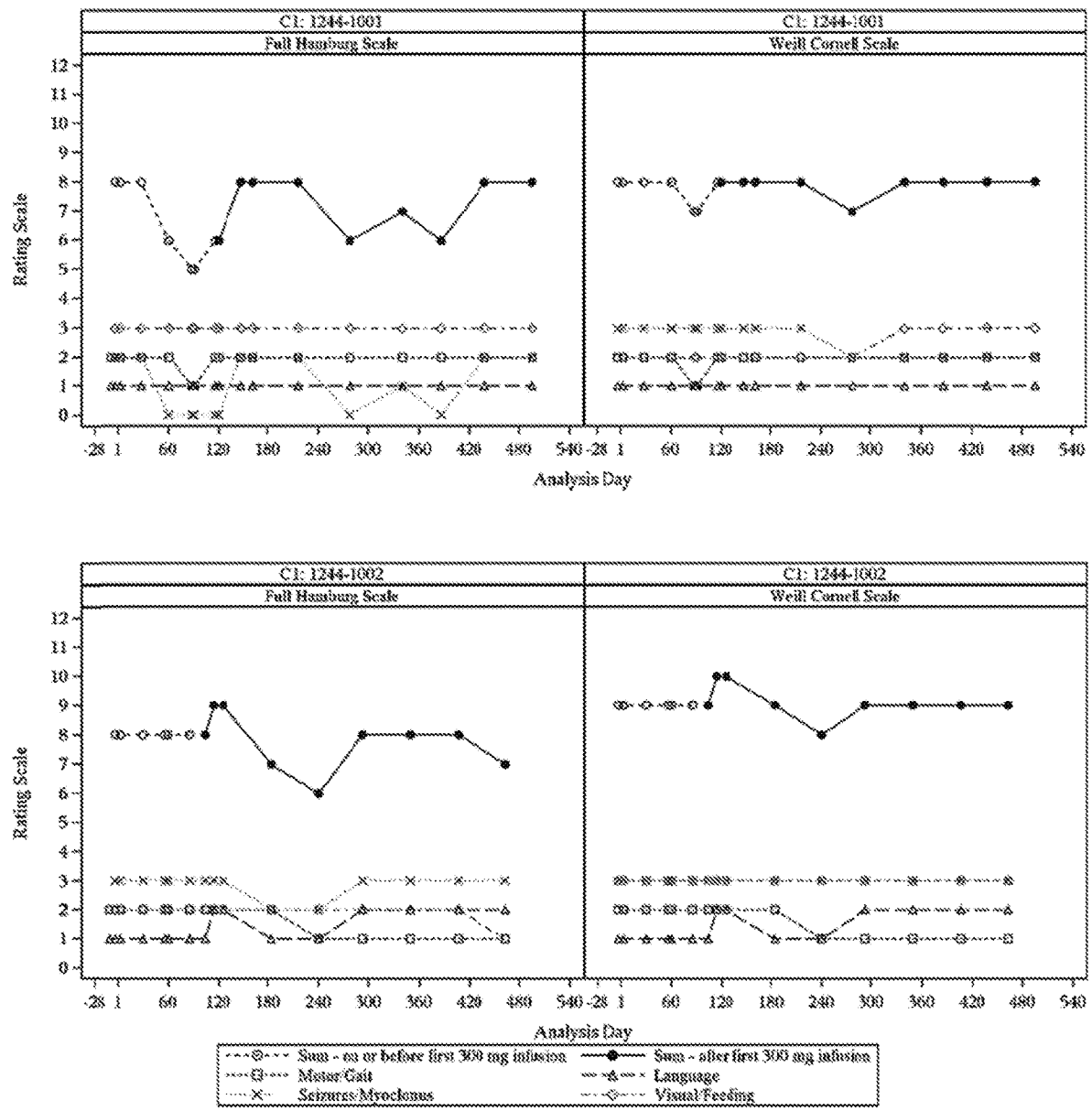
Figure 10B:
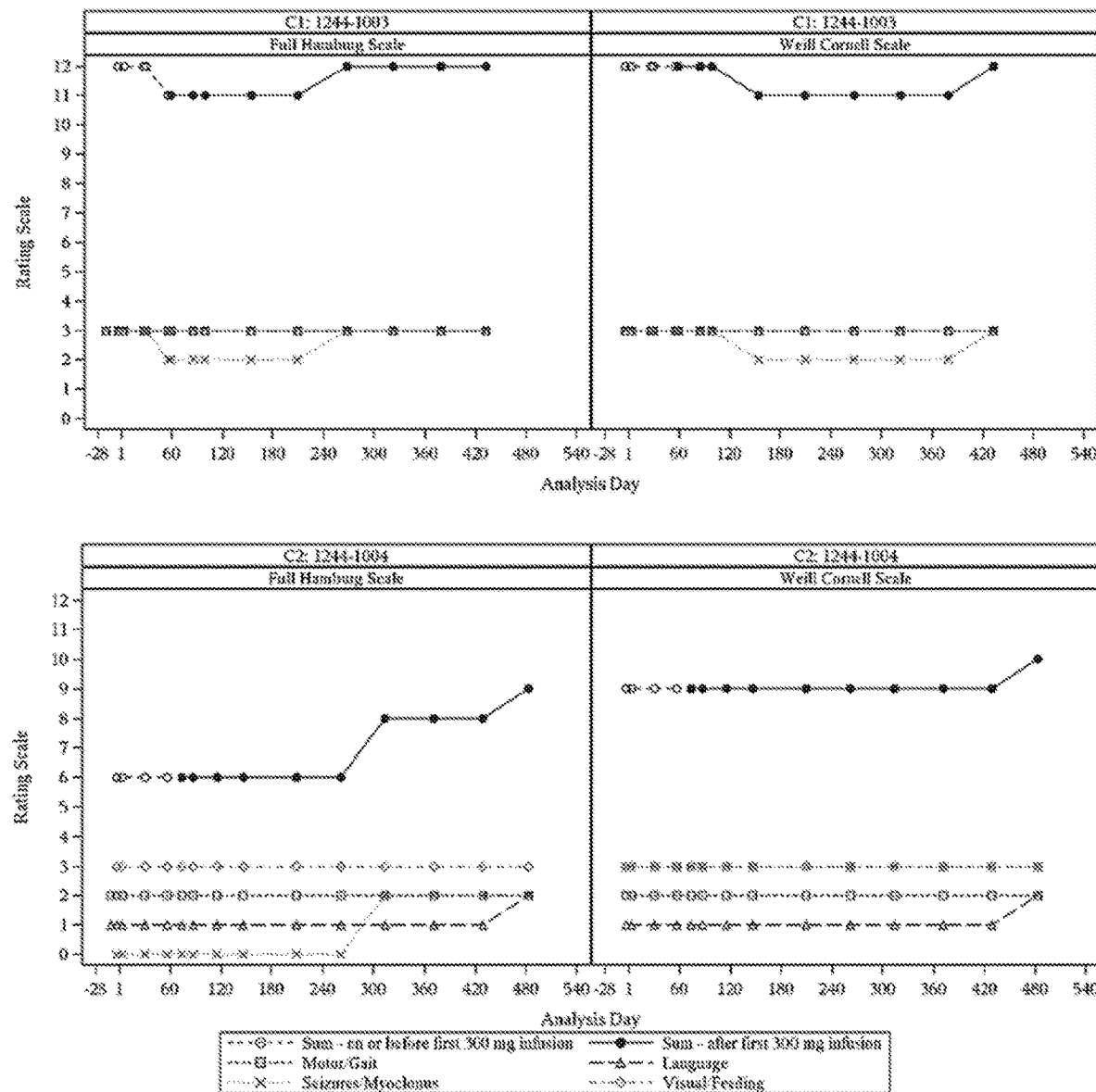
Figure 10C:
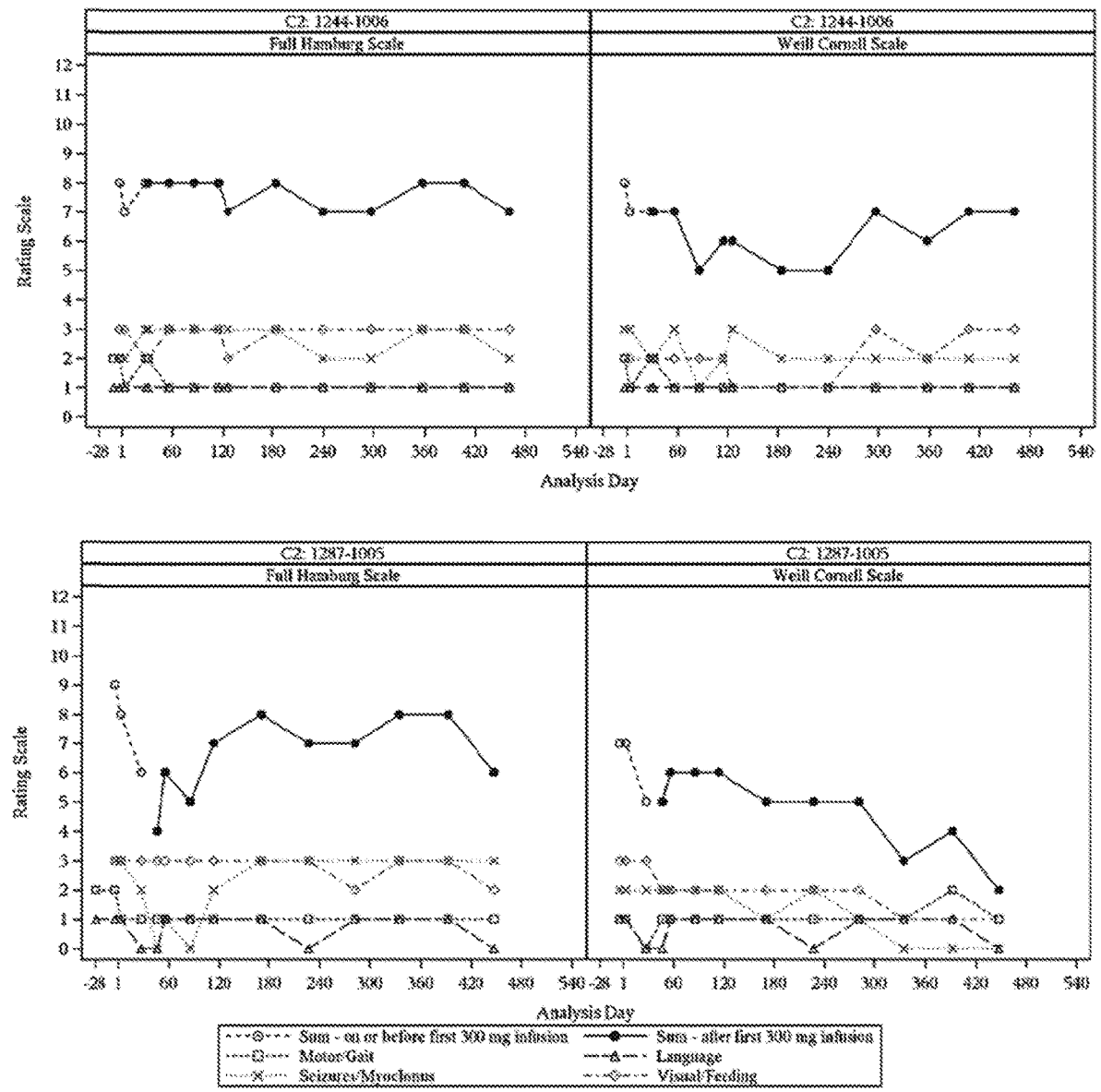
Figure 10D:
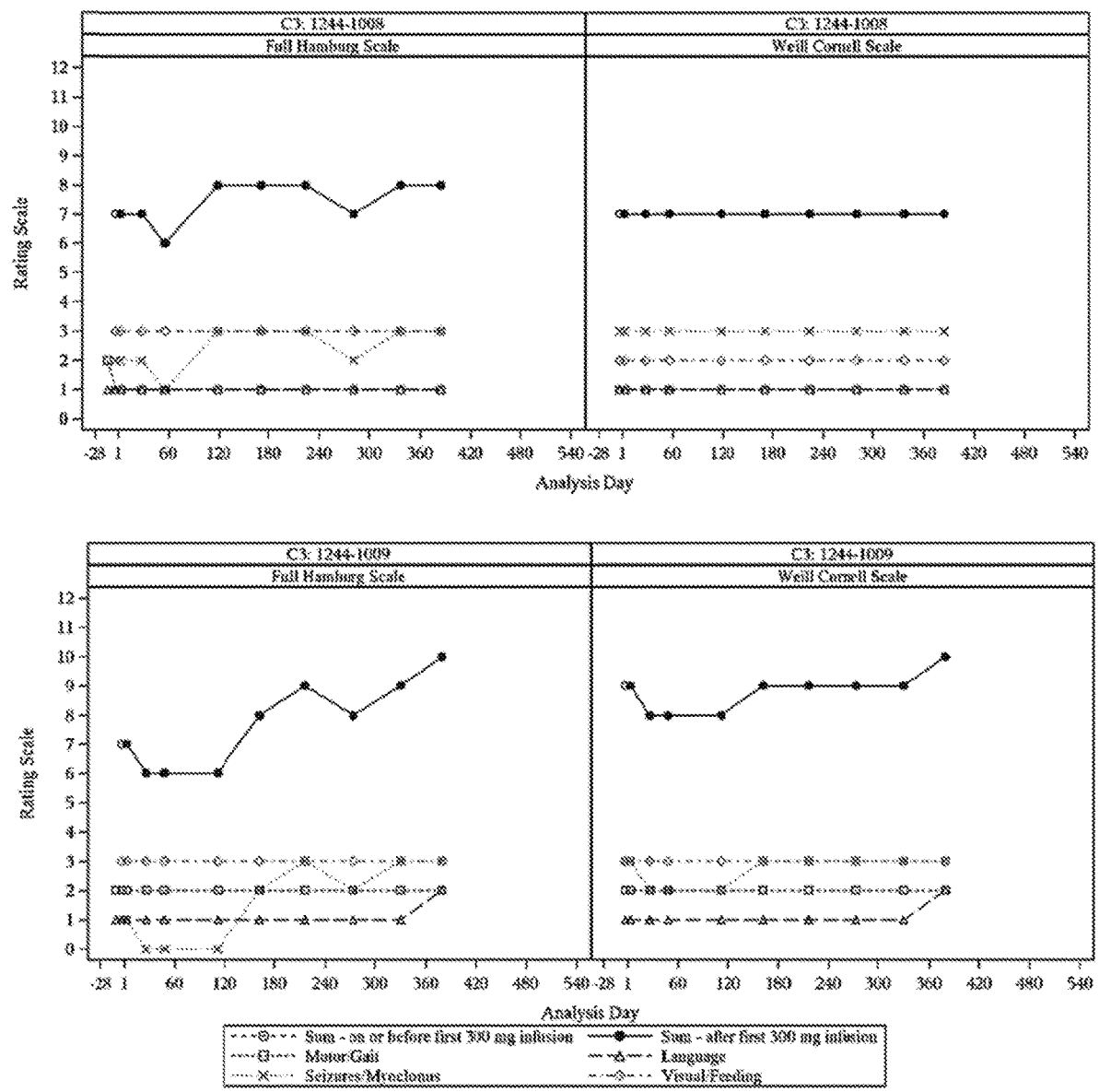
Figure 10E:
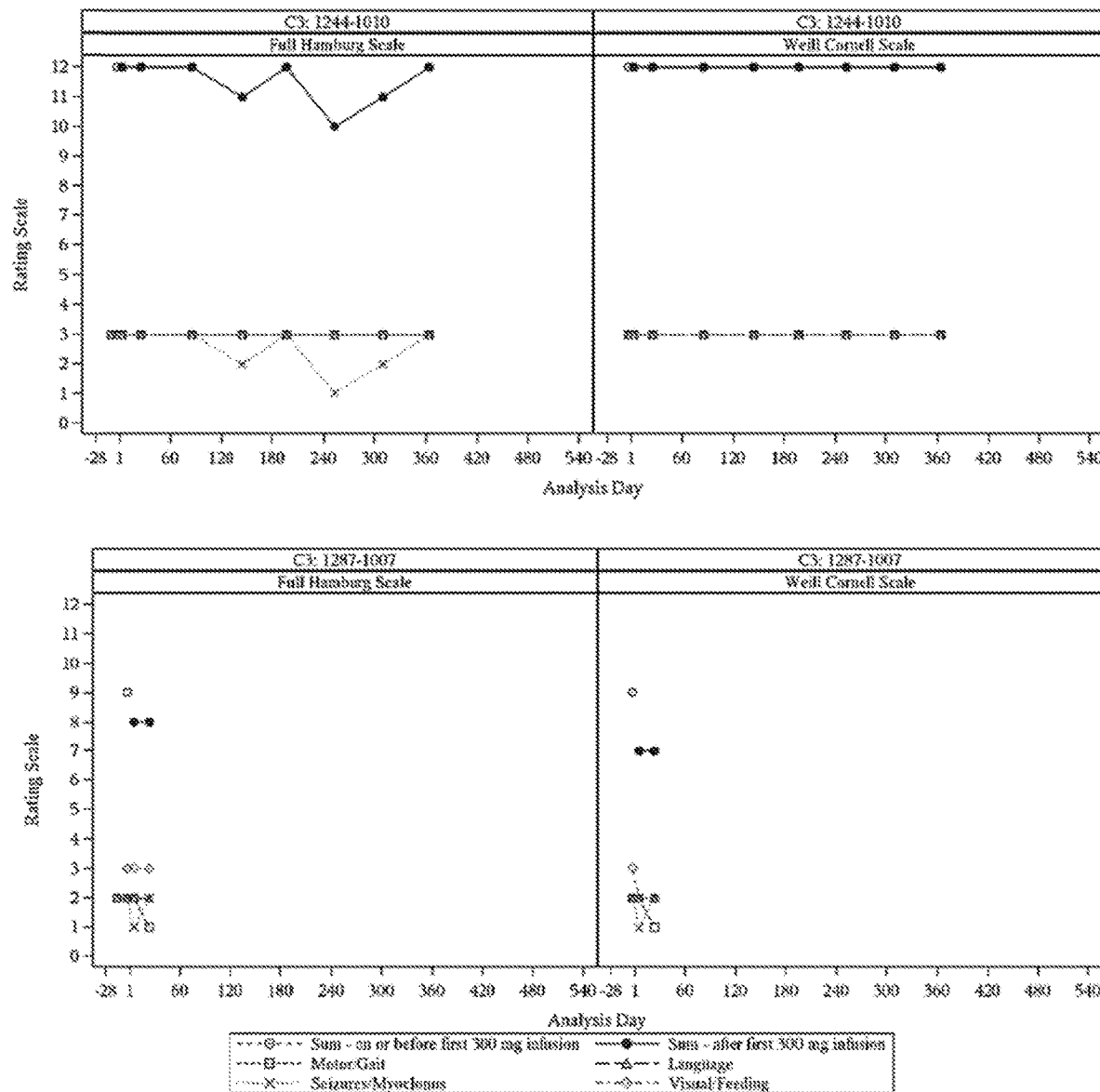
Figure 10F:
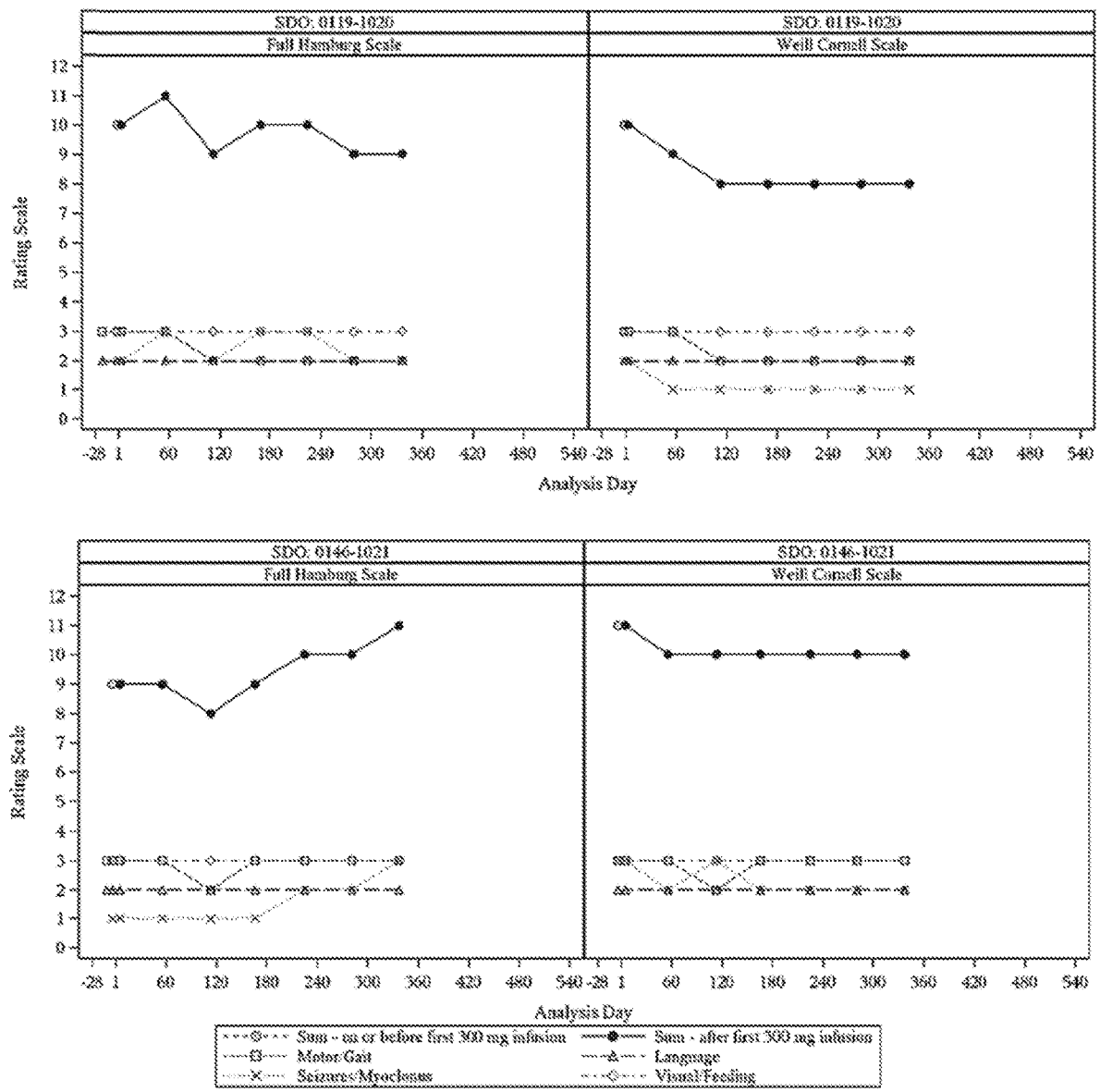
Figure 10G:
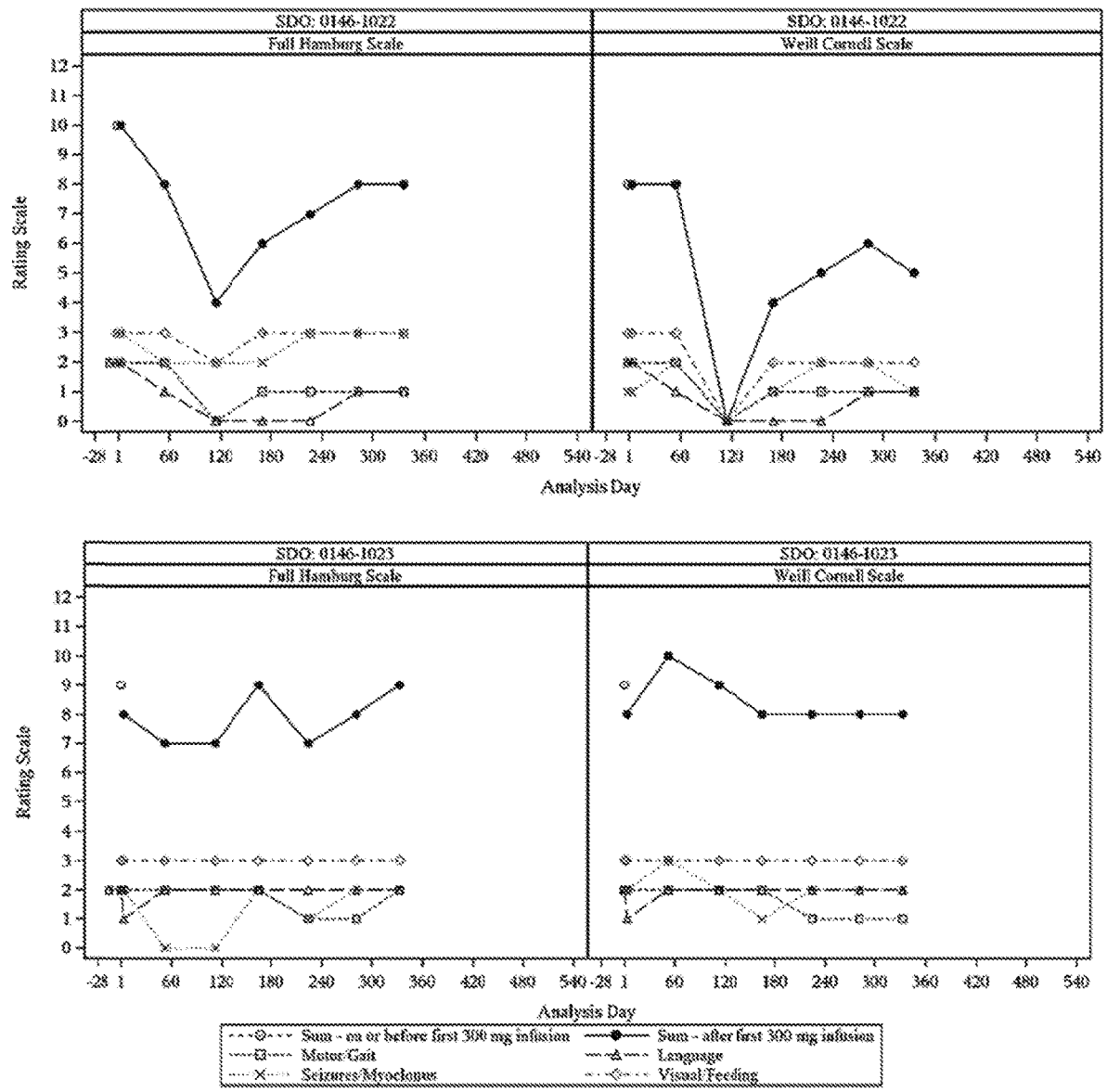
Figure 10H:
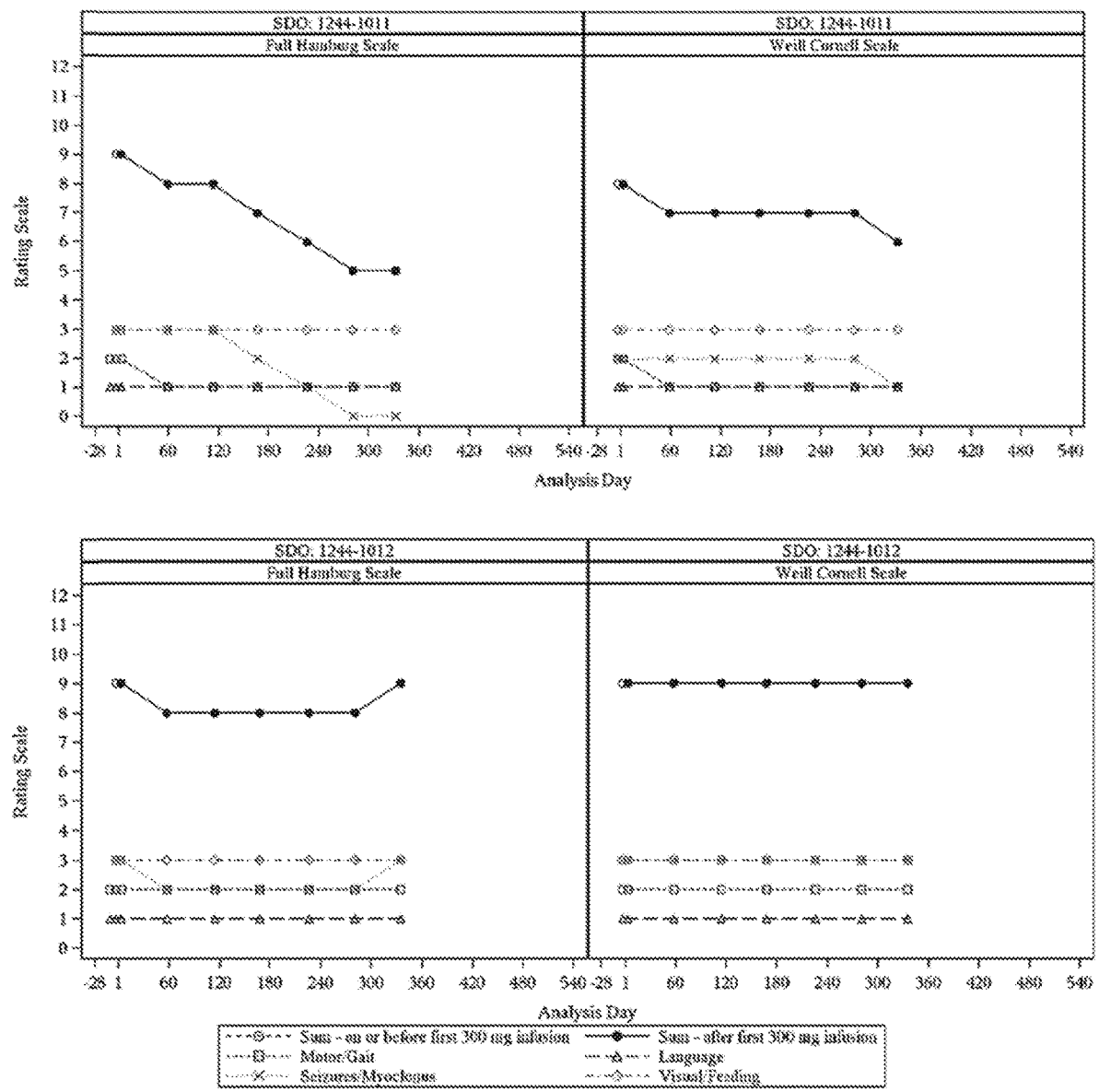
Figure 10I:
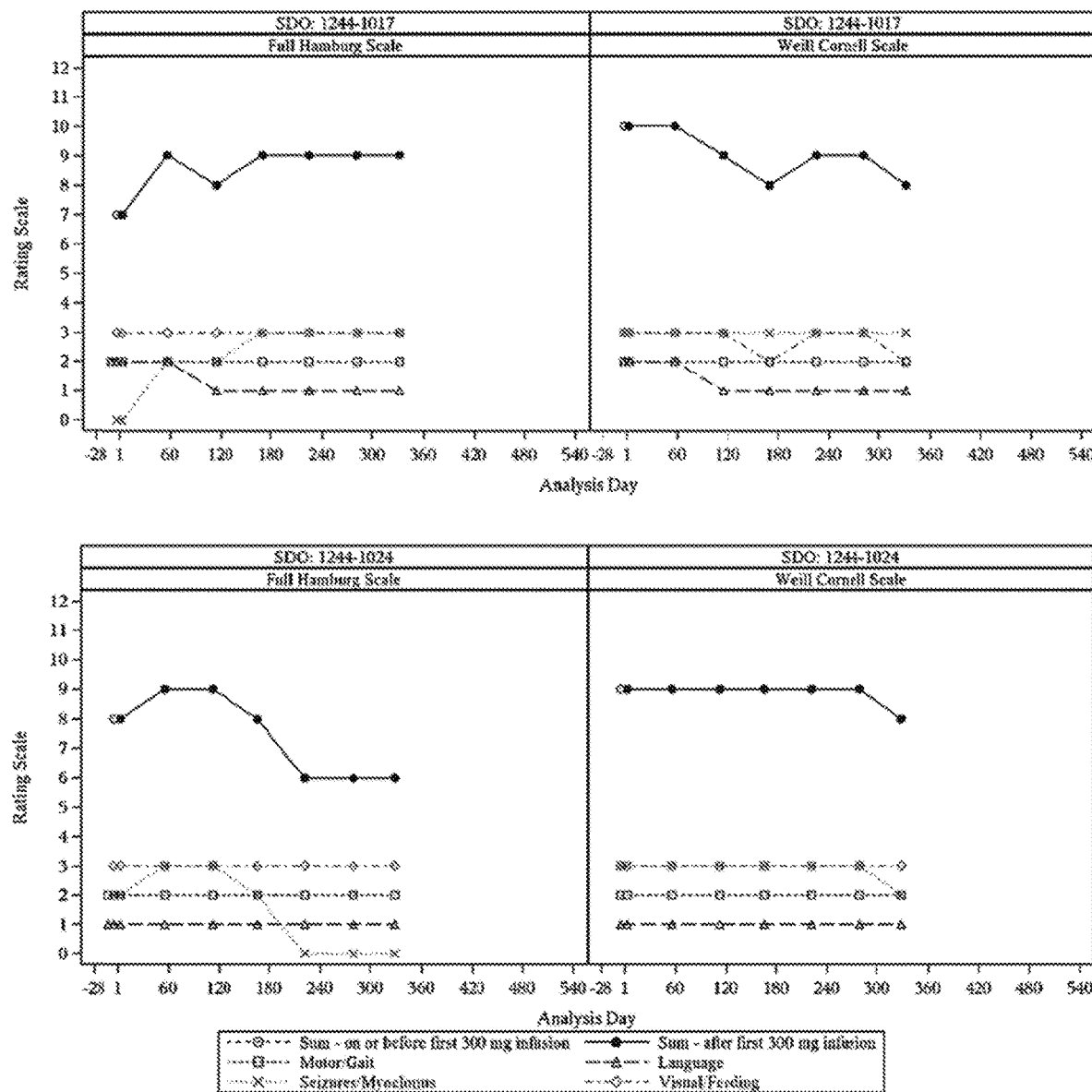
Figure 10J:
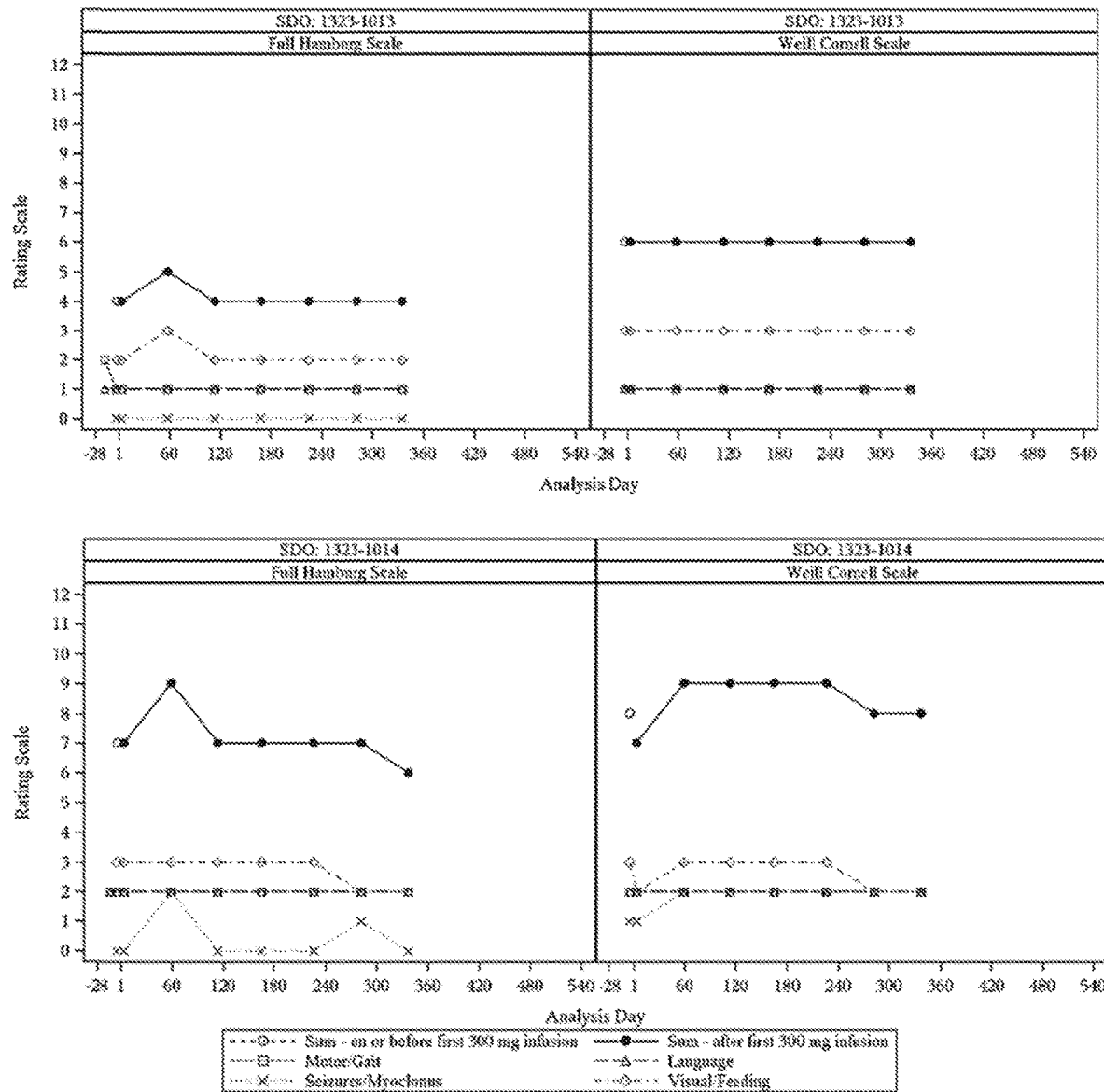
Figure 10K:
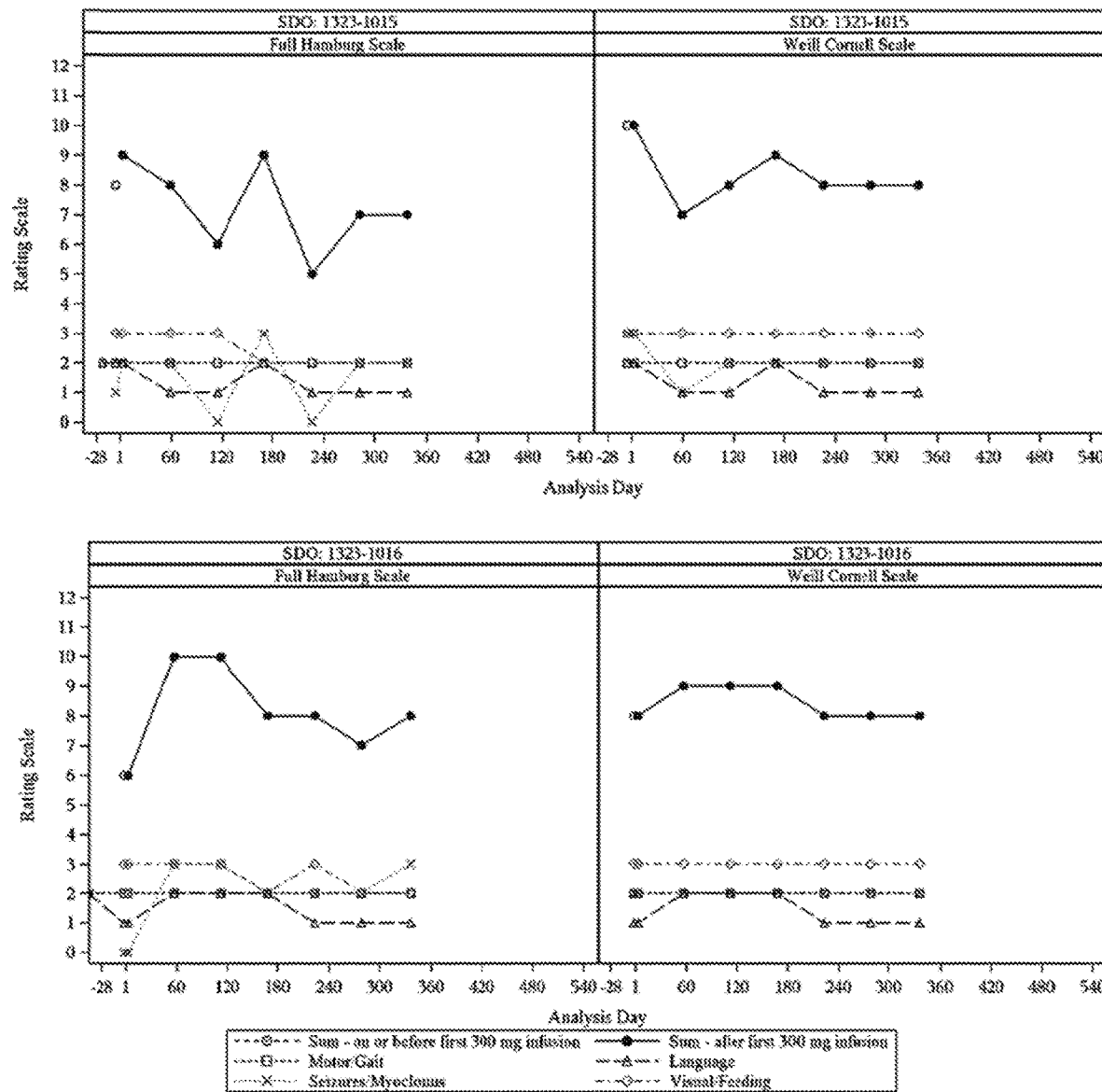

FIG. 9A shows the average change in motor-language rating for patients treated for ≥48 weeks (n=21; dashed line) and the natural history cohort (n=41; solid line). The mean decline in the disease rating for the treated patients was 0.43 (standard deviation 0.839), with a median decline of 0.00 units over 48 weeks. In contrast, the mean decline in the disease rating for the natural history cohort was 2.09 (standard deviation 0.966), with a median decline of 1.87 units over 48 weeks. Overall, there was significant sparing ($p<0.0001$) of 79% of the expected clinical decline for the treated patients. FIG. 9B shows the change in motor-language scores for patients (n=23) from the last measurement before the first 300 mg dose (baseline) to the last 300 mg dose at ≥48 weeks. Overall, 65% (15 out of 23) of patients either improved or had no clinical disease progression during treatment, and 87% (20 out of 23) of the patients performed better during treatment (i.e., had a change of score of −1 or greater) compared to untreated subjects from the natural history study. These analyses uniformly supported the conclusion that there was a dramatic and clinically meaningful stabilization of CLN2 score in treated patients in comparison to matched members of the untreated natural history group, which rapidly and predictably decline.

Effect of Treatment on Clinical Assessments of Vision:

In untreated CLN2 patients, vision loss occurs later than the decline in language and gait, however once symptomatic, the course is predictably rapid and progresses to blindness. Thus, preservation of vision is an important treatment outcome. Loss of vision can be captured on a 0 to 3 point subscale in a similar fashion to other subscales, in which 3 is normal and 0 is functionally blind. There was no unreversed loss in the vision subscale domain for the majority of the treated patients during the treatment period. When the treated patients were matched to untreated natural history subjects by score, age and genotype using the scale composites of the gait, language and vision subscales (0 to 9 units), it was clear that untreated matched natural history patients lost additional points in comparison to the treated group.

FIGS. 6A to 6I show results from nine subjects treated with a rhTPP1 formulation of the disclosure plotted against matched, untreated natural history patients matched by disease rating score using the 0 to 9 unit gait, language and vision subscales as an aggregate. Subject 1244-1001 (FIG. 6A) had a rating decrease of one unit from 6 to 5 points, but then shortly regained a point to a score of 6, with no net changes afterwards. Subject 1244-1002 (FIG. 6B) had a rating increase from 5 points to 6 points, followed by a decrease from 6 points to 4 points, then an increase from 4 points to 5 points, resulting in overall maintenance of the disease rating at the end of the study compared to Day 1. Subjects 1244-1003 (FIG. 6C) and 1244-1010 (FIG. 6I) maintained a rating of 9 points throughout the study, indicating normal gait, language function and vision; subjects 1244-1004 (FIG. 6D) and 1244-1009 (FIG. 6H) maintained a rating of 6 points throughout the study, and subject 1244-1008 (FIG. 6G) maintained a rating of 5 points throughout the study. Subject 1244-1006 (FIG. 6E) had an initial rating decrease of one unit from 6 points to 5 points, followed by a further decrease to 4 points, but regained a unit to a rating of 5 points, with no net changes thereafter. Subject 1287-1005 (FIG. 6F) had a rating decrease from 6 points to 4 points, followed by an increase from 4 points to 5 points and a decrease to 4 points, but regained a unit again, to a final rating of 5 points.

Addition of the vision subscale resulted in no change in the nine treated patients over the treatment period. However, score-matched, untreated natural history patients had significant contribution of vision loss to the aggregate score. There were multiple untreated natural history matches with a greater than 3 point difference compared to the treated patients, showing the contribution of vision decline to the aggregate score over the study period. Addition of the vision subscale thus increased the difference between treated patients and matched untreated natural history patients. As there was no unreversed loss of a disease rating unit in the matched, untreated natural history patients, the observation of treatment effect from rhTPP1 relating to arresting disease progression and stabilizing function can be extended from motor/gait and language to include the clinical domain of vision.

Effect of Treatment on Total Disease Assessment:

Patients were also assessed over the course of the study using a combined 12-point scale containing the complete Hamburg or WCMC scores. The scores on the 12-point scale were the sum of the patient's individual scores for (1) motor/gait, (2) language, (3) seizures/myoclonus and (4) visual/feeding. FIGS. 10A to 10L show results from subjects treated with a rhTPP1 formulation of the disclosure using the 0 to 12 unit combined Hamburg (left panel) and WCMC scale (right panel). Sixteen of 23 patients had no unreversed decline on at least one scale, and 8 had an increased score on at least one scale at the end of the treatment period compared to baseline, confirming an overall treatment benefit in patients receiving rhTPP1.

Effect of Treatment on Brain Volume:

MRI was used to evaluate a secondary endpoint in treated patients. The disease process is characterized by atrophy, cell loss and signal abnormalities. These parameters correlate individually or as a composite score to patient age and disease rating score. Thus, there is a general consensus that disease progression correlates to MRI indices of atrophy, and multiple MRI parameters have been shown to correlate with age and disease severity in CLN2 disease (Dyke et al., *AJNR Am J Neuroradiol.* 2013; 34(4):884-9); (Paniagua et al., *Clin Neuroradiol.* 2013; 23(3):189-96). The imaging database that supports these conclusions is based on cross-sectional correlation of significant numbers of patients, however, there is no within-patient longitudinal acquisition of MRI images. Therefore, there is not the same ability to match longitudinal study-derived MRI analysis to a similarly derived natural history database.

Figure 7:
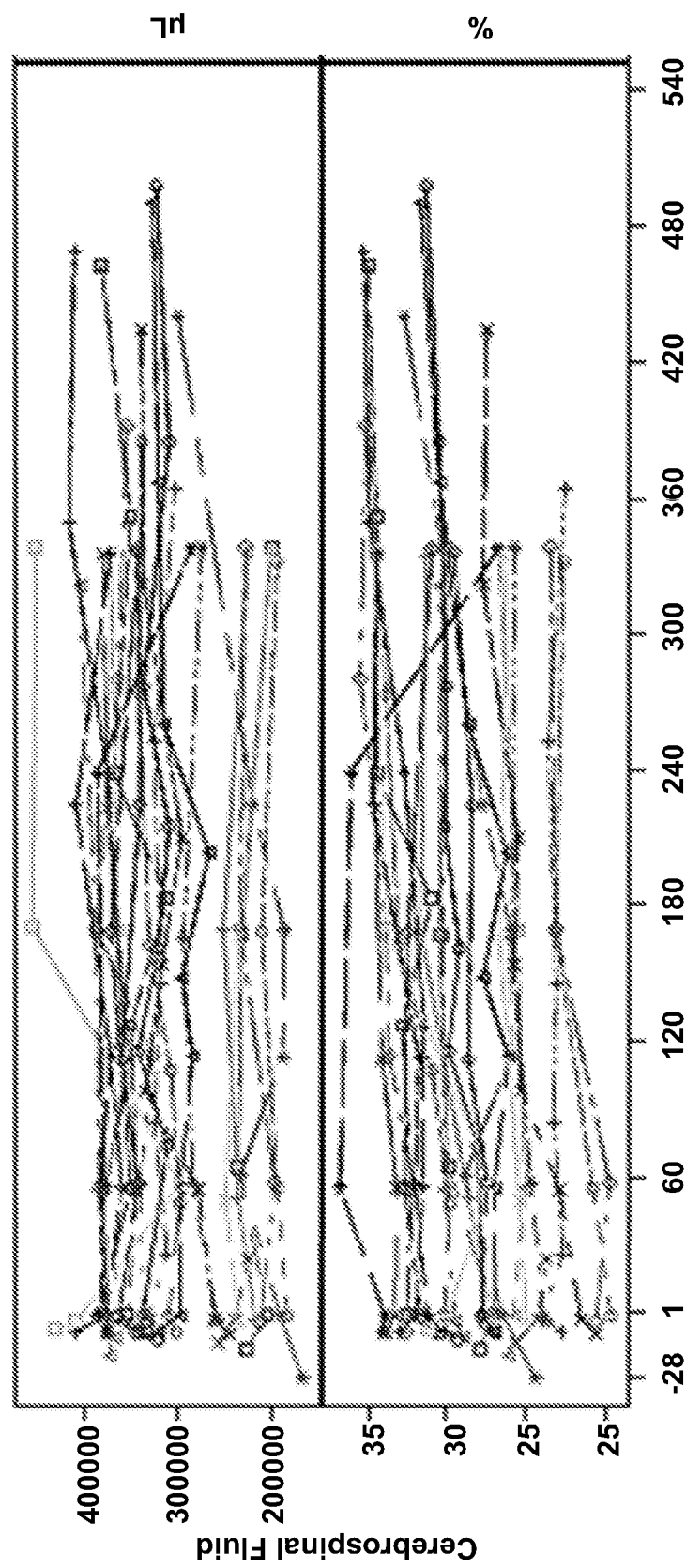
FIG. 7 depicts the volume (top panel) and proportion (bottom panel) of cerebrospinal fluid for all 24 patients measured over the treatment duration. Each line represents one patient.

For analysis of treated patients, MRI acquisition parameters were standardized across the hardware platforms at the study sites. Data was acquired locally, redacted of identifying information, and transmitted to a central imaging core lab. The images were randomized such that the independent radiologist did not know the patient or temporal relationship to baseline. The changes in brain volume were reconstructed from the randomized independent central read. The data was analyzed to compare the studies longitudinally compared to baseline across the treated population. FIG. 7 shows the summary of MRI-measured brain volumes in the treated patients. Cerebral atrophy results in greater volume and proportion of intracranial CSF. An increase in these measurements of atrophy is correlated to age and severity in CLN2 patients. Longitudinal plots of CSF volume and proportion for the treated patients indicated there also appeared to be little, if any change, in measurements of CSF parameters. All patients had MRI volumetry that appeared constant, and consistent with, the stabilization of ratings assessments.

FIGS. 8A to 8L show the longitudinal MRI assessment of brain volumes in the treated patients. Active neurodegeneration in CLN2 patients is characterized by predominant loss of gray matter and compensatory gain of CSF. However, in the assessed period, there were very stable brain volumes and no evidence of a neurodegenerative process in treated patients. The volume of gray matter, shown in FIGS. 8A to 8L as the difference between the CSF and gray matter plot (dashed line) and CSF plot (solid line) in each of the top and bottom panels, was stable throughout the study for each of the treated patients. The change in the volume of cortical grey matter as a percentage of total brain volume from the last measurement prior to the first 300 mg infusion (baseline) compared to the last observation at ≥48 weeks of treatment is shown in Table 6 below.

TABLE 6

| Change from Baseline to Last Observation | Overall (n =23) |
| --- | --- |
| N | 23 |
| Mean (SD) | −2.3 (2.01) |
| Median | −2.6 |
| Min, Max | −5.8, 3.1 |

The longitudinal change of the cortical volume is −1% each year in normal children age 4-12, but −12.5% each year for untreated CLN2 patients. During treatment with rhTPP1, the volume of CSF, gray matter, and white matter stayed relatively constant, attenuating 89% of disease-related loss of cortical volume.

Adverse Events:

One patient withdrew from the study due to inability to comply with the protocol. The remaining 23 patients remained on the study and tolerated treatment with the rhTPP1 drug product via the ICV route. There were no deaths, treatment-related withdrawals, or study discontinuations due to a safety-related reason. Consistent with minimal impact of device implantation, all patients were dosed within a week of surgery. Out of a total of 325 infusions, only 5 (1.5%) were interrupted for any reason, with only 2 (0.6%) of these interrupted for adverse event-related reasons. The most frequent non-CLN2 disease associated adverse events observed in the study were pyrexia, hypersensitivity, and upper respiratory tract infection (each in 25% of subjects overall). In general, these events were mild, self-limited and managed medically. Investigator-defined hypersensitivity events were associated with few peripheral manifestations and were medically managed with a combination of antipyretics, antihistamine and/or steroids. Laboratory data demonstrated a lack of clinically relevant changes in peripheral labs. In the CSF, some patients had mild, transient pleocytosis with no change in CSF glucose or protein. In summary, the evaluation of safety parameters demonstrated that treatment with a rhTPP1 formulation of the disclosure via ICV infusion was tolerated in all patients.

CONCLUSION

The clinical study demonstrated that every patient with a treatment exposure of more than 36 weeks had significant clinical benefit, characterized by complete arrest in the progression of CLN2 disease, which constituted maximal treatment benefit, as gain of function was not expected in the time frame for patients with moderate progression and active degeneration.

This finding was even more compelling when the patients were matched to members of the natural history database based on multiple parameters including baseline disease rating, age and genotype. This matching revealed that during the same period of time that treated subjects experienced halted disease progression on treatment with the rhTPP1 drug product, the matched untreated natural history patients experienced substantial loss of function. All treated patients showed, therefore, arrest of disease progression compared to active disease progression in matched untreated natural history patients. The median rate of decline in the untreated natural history population was estimated at 2.1 points each year based on the available natural history data, with each unit of decline representing a significant milestone loss of physiological function. For the majority of patients entering the study, the preservation of 2 units translated to continued independent ambulation and meaningful communication.

Overall, the results demonstrated that a rhTPP1 formulation and method of treatment of the disclosure has an acceptable safety/tolerability profile. No subjects discontinued the study or treatment due to an adverse event. One subject withdrew from the study after one treatment dose due to inability to comply with the protocol. Analysis of PK and immunogenicity revealed high CNS delivery, and no formation of antibodies in the CSF.

The foregoing Examples demonstrate that the formulations and methods comprising rhTPP1 described herein are effective in preventing or treating CLN2 disease and/or one or more clinical symptoms of CLN2. In a disease whose clinical course is characterized by rapid, inexorable and irreversible neurodegenerative disease progression, halting disease progression, especially in each treated patient, is a substantial and unexpected clinical benefit.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed:

1. A method of treating Neuronal Ceroid Lipofuscinosis (CLN2) disease comprising administering i) about 10 mL of a composition comprising a dose of about 300 mg of recombinant human tripeptidyl peptidase-1 (rhTPP1) to a subject in need thereof, wherein the composition is administered to the subject over a period of about 4 hours, or ii) administering a rhTPP1 composition to a subject in need thereof at a dose of about 300 mg, wherein the dose is administered to the subject at a rate less than or equal to 75 mg/2.5 mL/hour and wherein the composition has a pH of 6.5 and the rhTPP1 is not aggregated.

2. A method of preventing symptoms of Neuronal Ceroid Lipofuscinosis (CLN2) disease comprising
   i) administering about 10 mL of a composition comprising a dose of about 300 mg of recombinant human tripeptidyl peptidase-1 (rhTPP1) to a subject in need thereof, wherein the composition is administered to the subject over a period of about 4 hours; ii) administering a rhTPP1 composition to a subject in need thereof at a dose of about 300 mg, wherein the dose is administered to the subject at a rate less than or equal to 75 mg/hour; or
   iii) administering a rhTPP1 composition to a subject in need thereof at a dose of about 300 mg, wherein the dose is administered to the subject at a rate less than or equal to 75 mg/2.5 mL/hour and wherein the composition has a pH of 6.5 and the rhTPP1 is not aggregated.

3. The method of claim 2, wherein the formulation, composition or dose is administered intracerebroventricularly, intrathecally, intraocularly, intracerebroventricularly and intraocularly, or intrathecally and intraocularly.

4. A method of treating Neuronal Ceroid Lipofuscinosis (CLN2) disease comprising administering a composition comprising rhTPP1 to a subject in need thereof at a dose of rhTPP1 effective to maintain a physiological function or slow or reduce deterioration of a physiological function in the subject, wherein the physiological function is language function, motor function, vision or feeding function, wherein the composition comprises rhTPP1 at a concentration of from about 25 mg/mL to about 35 mq/mL, further comprising potassium chloride at a concentration of about 0.01 mg/mL to about 1 mg/mL, magnesium chloride hexahydrate at a concentration of about 0.01 mg/mL to about 1 mg/mL, and calcium chloride dehydrate at a concentration of about 0.01 mg/m L to about 1 mq/m L and wherein the composition has a pH of 6.5 and the rhTPP1 is not aggregated.

5. The method of claim 4, wherein the dose of rhTTP1 i) is effective to maintain language function or slow or reduce deterioration of language function in the subject; and/or ii) is effective to maintain motor function or slow or reduce deterioration of motor function in the subject.

6. The method of claim 4, wherein the dose is i) about 10 mL of a composition comprising about 300 mg of rhTPP1 administered to the subject over a period of about 4 hours; ii) about 300 mg of rhTPP1 administered to the subject at a rate less than or equal to about 75 mg/hr; or iii) about 300 MCI of rhTPP1 administered to the subject at a rate less than or equal to about 75 mg/2.5 mL/hour.

7. The method of claim 4, wherein the dose is administered every other week.

8. The method of claim 4, wherein the dose is administered intracerebroventricularly, intrathecally, intraocularly, intracerebroventricularly and intraocularly.

9. The method of claim 4, wherein the dose is administered in a formulation comprising sodium phosphate dibasic heptahydrate at a concentration of about 0.01 mg/mL to about 1 mg/mL, sodium phosphate monobasic monohydrate at a concentration of about 0.01 mg/mL to about 1 mg/mL, and sodium chloride at a concentration of about 1 mg/mL to about 20 mg/mL.

10. The method of claim 4, wherein the dose is administered in a formulation comprising sodium phosphate dibasic heptahydrate at a concentration of about 0.11 mg/mL, sodium phosphate monobasic monohydrate at a concentration of about 0.08 mg/mL, sodium chloride at a concentration of about 8.77 mg/mL, potassium chloride at a concentration of about 0.22 mg/mL, magnesium chloride hexahydrate at a concentration of about 0.16 mg/mL, and calcium chloride dihydrate at a concentration of about 0.21 mg/mL.

11. A method of maintaining vision or slowing or reducing deterioration of vision in a subject having Neuronal Ceroid Lipofuscinosis (CLN2) disease comprising administering a therapeutically effective dose of rhTPP1 to the subject wherein the composition comprises rhTPP1 at a concentration of from about 25 mg/mL to about 35 mg/mL, further comprising potassium chloride at a concentration of about 0.01 mg/mL to about 1 mg/mL, magnesium chloride hexahydrate at a concentration of about 0.01 mg/mL to about 1 mg/mL, and calcium chloride dehydrate at a concentration of about 0.01 mg/mL to about 1 mg/mL, and wherein the composition has a pH of 6.5 and the rhTPP1 is not aggregated.

12. A method of treating Neuronal Ceroid Lipofuscinosis (CLN2) disease comprising administering a composition comprising rhTPP1 to a subject in need thereof at a dose effective to improve physiological function in the subject, wherein the physiological function is language function, motor function, vision or feeding function, wherein the composition comprises rhTPP1 at a concentration of from about 25 mg/mL to about 35 mg/mL, further comprising potassium chloride at a concentration of about 0.01 mg/mL to about 1 mg/mL, magnesium chloride hexahydrate at a concentration of about 0.01 mg/mL to about 1 mg/mL, and calcium chloride dehydrate at a concentration of about 0.01 mg/mL to about 1 mg/mL, and wherein the composition has a pH of 6.5 and the rhTPP1 is not aggregated.

13. The method of claim 12, wherein the dose of rhTPP1 is effective to provide an improvement in vision.

14. The method of claim 13, wherein the improvement in vision is an increase equal to or more than one point as measured using a Hamburg disease rating scale.

15. A method of improving language function and/or motor function in a subject having Neuronal Ceroid Lipofuscinosis (CLN2) disease, comprising administering a composition comprising a therapeutically effective dose of rhTPP1 to the subject, wherein the composition comprises rhTPP1 at a concentration of from about 25 mg/mL to about 35 mg/mL, further comprising potassium chloride at a concentration of about 0.01 mg/mL to about 1 mg/mL, magnesium chloride hexahydrate at a concentration of about 0.01 mg/mL to about 1 mg/mL, and calcium chloride dehydrate at a concentration of about 0.01 mg/mL to about 1 mg/mL, and wherein the composition has a pH of 6.5 and the rhTPP1 is not aggregated.

16. A method of treating Neuronal Ceroid Lipofuscinosis (CLN2) disease comprising administering a composition comprising rhTPP1 to a subject in need thereof at a dose effective to prevent or improve a neurological symptom of the disease, wherein the neurological symptom is a decrease in brain volume, a decrease in gray matter in the brain, a seizure, or an increase in cranial cerebrospinal fluid, wherein the composition comprises rhTPP1 at a concentration of from about 25 mg/mL to about 35 mg/m L, further comprising potassium chloride at a concentration of about 0.01 mg/mL to about 1 mg/mL, magnesium chloride hexahydrate at a concentration of about 0.01 mg/mL to about 1 mg/mL, and calcium chloride dehydrate at a concentration of about 0.01 mg/mL to about 1 mg/mL and wherein the composition has a pH of 6.5 and the rhTPP1 is not aggregated.

17. The method of claim 16, wherein the dose of rhTPP1 is effective to i) maintain grey matter or slow or reduce deterioration of gray matter in the brain of the subject; ii) reduce the number of seizures per month that the subject experiences; and/or iii) maintain the volume of cranial cerebrospinal fluid or slow the increase in the volume of cranial cerebrospinal fluid in the subject.

18. A method of maintaining brain volume or slowing or reducing a decrease in brain volume in a subject having Neuronal Ceroid Lipofuscinosis (CLN2) disease, comprising administering a composition comprising a therapeutically effective dose of rhTPP1 to the subject, wherein the composition comprises rhTPP1 at a concentration of from about 25 mg/mL to about 35 mg/mL, further comprising potassium chloride at a concentration of about 0.01 mg/mL to about 1 mg/mL, magnesium chloride hexahydrate at a concentration of about 0.01 mg/mL to about 1 mg/mL, and calcium chloride dehydrate at a concentration of about 0.01 mg/mL to about 1 mg/mL, and wherein the composition has a pH of 6.5 and the rhTPP1 is not aggregated.

* * * * *

UNITED STATES PATENT AND TRADEMARK OFFICE
CERTIFICATE OF CORRECTION

PATENT NO.        : 11,229,687 B2
APPLICATION NO.   : 16/941454
DATED             : January 25, 2022
INVENTOR(S)       : Lester et al.

It is certified that error appears in the above-identified patent and that said Letters Patent is hereby corrected as shown below:

In the Claims

At Column 35, Lines 48-52, "ii) administering a rhTPP1 ............................75 mg/hour; or" should be at Line 49, as a continuation subpoint.

At Column 36, Line 32, "mq/mL," should be -- mg/mL, --.

At Column 36, Line 37, "mg/m L" should be -- mg/mL --.

At Column 36, Line 37, "mq/m L" should be -- mg/mL --.

At Column 38, Line 16, "mg/m L," should be -- mg/mL, --.

Signed and Sealed this
Second Day of August, 2022

Katherine Kelly Vidal
*Director of the United States Patent and Trademark Office*

SEQUENCE LISTING

<160> NUMBER OF SEQ ID NOS: 2

<210> SEQ ID NO 1
<211> LENGTH: 544
<212> TYPE: PRT
<213> ORGANISM: Homo sapiens

<400> SEQUENCE: 1

```
Ser Tyr Ser Pro Glu Pro Asp Gln Arg Arg Thr Leu Pro Pro Gly Trp
 1               5                  10                  15

Val Ser Leu Gly Arg Ala Asp Pro Glu Glu Leu Ser Leu Thr Phe
                20                  25                  30

Ala Leu Arg Gln Gln Asn Val Glu Arg Leu Ser Glu Leu Val Gln Ala
                35                  40                  45

Val Ser Asp Pro Ser Pro Gln Tyr Gly Lys Tyr Leu Thr Leu Glu
 50                  55                  60

Asn Val Ala Asp Leu Val Arg Pro Ser Pro Leu Thr Leu His Thr Val
 65                  70                  75                  80

Gln Lys Trp Leu Leu Ala Ala Gly Ala Gln Lys Cys His Ser Val Ile
                85                  90                  95

Thr Gln Asp Phe Leu Thr Cys Trp Leu Ser Ile Arg Gln Ala Glu Leu
                100                 105                 110

Leu Leu Pro Gly Ala Glu Phe His His Tyr Val Gly Pro Thr Glu
                115                 120                 125

Thr His Val Val Arg Ser Pro His Pro Tyr Gln Leu Pro Gln Ala Leu
                130                 135                 140

Ala Pro His Val Asp Phe Val Gly Gly Leu His Arg Phe Pro Pro Thr
145                 150                 155                 160

Ser Ser Leu Arg Gln Arg Pro Glu Pro Gln Val Thr Gly Thr Val Gly
                165                 170                 175

Leu His Leu Gly Val Thr Pro Ser Val Ile Arg Lys Arg Tyr Asn Leu
                180                 185                 190

Thr Ser Gln Asp Val Gly Ser Gly Thr Ser Asn Asn Ser Gln Ala Cys
                195                 200                 205

Ala Gln Phe Leu Glu Gln Tyr Phe His Asp Ser Asp Leu Ala Gln Phe
                210                 215                 220

Met Arg Leu Phe Gly Gly Asn Phe Ala His Gln Ala Ser Val Ala Arg
225                 230                 235                 240

Val Val Gly Gln Gln Gly Arg Gly Arg Ala Gly Ile Glu Ala Ser Leu
                245                 250                 255

Asp Val Gln Tyr Leu Met Ser Ala Gly Ala Asn Ile Ser Thr Trp Val
                260                 265                 270

Tyr Ser Ser Pro Gly Arg His Glu Gly Gln Glu Pro Phe Leu Gln Trp
                275                 280                 285

Leu Met Leu Leu Ser Asn Glu Ser Ala Leu Pro His Val His Thr Val
                290                 295                 300

Ser Tyr Gly Asp Asp Glu Asp Ser Leu Ser Ser Ala Tyr Ile Gln Arg
305                 310                 315                 320

Val Asn Thr Glu Leu Met Lys Ala Ala Ala Arg Gly Leu Thr Leu Leu
                325                 330                 335

Phe Ala Ser Gly Asp Ser Gly Ala Gly Cys Trp Ser Val Ser Gly Arg
                340                 345                 350

His Gln Phe Arg Pro Thr Phe Pro Ala Ser Ser Pro Tyr Val Thr Thr
                355                 360                 365
```

Val Gly Gly Thr Ser Phe Gln Glu Pro Phe Leu Ile Thr Asn Glu Ile
    370                 375                 380

Val Asp Tyr Ile Ser Gly Gly Phe Ser Asn Val Phe Pro Arg Pro
385                 390                 395                 400

Ser Tyr Gln Glu Glu Ala Val Thr Lys Phe Leu Ser Ser Pro His
                405                 410                 415

Leu Pro Pro Ser Ser Tyr Phe Asn Ala Ser Gly Arg Ala Tyr Pro Asp
                420                 425                 430

Val Ala Ala Leu Ser Asp Gly Tyr Trp Val Val Ser Asn Arg Val Pro
                435                 440                 445

Ile Pro Trp Val Ser Gly Thr Ser Ala Ser Thr Pro Val Phe Gly Gly
450                 455                 460

Ile Leu Ser Leu Ile Asn Glu His Arg Ile Leu Ser Gly Arg Pro Pro
465                 470                 475                 480

Leu Gly Phe Leu Asn Pro Arg Leu Tyr Gln Gln His Gly Ala Gly Leu
                485                 490                 495

Phe Asp Val Thr Arg Gly Cys His Glu Ser Cys Leu Asp Glu Val
                500                 505                 510

Glu Gly Gln Gly Phe Cys Ser Gly Pro Gly Trp Asp Pro Val Thr Gly
                515                 520                 525

Trp Gly Thr Pro Asn Phe Pro Ala Leu Leu Lys Thr Leu Leu Asn Pro
                530                 535                 540

<210> SEQ ID NO 2
<211> LENGTH: 368
<212> TYPE: PRT
<213> ORGANISM: Homo sapiens

<400> SEQUENCE: 2

Leu His Leu Gly Val Thr Pro Ser Val Ile Arg Lys Arg Tyr Asn Leu
1               5                   10                  15

Thr Ser Gln Asp Val Gly Ser Gly Thr Ser Asn Asn Ser Gln Ala Cys
                20                  25                  30

Ala Gln Phe Leu Glu Gln Tyr Phe His Asp Ser Asp Leu Ala Gln Phe
                35                  40                  45

Met Arg Leu Phe Gly Gly Asn Phe Ala His Gln Ala Ser Val Ala Arg
50                  55                  60

Val Val Gly Gln Gln Gly Arg Gly Arg Ala Gly Ile Glu Ala Ser Leu
65                  70                  75                  80

Asp Val Gln Tyr Leu Met Ser Ala Gly Ala Asn Ile Ser Thr Trp Val
                85                  90                  95

Tyr Ser Ser Pro Gly Arg His Glu Gly Gln Glu Pro Phe Leu Gln Trp
                100                 105                 110

Leu Met Leu Leu Ser Asn Glu Ser Ala Leu Pro His Val His Thr Val
                115                 120                 125

Ser Tyr Gly Asp Asp Glu Asp Ser Leu Ser Ser Ala Tyr Ile Gln Arg
                130                 135                 140

Val Asn Thr Glu Leu Met Lys Ala Ala Arg Gly Leu Thr Leu Leu
145                 150                 155                 160

Phe Ala Ser Gly Asp Ser Gly Ala Gly Cys Trp Ser Val Ser Gly Arg
                165                 170                 175

His Gln Phe Arg Pro Thr Phe Pro Ala Ser Ser Pro Tyr Val Thr Thr
                180                 185                 190

Val Gly Gly Thr Ser Phe Gln Glu Pro Phe Leu Ile Thr Asn Glu Ile
                195                 200                 205

```
Val Asp Tyr Ile Ser Gly Gly Gly Phe Ser Asn Val Phe Pro Arg Pro
    210                 215                 220

Ser Tyr Gln Glu Glu Ala Val Thr Lys Phe Leu Ser Ser Ser Pro His
225                 230                 235                 240

Leu Pro Pro Ser Ser Tyr Phe Asn Ala Ser Gly Arg Ala Tyr Pro Asp
                245                 250                 255

Val Ala Ala Leu Ser Asp Gly Tyr Trp Val Val Ser Asn Arg Val Pro
                260                 265                 270

Ile Pro Trp Val Ser Gly Thr Ser Ala Ser Thr Pro Val Phe Gly Gly
            275                 280                 285

Ile Leu Ser Leu Ile Asn Glu His Arg Ile Leu Ser Gly Arg Pro Pro
    290                 295                 300

Leu Gly Phe Leu Asn Pro Arg Leu Tyr Gln Gln His Gly Ala Gly Leu
305                 310                 315                 320

Phe Asp Val Thr Arg Gly Cys His Glu Ser Cys Leu Asp Glu Glu Val
                325                 330                 335

Glu Gly Gln Gly Phe Cys Ser Gly Pro Gly Trp Asp Pro Val Thr Gly
                340                 345                 350

Trp Gly Thr Pro Asn Phe Pro Ala Leu Leu Lys Thr Leu Leu Asn Pro
            355                 360                 365
```